(12) United States Patent
Wiggers et al.

(10) Patent No.: US 11,058,393 B2
(45) Date of Patent: *Jul. 13, 2021

(54) IMAGING-BASED SELF-ADJUSTING RADIATION THERAPY SYSTEMS, DEVICES, AND METHODS

(71) Applicants: VARIAN MEDICAL SYSTEMS, INC., Palo Alto, CA (US); VARIAN MEDICAL SYSTEMS INTERNATIONAL AG, Zug (CH)

(72) Inventors: Robert T. Wiggers, Belmont, CA (US); Daryl Leung, Palo Alto, CA (US); Reto W. Filiberti, Baar (CH); Daniel Morf, Buch am Irchel (CH); Diana Kung, Sunnyvale, CA (US); Stephen Gaudio, Mountain View, CA (US)

(73) Assignees: VARIAN MEDICAL SYSTEMS INC., Palo Alto, CA (US); VARIAN MEDICAL SYSTEMS INTERNATIONAL AG, Steinhausen (CH)

( * ) Notice: Subject to any disclaimer, the term of this patent is extended or adjusted under 35 U.S.C. 154(b) by 645 days.

This patent is subject to a terminal disclaimer.

(21) Appl. No.: 15/782,558

(22) Filed: Oct. 12, 2017

(65) Prior Publication Data
US 2018/0028143 A1    Feb. 1, 2018

Related U.S. Application Data

(63) Continuation of application No. 14/296,233, filed on Jun. 4, 2014, now Pat. No. 9,844,358.

(51) Int. Cl.
 A61B 6/00    (2006.01)
 A61B 6/06    (2006.01)
 A61N 5/10    (2006.01)

(52) U.S. Cl.
 CPC ............... *A61B 6/588* (2013.01); *A61B 6/06* (2013.01); *A61B 6/4035* (2013.01); *A61B 6/545* (2013.01);
 (Continued)

(58) Field of Classification Search
 CPC .. A61B 6/00; A61B 6/48; A61B 6/488; A61B 6/54; A61B 6/542; A61B 6/545;
 (Continued)

(56) References Cited

U.S. PATENT DOCUMENTS 5,394,452 A    2/1995  Swerdloff et al.
6,322,249 B1   11/2001 Wofford et al.
(Continued)

OTHER PUBLICATIONS

Herman et al., "Guide to clinical use of electronic portal imaging," Journal of Applied Clinical Medical Physics, vol. 1, No. 2, Spring 2000.
(Continued)

*Primary Examiner* — Anastasia Midkiff
(74) *Attorney, Agent, or Firm* — SGPatents PLLC

(57) ABSTRACT

Systems, devices, and methods are presented for automatic tuning, calibration, and verification of radiation therapy systems comprising control elements configured to control parameters of the radiation therapy systems based on images obtained using electronic portal imaging devices (EPIDs) included in the radiation therapy system.

40 Claims, 42 Drawing Sheets

(52) U.S. Cl.
CPC .............. *A61B 6/547* (2013.01); *A61B 6/583* (2013.01); *A61B 6/586* (2013.01); *A61B 6/587* (2013.01); *A61N 5/1065* (2013.01); *A61B 6/585* (2013.01); *A61N 2005/1054* (2013.01); *A61N 2005/1056* (2013.01); *A61N 2005/1061* (2013.01)

(58) Field of Classification Search
CPC ........... A61B 6/547; A61B 6/548; A61B 6/58; A61B 6/582; A61B 6/586; A61B 6/587; A61B 6/588; A61B 6/589; A61B 2560/00; A61B 2560/0266; A61N 5/00; A61N 5/10; A61N 5/1048; A61N 5/1049; A61N 5/1064; A61N 5/1065; A61N 5/1067; A61N 5/1069; A61N 5/107; A61N 5/1075; A61N 5/1077; A61N 2005/1054; A61N 2005/1056; A61N 2005/1061
See application file for complete search history.

(56) References Cited

U.S. PATENT DOCUMENTS

| | | |
|---|---|---|
| 6,345,114 B1 | 2/2002 | Mackie et al. |
| 6,438,202 B1 | 8/2002 | Olivera et al. |
| 6,614,036 B1 | 9/2003 | Reinstein |
| 6,783,275 B2 | 8/2004 | Ghelmansarai |
| 7,013,228 B2 | 3/2006 | Ritt |
| 7,332,723 B2 * | 2/2008 | Histrov ................ G01T 1/2018 250/368 |
| 7,801,269 B2 | 9/2010 | Cravens et al. |
| 8,130,905 B1 | 3/2012 | Nelms |
| 8,542,797 B2 | 9/2013 | Roberts |
| 9,844,358 B2 * | 12/2017 | Wiggers ................ A61B 6/545 |
| 2003/0007601 A1 | 1/2003 | Jaffray et al. |
| 2008/0031406 A1 | 2/2008 | Yan et al. |
| 2009/0022383 A1 | 1/2009 | Falco et al. |
| 2009/0134334 A1 * | 5/2009 | Nelson ................. G01T 1/2008 250/361 R |
| 2009/0283682 A1 | 11/2009 | Star-Lack et al. |
| 2010/0183118 A1 | 7/2010 | Star-Lack et al. |
| 2011/0058647 A1 | 3/2011 | Star-Lack et al. |
| 2012/0014618 A1 | 1/2012 | Sun et al. |
| 2012/0230462 A1 | 9/2012 | Robar et al. |
| 2014/0133726 A1 | 5/2014 | Garner et al. |

OTHER PUBLICATIONS

Grelewicz et al., "An EPID based method for performing high accuracy calibration between an optical external marker tracking device and the LINAC reference frame," Med Phys. May 2012, 39(5): 2771-2779.

Liu et al., "Assessment of flatness and symmetry of megavoltage x-ray beam with an electronic portal imaging device (EPID)," Australasian Physical & Engineering Sciences in Medicine vol. 25 No. 2, 2002.

Njeh, "A simple quality assurance test tool for the visual verification of light and radiation field congruent using electronic portal images device and computed radiography," Radiation Oncology 2012, 7:49.

Mitterlechner et al., "Dosimetric exact multileaf collimator calibration by means of aSi:H Electronic Portal Imaging Device," Paracelsus Medizinische Privatuniversitat.

Beck et al., "Electron beam quality control using an amorphous silicon EPID," Med. Phys. 36, 1859 (2009).

Nadernejad et al., "Edge Detection Techniques: Evaluations and Comparisons," Applied Mathematical Sciences, vol. 2, 2008, No. 31, 1507-1520.

Maini et al., "Study and Comparison of Various Image Edge Detection Techniques," International Journal of Imaging Processing (IJIP), vol. (3): Issue (1).

Solimanian et al., "Standard calibration of ionization chambers used in radiation therapy dosimetry and evaluation of uncertainties," Iran. J. Radiat. Res., 2010, 8(3): 195-199.

* cited by examiner

FIG. 1
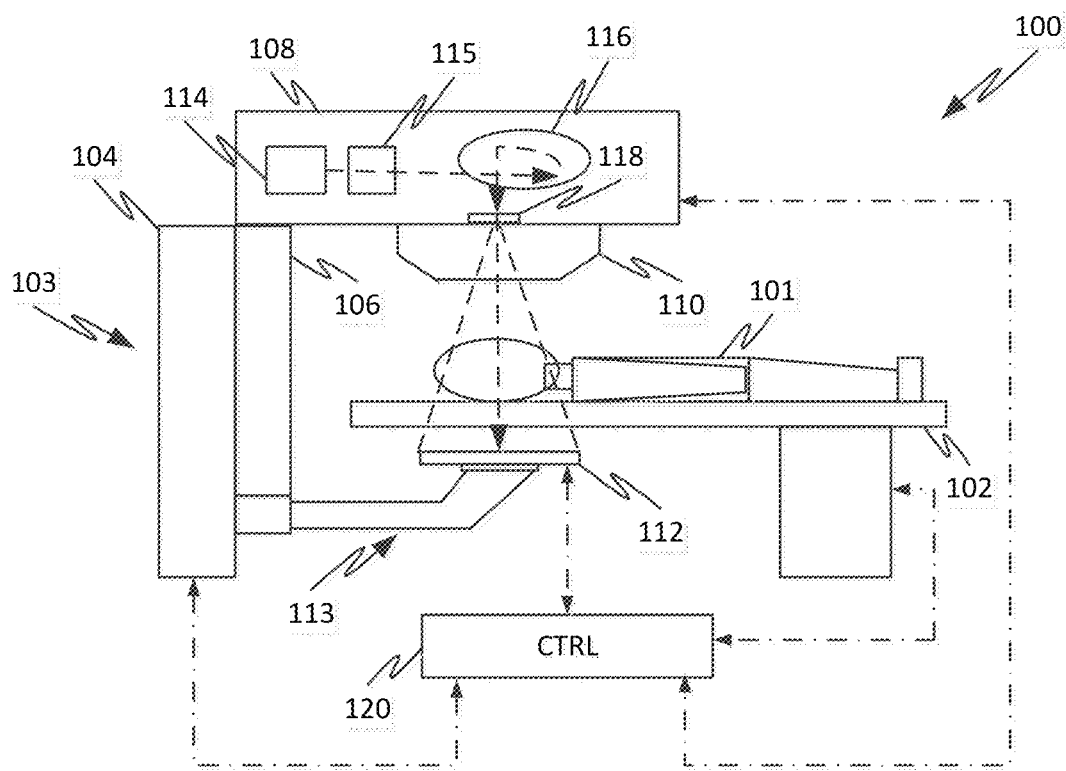
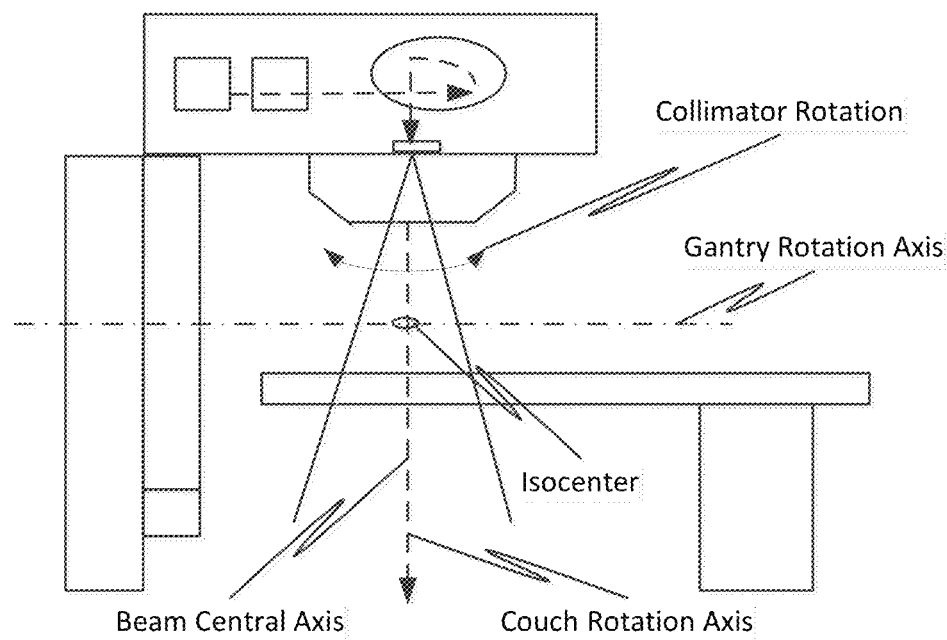
FIG. 2A

FIG. 7
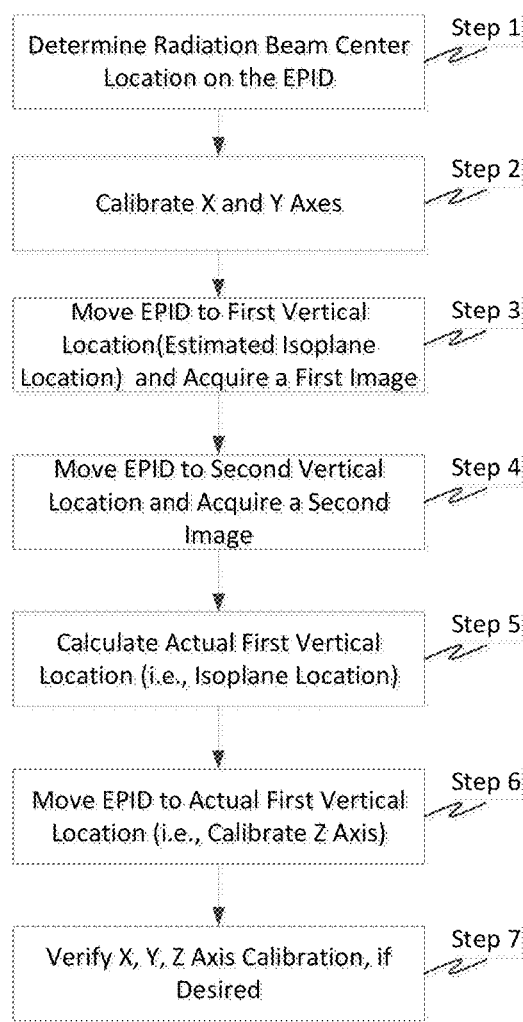
FIG. 8
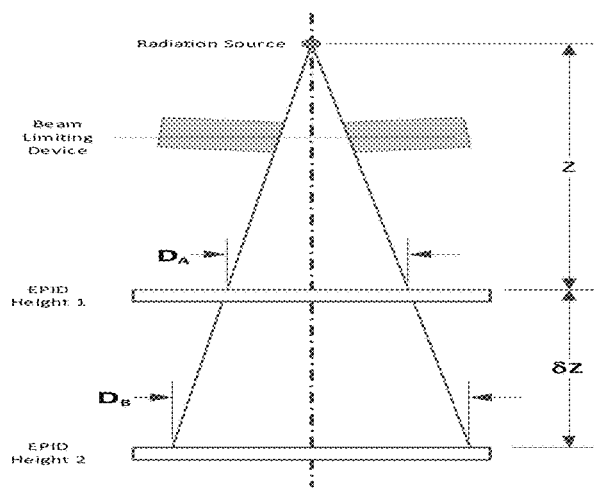

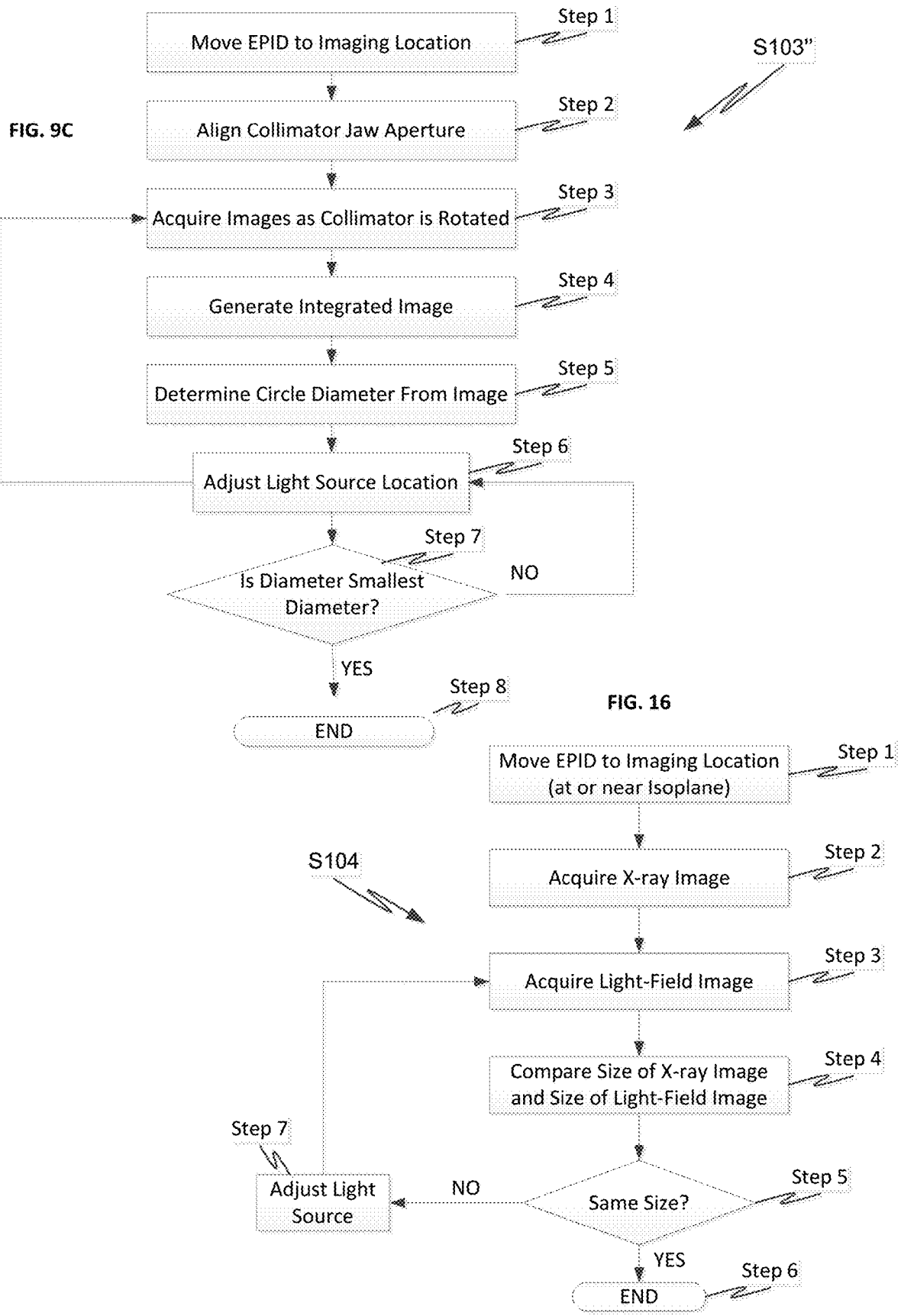

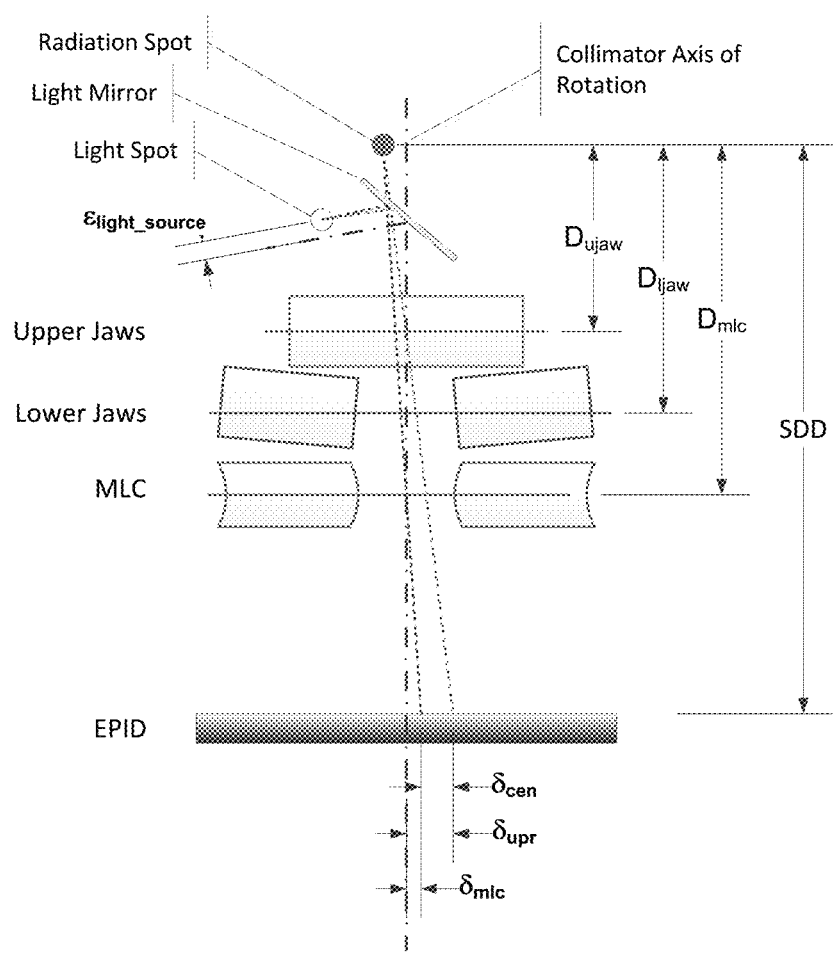

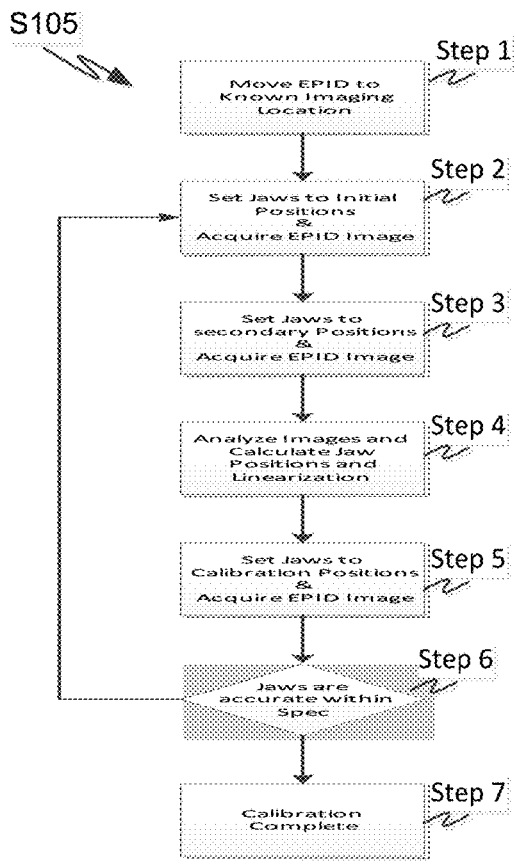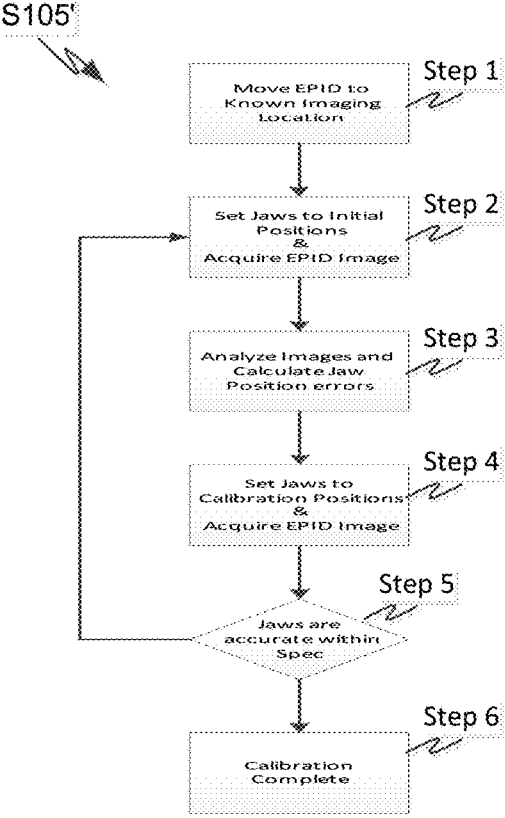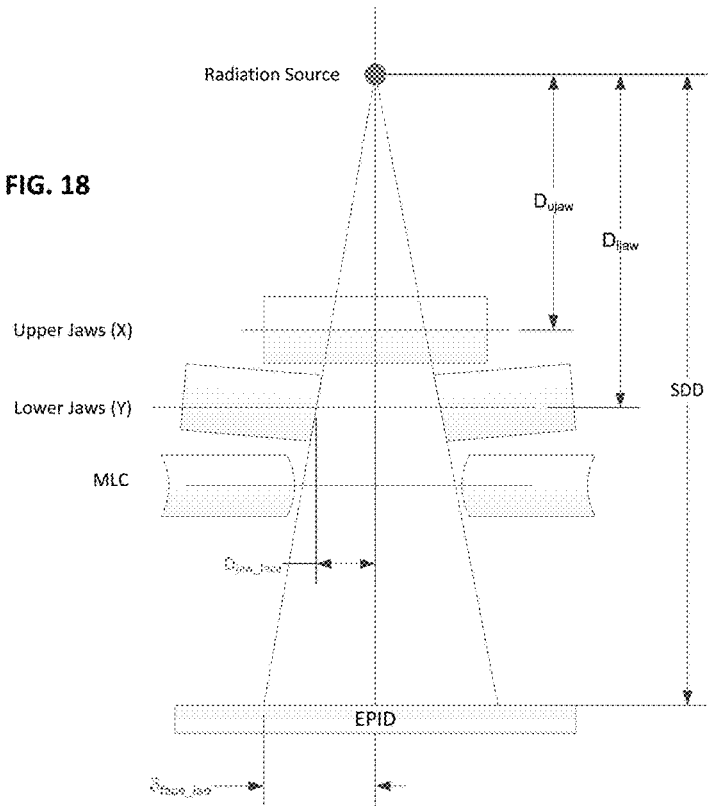

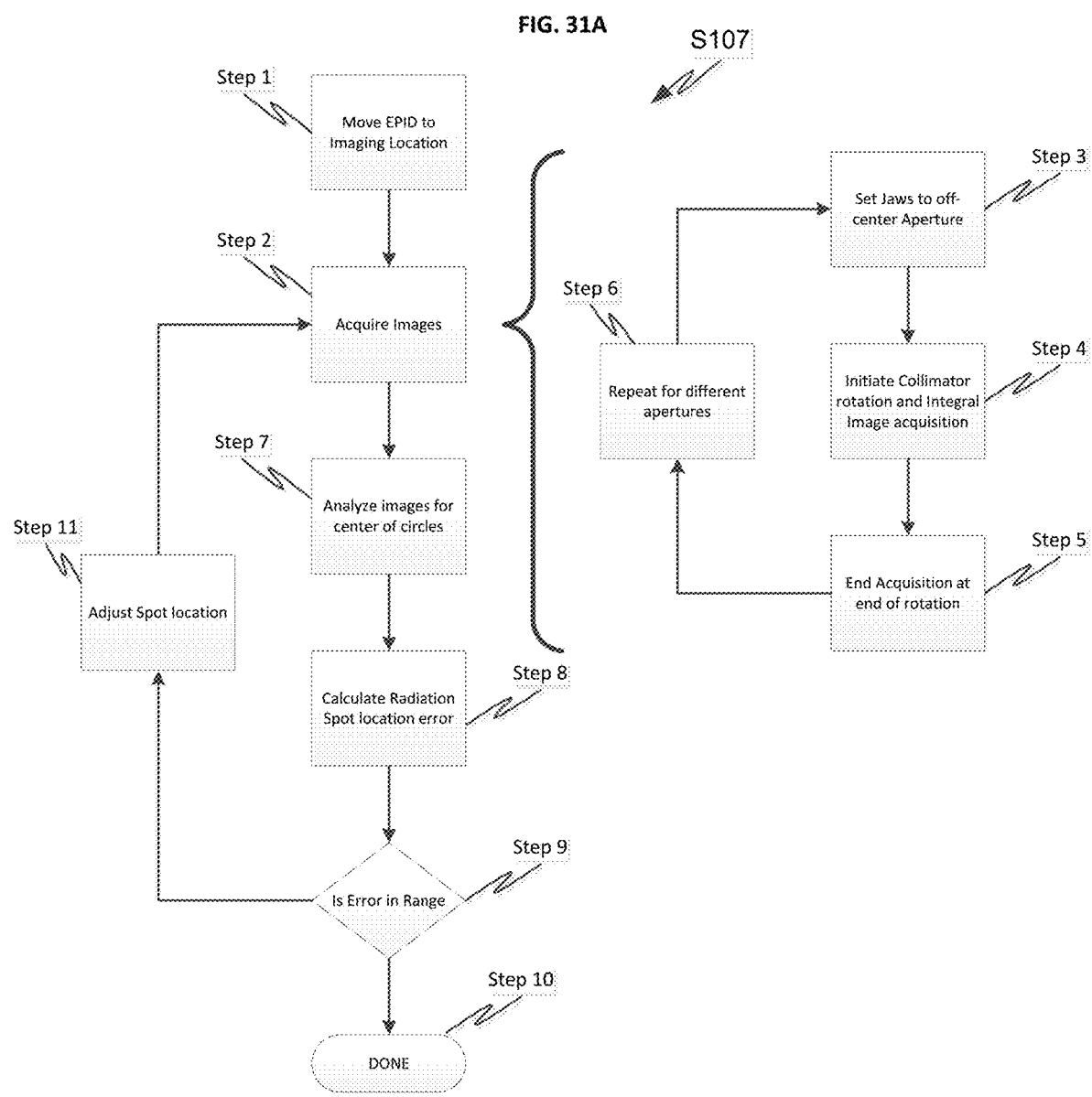

FIG. 33A
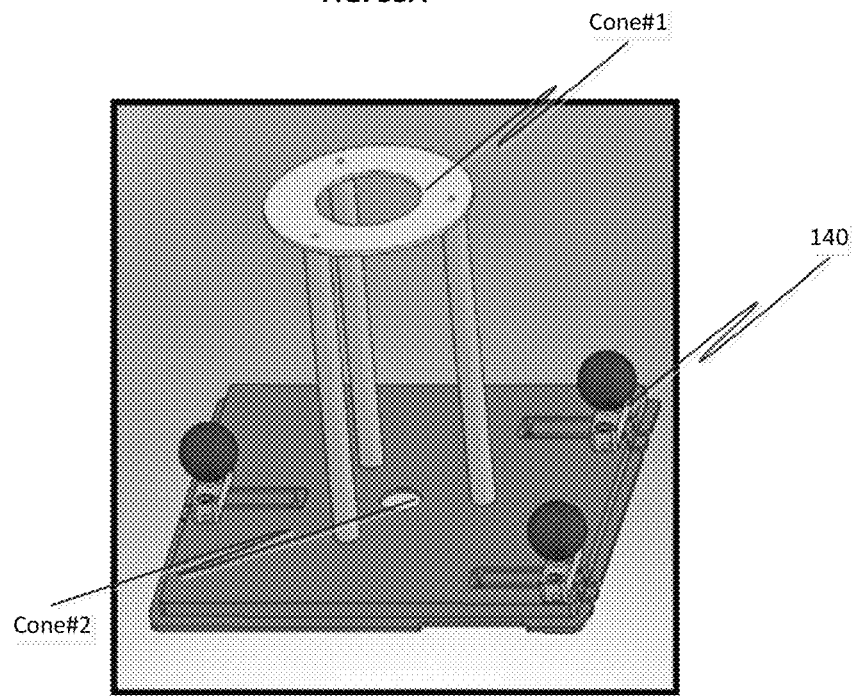
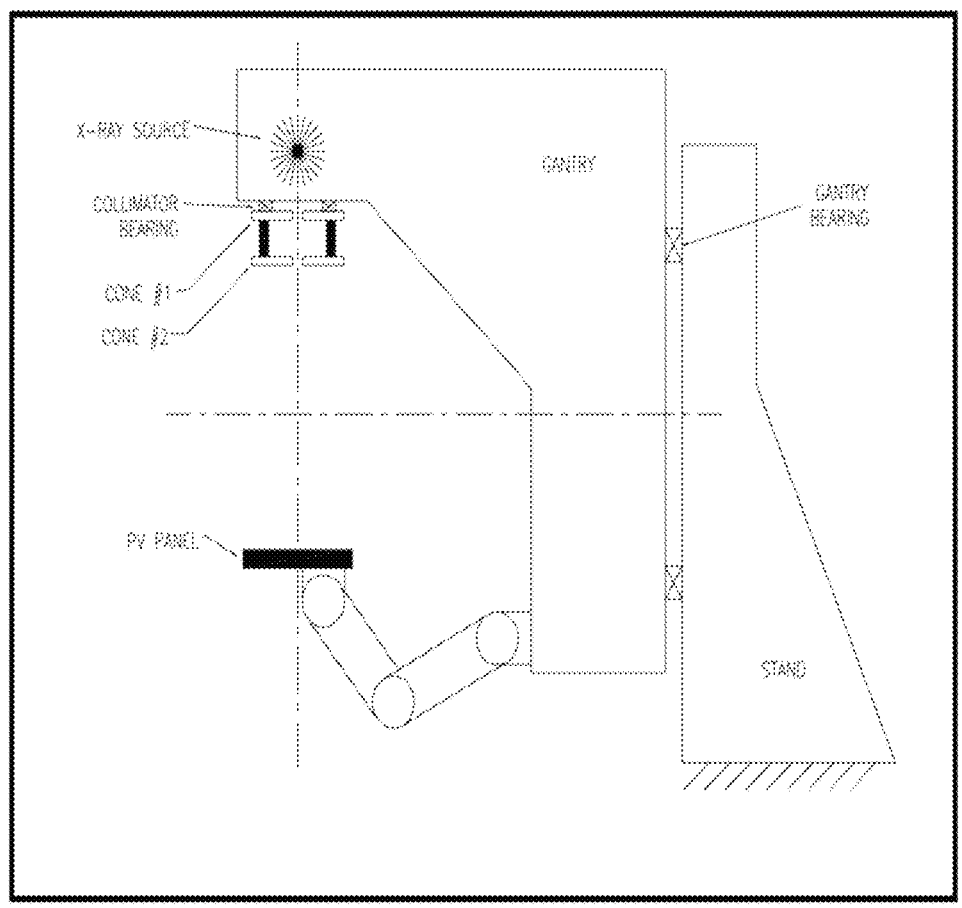
FIG. 33B

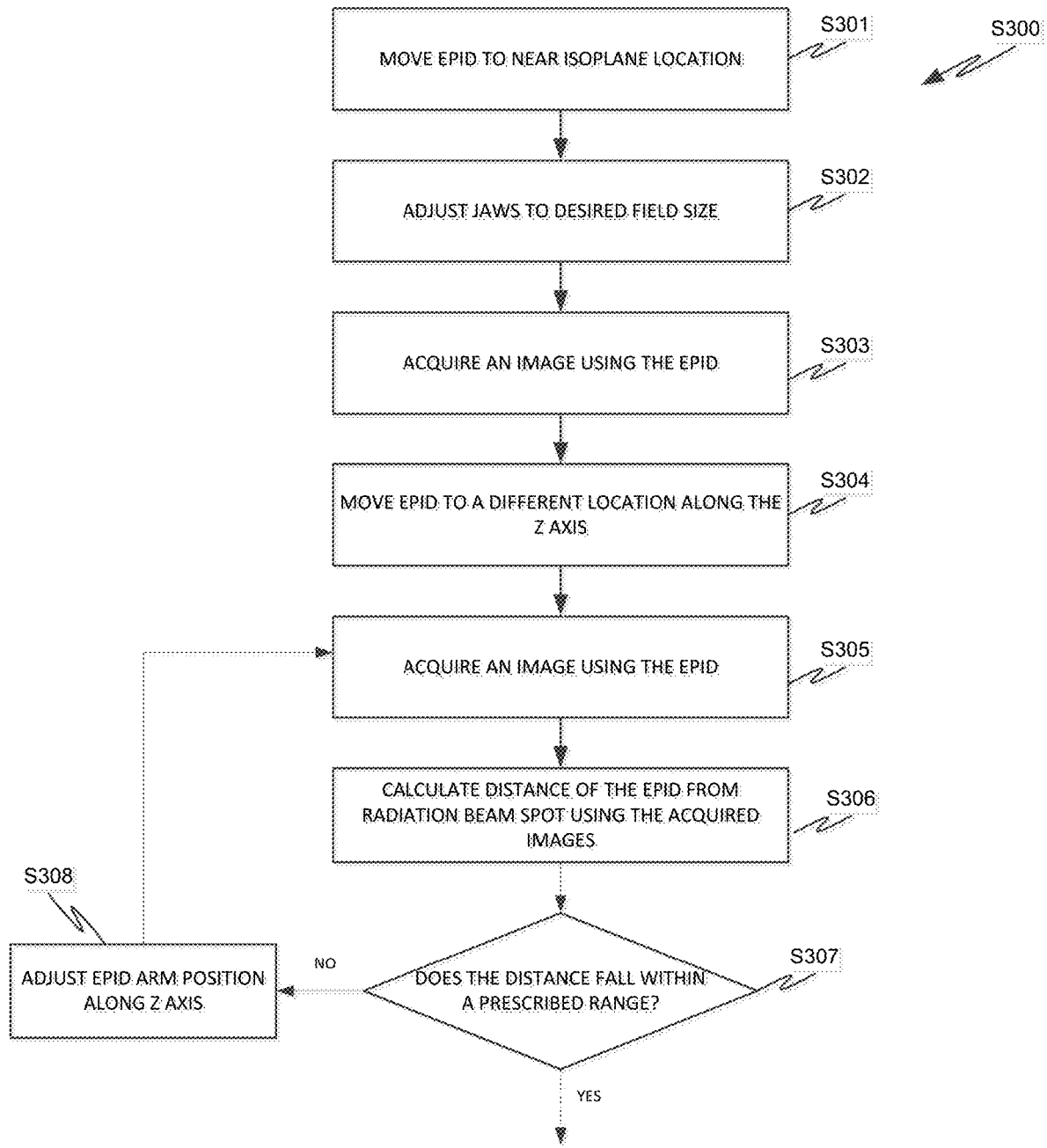

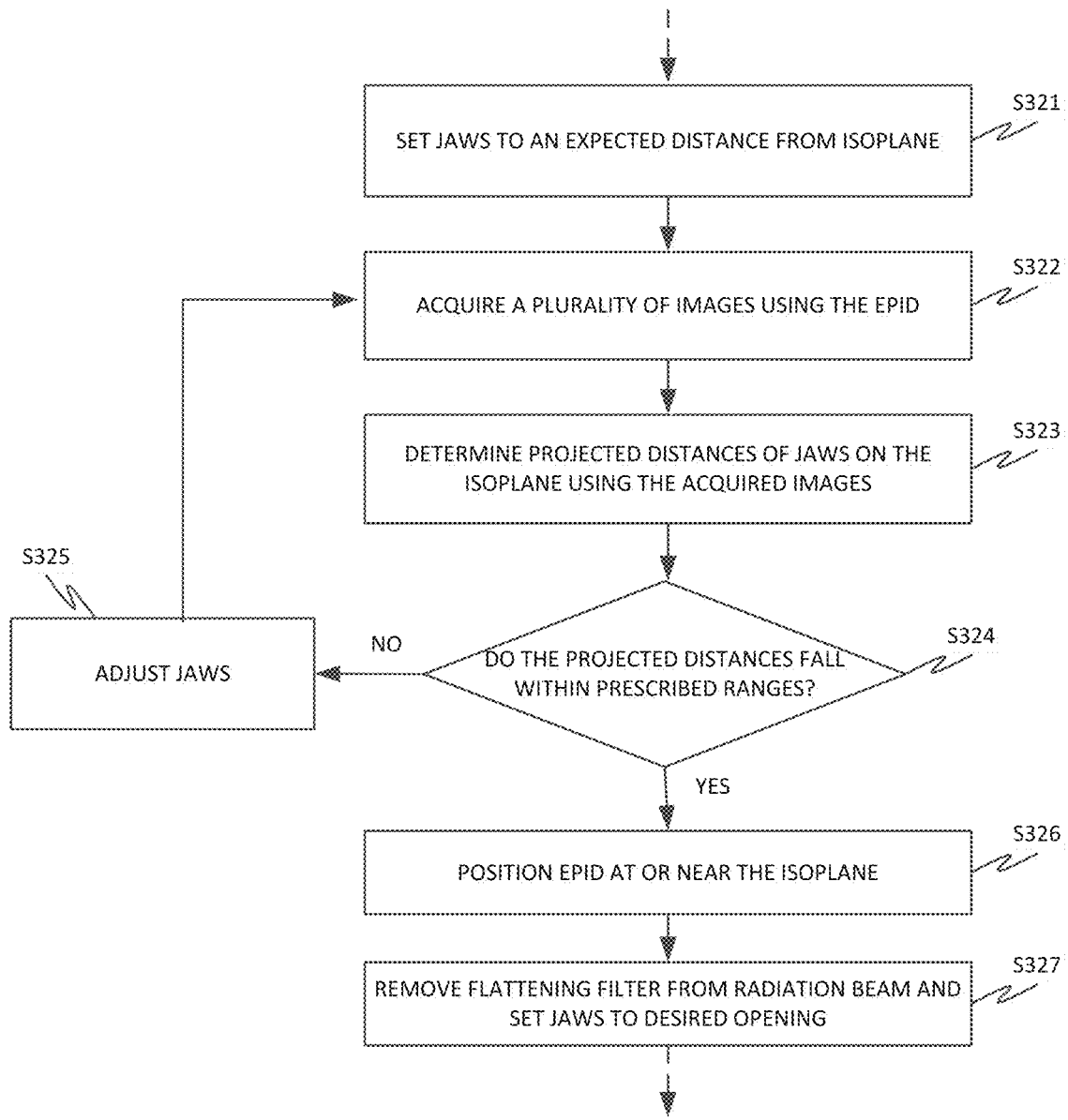

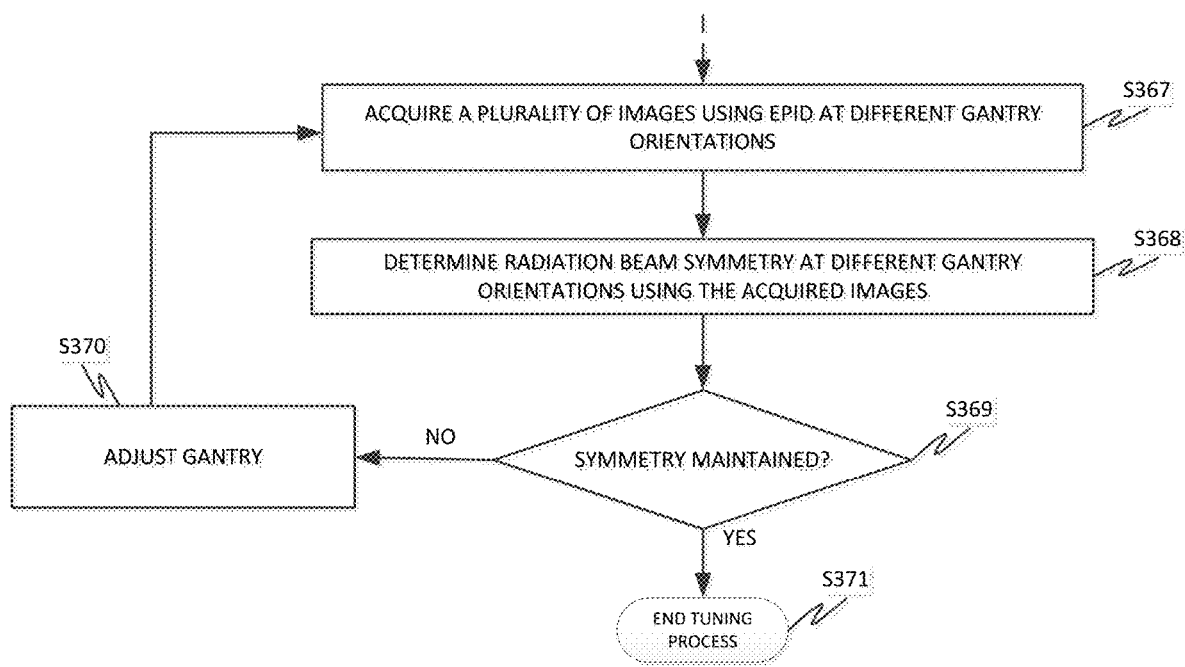

IMAGING-BASED SELF-ADJUSTING RADIATION THERAPY SYSTEMS, DEVICES, AND METHODS

FIELD

The present disclosure relates generally to radiation therapy systems, devices, and methods, and more particularly to methods for automatic tuning, calibration, and verification of radiation therapy systems based on images obtained using electronic portal imaging devices (EPIDs).

BACKGROUND

In radiosurgery or radiotherapy (collectively referred to as radiation treatment) very intense and precisely collimated doses of radiation are delivered to the target region (volume of tumorous tissue) in the body of a patient in order to treat or destroy lesions. Because the radiation dose amount and dose placement need to be sufficiently controlled for accurate patient treatment, the radiation therapy machine itself needs to be properly tuned at the outset (on the production floor), and then continuously monitored through periodic checks, such as, during initial installation or during routine usage of the machine by the customer, to ensure that the system is operating within appropriate and expected parameters and standards, such as, but not limited to, standards prescribed by a nationally recognized regulatory groups such as the American College of Radiology (ACR), the American Association of Physicists in Medicine (AAPM), or the Society for Imaging Informatics in Medicine (SIIM), for example.

Currently available radiation therapy machine tuning, calibration, and verification protocols, however, are slow, inaccurate, require external hardware, and/or rely on subjective human decisions.

SUMMARY

An object of the present invention is to provide imaging-based methods for automatic calibration, tuning, and verification of radiation treatment devices and systems. Since many of the modern radiation treatment devices, such as medical LINACS, are equipped with an electronic portal imaging device (EPID), the present invention provides methods for using the EPID to perform the automatic calibration, tuning, and verification of the radiation treatment systems and devices, and therefore, reduce overall costs, processing, and analysis time, as well as remove operator dependency.

Another object of the present invention is to provide specific procedures and image analysis algorithms for the automatic tuning, calibration, and verification protocols.

The present disclosure provides imaging-based methods for capturing different characteristics of a radiation treatment system using an electronic portal imaging device (EPID) and automatically tuning and/or calibrating the radiation therapy system based on the images acquired by the EPID.

The present disclosure provides image-based quality assurance protocols to test and verify that parameters and characteristics of a radiation treatment device are within predetermined specifications and automatically tune and calibrate the radiation treatment device when the parameters and/or the characteristics are not within the prescribed specifications.

The present disclosure provides using electronic portal imaging devices (EPIDs) for capturing various characteristics and parameters of a radiation treatment device using EPID images, analyzing the various characteristics and parameters captured in the images, and using the information obtained from the images to modify the performance of the radiation therapy system to achieve the desired tuning and calibration of the device.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features.

FIG. 1 illustrates a radiation treatment system according to one or more embodiments of the disclosed subject matter.

FIGS. 2A and 2B illustrate the rotation axes and coordinate frame orientation of the radiation treatment device of FIG. 1.

FIG. 7 illustrates a process flow for calibrating the axes of motion of an electronic portal imaging device according to one or more embodiments of the disclosed subject matter.

FIG. 8 illustrates a geometric layout of an electronic portal imaging device positioned at different heights from a radiation source according one or more embodiments of the disclosed subject matter.

FIG. 9C illustrates an alternative process flow for calibrating the light source of a radiation treatment device according to one or more embodiments of the disclosed subject matter.

FIG. 10 illustrates a geometric layout of a collimator and an electronic portal imaging device positions from a light source according to one or more embodiments of the disclosed subject matter.

FIG. 16 illustrates a process flow for a light source alignment with a radiation source of a radiation treatment device according to one or more embodiments of the disclosed subject matter.

FIG. 17 illustrates a process flow for calibrating collimator jaws according to one or more embodiments of the disclosed subject matter.

FIG. 18 illustrates the geometric layout of a collimator device and an electronic portal imaging device relative to a radiation source according to one or more embodiments of the disclosed subject matter.

FIG. 19 illustrates an alternative process flow for calibrating collimator jaws according to one or more embodiments of the disclosed subject matter.

FIG. 31A illustrates a process flow for calibrating the steering coils of a radiation treatment device according to one or more embodiments of the disclosed subject matter.

FIG. 33A illustrates an alignment mechanism including two cone-shaped through-holes.

FIG. 33B illustrates the alignment mechanism of FIG. 33A installed on the collimator face of a radiation treatment system.

DETAILED DESCRIPTION

Figure 2B:
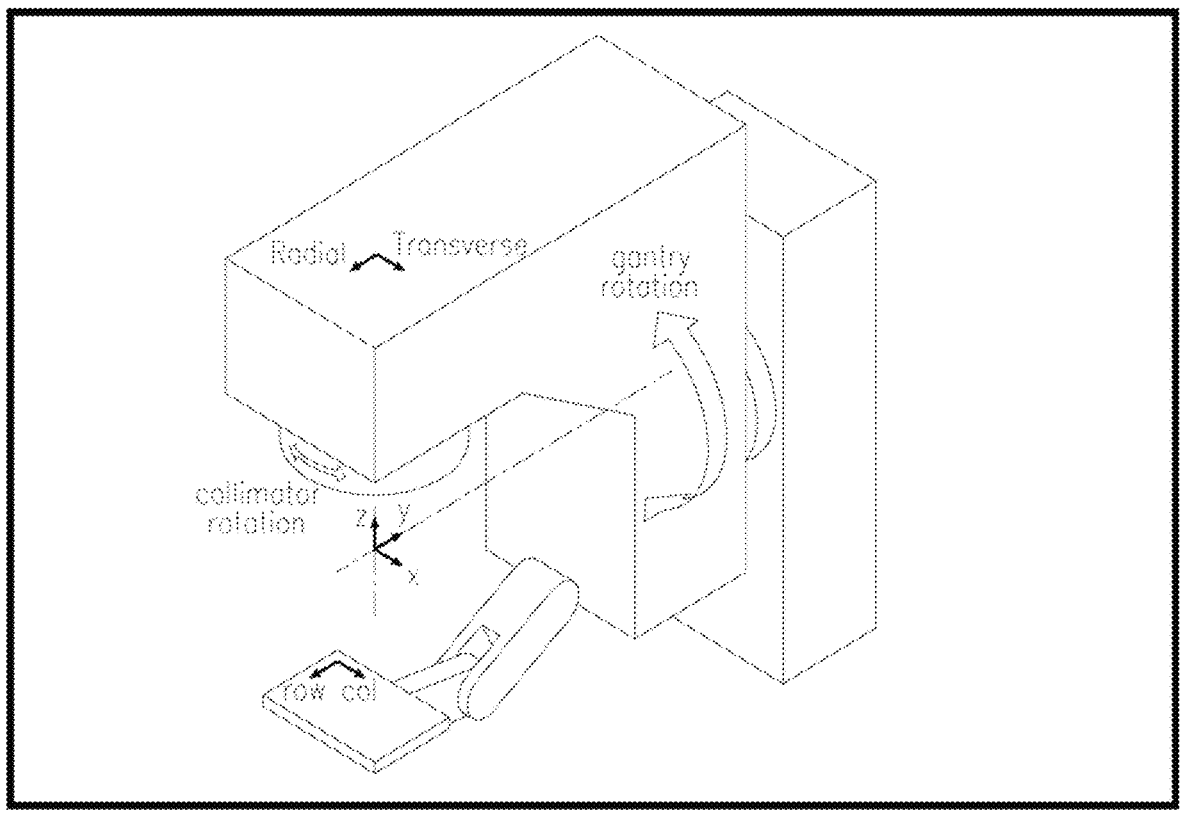

Patients undergoing radiation therapy are typically placed on the treatment platform of a radiation treatment gantry. The radiation beam irradiates a region of interest in the patient, such as a diseased tissue including a tumor or cancerous growth site. When delivering the radiation, a plurality of radiation beams may be directed to the target area of interest from several positions outside the body. The gantry including a radiation source can be rotated to provide the radiation beams from different positions.

The ability to deliver the correct radiation dose to the target area depends on several factors, including exact dose calibration, accurately determined depth dose, off-axis dose characteristics and radiation spot location, as well as knowledge of the precise patient geometry used during irradiation. The factors influencing accuracy of radiation beam delivery are also dependent on the mechanical precision and movements of the machine itself and of the machine and/or treatment accessories such as wedges, blocks, etc.

There are numerous parameters (beam alignment, beam symmetry, beam shape, beam energy, and beam flatness, as well as field shape and width, for example) associated with a radiation therapy system that influence the accuracy of the radiation dose delivered to the patient. Since a given system delivers multiple X-ray and Electron Mode energies, many of these parameters are energy-specific and thus need to be tuned energy by energy. There are also some parameters (e.g., field light location) used for patient setup in order to assure correct setup prior to irradiation. Because these parameters depend on the accurate alignment and placement of various control elements (collimator jaws, steering coils, bend magnet shunt currents, imager moving arm, radiation source, light source, gantry, X-ray flattening filters, electron scattering foils, and internal dosimeters, for example) of the radiation therapy system, these control elements need to be checked and tuned prior to the radiation treatment device being installed and/or used in the radiation treatment facility to ensure that the radiation therapy system is working within expected parameters. Because the mechanical elements affecting these parameters tend to move, the parameters also need to be regularly checked and if a shift is observed from their nominal preset values, the mechanical control elements need to be adjusted and retuned until the outputs of the control elements meet the predefined standards.

The present invention provides a system and method for automatic evaluation of a plurality of parameters of the radiation therapy system using an electronic portal imaging device (EPID) and tuning and/or calibration of the radiation therapy system based on the information contained in the EPID images. The tuning/calibrating may be done on the production floor prior to the installation of the radiation therapy system in a radiation therapy room, or during the initial installation of the radiation therapy system. The present invention also provides a system and method for verifying the parameters of the radiation therapy system using an electronic portal imaging device, and automatically tuning/calibrating the radiation therapy system based on the verifying. The regular checking and the automatic tuning/calibration/retuning of the various mechanical devices of the system ensure that the parameters are maintained within the predetermined quality control specifications.

An exemplary radiation therapy treatment system 100 configured to deliver radiation treatment to a patient is illustrated in FIG. 1. The treatment system 100 can be configured for dual-mode stereotactic or radiation therapy application, namely, the system 100 can be configured to provide photon-based or electron-beam based radiation treatment to a patient 101 positioned on a treatment couch 102. The gantry 106 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment beam source at various rotational and/or axial positions relative to the patient 101 may also be used. The system 100 also includes a treatment couch 102 which can be positioned adjacent to the gantry 106 to place the patient 101 and the target volume within the range of operation of the treatment beam during radiation treatment. The treatment couch 102 may be connected to the rotatable gantry 106 via a communications network and is capable of translating in multiple planes to reposition the patient 101 and the target volume. The treatment couch 102 can have three or more degrees of freedom.

The radiation therapy system 100 includes a radiation treatment device 103, such as, but not limited to, a dual-mode (photon and electron-beam) medical LINAC device configured for stereotactic or radiation therapy application. The radiotherapy device 103 includes a base or support structure 104 supporting the gantry 106. The gantry 106 is supporting an electron beam accelerator module 108 which can include an electron gun 114 for generating electron beams and an accelerator waveguide 115 for accelerating the electron beams from the electron gun 114 toward an X-ray target 118 (when the radiation treatment device 103 operates in a photon mode) or toward an electron beam exit window (not shown), when the radiation treatment device 103 operates in an electron-beam mode. The electron beam exit window allows the electron beam to exit the electron beam accelerator module 108 and enter a LINAC treatment head 110. The accelerating waveguide 115 is usually mounted parallel to the gantry rotation axis, and thus the accelerated electron beam must be bent for it to strike the X-ray target 118 (when device 103 operates in the photon mode) or the exit window (when device 103 operates in an electron-beam mode). An electron beam transport system 116 can include bending magnets, steering coils, trim coils, and a gun cathode heating circuit can be used for bending and steering the accelerated electron beams toward the X-ray target 118 or the exit window. The electron beam transport system 116 can bend an electron beam at 90 degrees, 270 degrees (achromatic bending) and at 112.5 degrees (slalom bending) by adjusting the shunt current applied to the bend magnet from a current source (not shown). When the electron pencil beam hits the X-ray target 118, it generates the clinical photon beams (X-rays). The location at which the X-rays are generated is referred to as the radiation beam spot or radiation source.

In operation, electrons originating in the electron gun 114 are accelerated in the accelerating waveguide 115 to the desired kinetic energy and then brought, in the form of a pencil electron beam, through the beam accelerator module 108 into the LINAC treatment head 110, where the clinical photons, such as X-rays, (when the device 103 operates in the photon mode) or the electron beams (when device 103 operates in the electron-beam mode) are produced. The LINAC treatment head 110 contains several components that influence the production, shaping, localizing, and monitoring of the clinical photon beams, as shown in detail in FIG. 3, or the clinical electron beams, as shown in detail in FIG. 4.

The radiation treatment device 103 also includes a holding structure 113, which could be a retractable robotic, servo controlled arm, holding an imager 112 for acquiring digital images. The imager 112 can be an electronic portal imaging device (EPID). The holding structure 113 is used to position the EPID 112 and allow movement of the EPID 112 vertically (along the Z-axis), laterally (along the X-axis), and longitudinally (along the Y-axis). The EPID 112 can be mounted onto the rotating gantry 106 in opposition to the radiation source, such that the clinical radiation beam, namely the photon or the electron beam, from the LINAC head 110 is received by the EPID 112. The EPID 112 can have a detector surface corresponding to the cross-sectional area of the clinical radiation beam.

In operation, the EPID 112 produces electronic signals providing measurements of the dose of the radiation received at the detector surface at regularly spaced positions over the detector surface. The signals from the EPID 112 are transmitted to a computer processor of the controller 120 where it is converted into a matrix of digital values, the values indicating the dose of radiation at each point of the imager surface. A projection image derived from the matrix of digital values can be displayed on a display of the controller 120.

The controller 120 manages images and related information, such as transforming the data stream from the EPID 112 into a standard video format, the synchronization of the imager 112 and the LINAC treatment head 110 based on the different types of images acquired with the EPID 112, as well as image transfer, frame processing, and image calibration. The controller 120 can also store and display the final image. Controller 120 can include a computer with typical hardware, such as a processor, and an operating system for running various software programs and/or communication applications. The computer can include software programs that operate to communicate with the radiation treatment device 103, which software programs are operable to receive data from external software programs and hardware. The computer can also include any suitable input/output devices adapted to be accessed by medical personnel, as well as input/output (I/O) interfaces, storage devices, memory, keyboard, mouse, monitor, printers, scanner, etc. The computer can also be networked with other computers and radiation therapy systems. Both the radiation therapy device 103 and the controller 120 can communicate with a network as well as a database and servers. The controller 120 can also be configured to transfer medical image related data between different pieces of medical equipment.

The system 100 can also include a plurality of modules containing programmed instructions (e.g., as part of controller 120, or as separate modules within system 100, or integrated into other components of system 100), which instructions cause system 100 to perform different tuning, calibration, and verification functions related to the radiation treatment device 103, as discussed herein, when executed. The system 100 can, for example, include a radiation delivery module operable to instruct the system 100 to deliver a radiation beam with or without the patient 101 or a calibration phantom in place; an image acquisition module operable to instruct the system 100 to acquire one or more radiation and/or light field images using an electronic portal imaging device (EPID); an image processing module operable to instruct the system 100 to receive and process the images from the EPID 112; a determination module operable to instruct the system 100 to determine parameters of the radiation treatment device 103 from the acquired images; one or more evaluation modules operable to instruct the system 100 to evaluate the determined parameters; one or more calibration modules operable to instruct the system 100 to calibrate the radiation treatment device 103 based on the result of the evaluation; and one or more verification modules operable to instruct system 100 to verify the calibrated parameters of the radiation treatment device 103. The modules can be written in C or C++ programming languages, for example. Computer program code for carrying out operations as described herein may also be written in other programming languages.

The system 100 including the EPID 112 integrated with the radiation treatment device 103 allows all image guidance activities, such as, image acquisition, image registration, image interpretation, and machine calibration to occur automatically and remotely. System 100 also allows capture of all data needed for the image acquisition and evaluation (i.e., data relating to gantry, collimator jaws, MLC, light field source, EPID, EPID arm structure, phantom, filters, scattering foils, X-ray target, dose measuring device, beam steering coils, type of image to be acquired, etc.). Image interpretation to determine and evaluate different parameters and characteristics of the radiation treatment device 103 can be performed using different algorithms. The determination of adjustments needed to be made in the control element outputs based on the evaluated parameters and characteristics may also be determined using different algorithms. Once the required adjustments are determined, the necessary tuning and/or calibration and/or verification protocols are automatically sent to the radiation treatment device 103 and the control elements are automatically or manually repositioned/shifted/changed/adjusted until their outputs fall within accepted ranges. FIGS. 2A and 2B illustrate the radiation beam central axis, the gantry rotation axis, the treatment couch rotation axis, the collimator rotation axis, and the isocenter of system 100.

Figure 3:
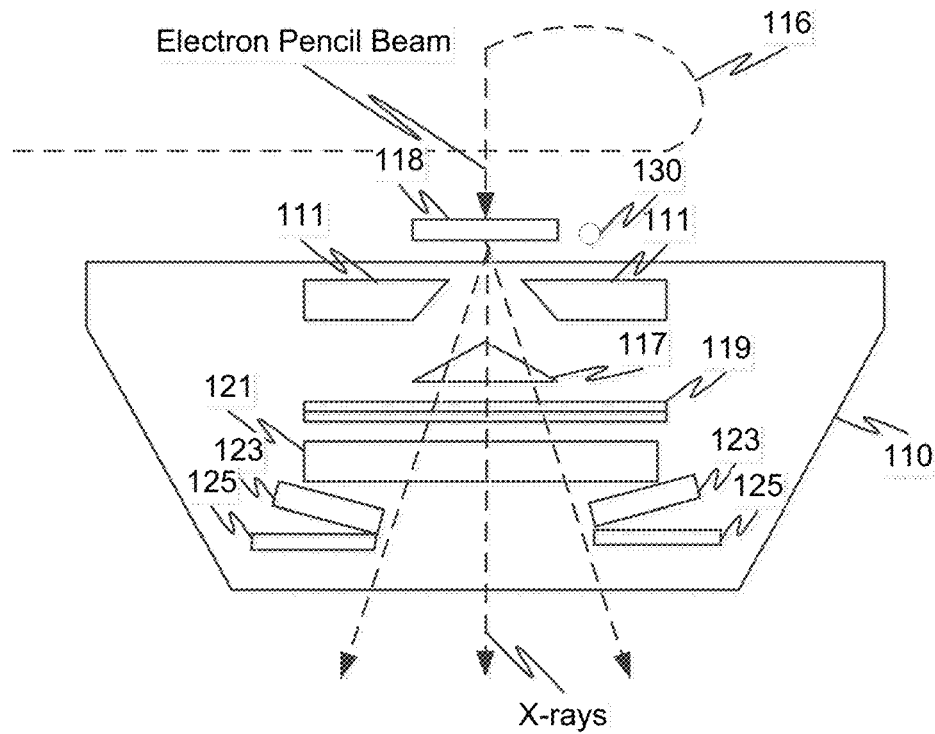
FIG. 3 illustrates a linac treatment head used in a radiation treatment system operating in a photon generation mode.

FIG. 3 illustrates a LINAC treatment head 110 when the device 103 operates in a photon mode. The LINAC treatment head 110 can include one or more retractable X-ray targets 118 where clinical photon beams, such as X-rays, are produced, one or more flattening filters 117, which can be mounted on a rotating carousel or sliding drawer for ease of mechanical positioning of the filters 117 into the electron beam, dual transmission ionization chambers 119, a collimating device (i.e., collimator) including primary collimators 111, adjustable secondary collimators with two upper jaws 121 and two independent lower jaws 123, multileaf collimators (MLC) 125, and a field defining light source 130.

Primary collimators 111 define a maximum circular radiation field, which is then further truncated with the adjustable secondary collimators (121, 123) to produce rectangular and square fields at the LINAC isocenter. The primary collimator 111 defines the largest available circular field size and is a conical opening that can be machined into a tungsten shielding block, for example, with the sides of the conical opening projecting on to edges of the X-ray target 118 on one end of the block, and on to the flattening filters 117 on the other end. The thickness of the shielding block is usually designed to attenuate the average primary X-ray beam intensity to less than 0.1% of the initial value. Any other applicable material besides tungsten can also be used.

The secondary beam defining collimators include four blocks, two forming the upper jaws 121 and two forming the lower jaws 123. They can provide rectangular and square fields at the LINAC isocenter, with sides of the order of few millimeters up to 40 cm. Alternatively, the jaws could be independent asymmetric jaws to provide asymmetric fields, such as one half or three quarter blocked fields in which one or two beam edges are coincident with the beam central axis. The optional multileaf collimators (MLC) 125 can be made of 120 movable leaves with 0.5 cm and/or 1.0 cm leaf width, for example. The MLC can be positioned so as to be parallel with the lower jaws 123. For each beam direction, an optimized intensity profile is realized by sequential delivery of various subfields with optimized shapes and weights. When using MLCs, from one subfield to the next, the leaves may move with the radiation beam on (i.e., dynamic multileaf collimation (DMLC)) or with the radiation beam off (i.e., segmented multi-leaf collimation (SMLC)). Such an MLC system can cover fields up to 40×40 cm$^2$, for example, and can require 120 individually computer controlled motors and control circuits. Miniature versions of the MLC can also be used. For example, miniature MLCs that project 1.5-6 mm leaf widths and up to 10×10 cm$^2$ fields at the LINAC isocenter, could also be used.

The ionization chamber 119 could be a dual transmission ionization chamber used for monitoring the photon radiation beam output as well as the radial and transverse beam flatness. The ionization chamber 119 acts as an internal dosimeter, and can be permanently imbedded into the LINAC treatment head 110 to continuously monitor the radiation beam output. The ionization chamber 119 could also be sealed to make its response independent of ambient temperature and pressure. The ionization chamber 119 can include a primary and a secondary ionization chamber with the primary chamber measuring monitor units (MUs). Typically, the sensitivity of the chamber electrometry circuitry is adjusted in such a way that 1 MU corresponds to a dose of 1cGy delivered in a water of phantom at the depth of dose maximum on the central beam axis when irradiated with a 10×10 cm$^2$ field at a source to surface distance (SSD) of 100 cm. Once the operator preset number of MUs has been reached, the primary ionization chamber circuitry shuts the radiation treatment device 103 down and terminates the dose delivery to the patient 101. Before a new irradiation is initiated, the MU display is reset to zero.

In addition to monitoring the primary dose in MUs, the ionization chamber 119 can also monitor other operating parameters such as the beam energy, flatness and symmetry. Measurements of all of these additional parameters requires that the ionization chamber electrodes of the primary and secondary chambers be divided into several sectors, with the resulting signals used in automatic feedback circuits to steer the electron beam through the accelerating waveguide 115 and the beam transport system 116 and onto the X-ray target 118 or scattering foils 127, thereby ensuring consistent beam flatness and symmetry.

The LINAC treatment head 110 can also include a field defining light source 130 to provide a convenient visual method for correctly positioning the patient 101 for treatment using reference marks. The light source 130 may be mounted inside the collimator and can be positioned at the location of the X-ray target 118 by a rotating carousel or a sliding drawer assembly, or it may be positioned to one side of the collimator axis of rotation with the light reflected by a mirror (shown in FIG. 10). In clinical operations, the light field illuminates an area that coincides with the radiation treatment field on the patient's skin and the alignment of the light field with the skin marks on the patient is used as the final confirmation that the patient 101 is correctly positioned with respect to the radiation beam. It is therefore important that the light field agrees (is congruent) with the radiation field.

Figure 4:
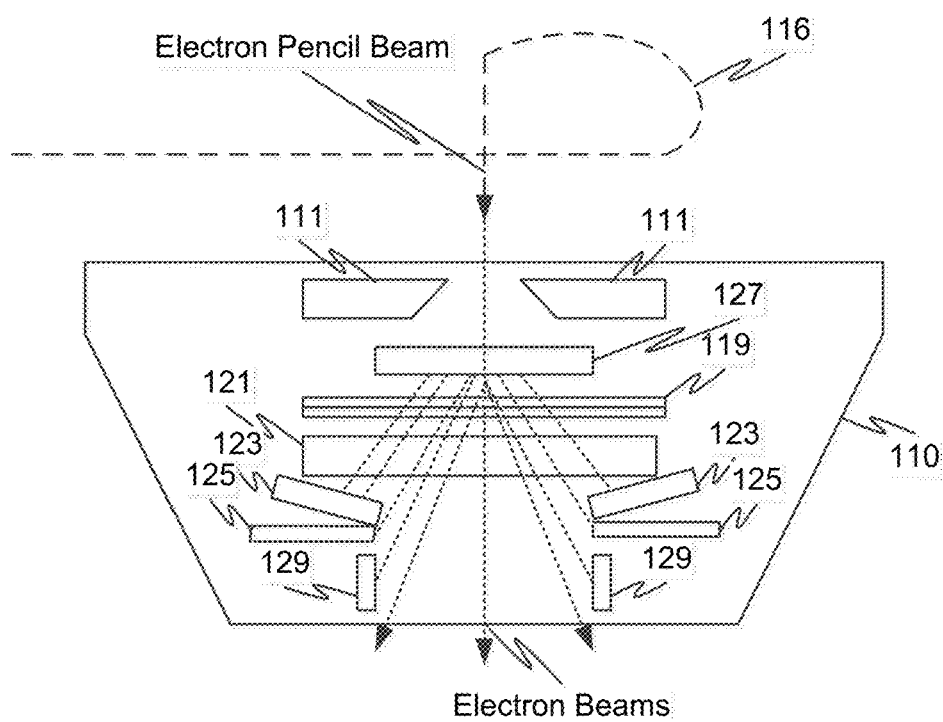
FIG. 4 illustrates a linac treatment head used in a radiation treatment system operating in an electron-beam generation mode.

When the radiation treatment device 103 operates in an electron-beam mode, the LINAC treatment head 110 does not need the X-ray target 118 and the flattening filters 117. FIG. 4 illustrates a LINAC treatment head 110 when the radiation treatment device 103 operates in the electron-beam mode. To activate an electron-beam mode, both the X-ray target 118 and the flattening filters 117 used in the photon mode are removed from the electron pencil beam path. The electron pencil beam exits the beam accelerator module 108 through a thin window (not shown) usually made of beryllium, which minimizes the pencil beam scattering and bremsstrahlung production. To produce clinical electron beams from the electron pencil beams, thin scattering foils 127 of a high atomic number (copper or lead, for example) are positioned into the electron pencil beam at the level of the flattening filters 117 in the X-ray mode. In addition to the primary 111 and secondary collimators 121, 123, the clinical electron beams also rely on electron beam applicators (cones) 129 for beam collimation. The rest of the collimation and beam shaping elements are the same as in the photon-beam mode.

Figure 5A:
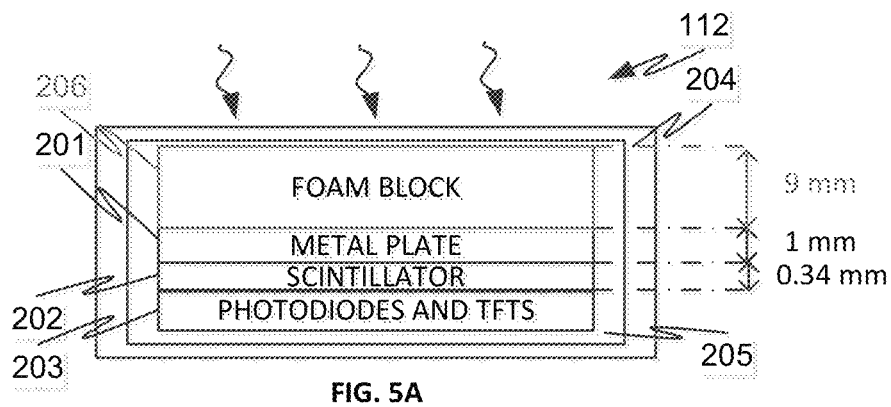
FIGS. 5A-5C illustrate different electronic portal imaging devices according to one or more embodiments of the invention.

FIG. 5A illustrates an exemplary EPID 112. The EPID 112 could be an amorphous silicon type detector panel including a 1 mm copper plate 201 and 9 mm foam block 206, for example, to provide build-up and absorb scattered radiation, and a scintillating phosphor screen 202 made of terbium doped gadolinium oxysulphide, for example, to convert the incident radiation to optical photons. The scintillating screen 202 can have a thickness of 0.34 mm, for example. The EPID 112 can also include a pixel matrix 203 where each pixel is made up of a photodiode and a thin film transistor (TFT), and electronics to read out the charge from the transistor and translate it into an image data. The EPID 112 can also be enclosed in a protective plastic cover 204 with an air gap 205 between the protective cover and the copper plate 201. Alternatively, layers of foam 206 and paper can be included between the protective cover and the copper plate. The protective cover can be about 3 cm, for example, above the effective point of measurement.

Figure 5B:
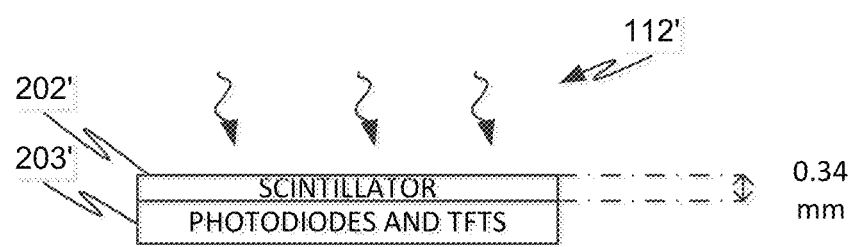
Figure 5C:
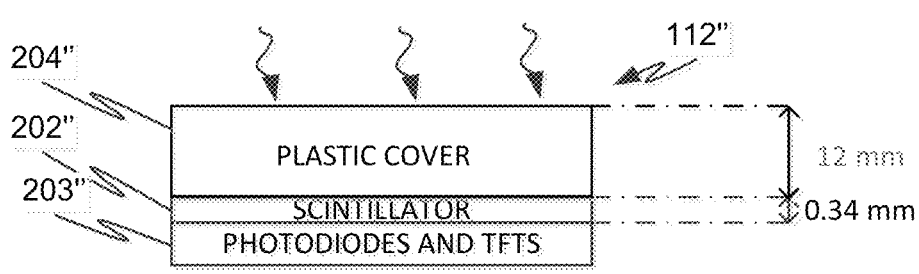

FIGS. 5B-5C illustrate modified EPIDs 112' and 112". Modified EPID 112' exposes the scintillator 202'directly to the radiation beam, meaning that the protective plastic cover 204, the layers of paper and foam 206, and the metal plate 201 are removed from the EPID 112' to expose the scintillator 201' to the external environment and the clinical radiation. The EPID 112' also includes a pixel matrix 203' where each pixel is made up of a photodiode and a thin film transistor (TFT), and electronics to read out the charge from the transistor and translate it into an image data.

FIG. 5C illustrates an alternative modified EPID 112", where the exposed scintillator 202" is covered with an optical grade plastic cover 204" to hold the scintillator 202" in place without degrading image quality. The optical grade plastic cover 204" can have a thickness that is equivalent to the thickness of the removed elements, meaning the total thickness of the plastic cover 204, the copper plate 201, and/or the gap or paper and foam layers 206. The plastic over 204" can be integrated with the EPID 112" or can be attached to a movable arm structure that can position the plastic cover 204" above the scintillator 202" to cover it, or can move the plastic cover 204" away from the scintillator 202" to expose the scintillator to the radiation beam. The EPID 112" also includes a pixel matrix 203" where each pixel is made up of a photodiode and a thin film transistor (TFT), and electronics to read out the charge from the transistor and translate it into an image data.

The EPID 112 can also be fashioned such that the layers of paper and foam 206, and the metal plate 201 are removable and exchangeable with an optical grade plastic cover 204" such that a single EPID 112 can convert to any of these modified states 112' and 112".

Calibration Process

Figure 6:
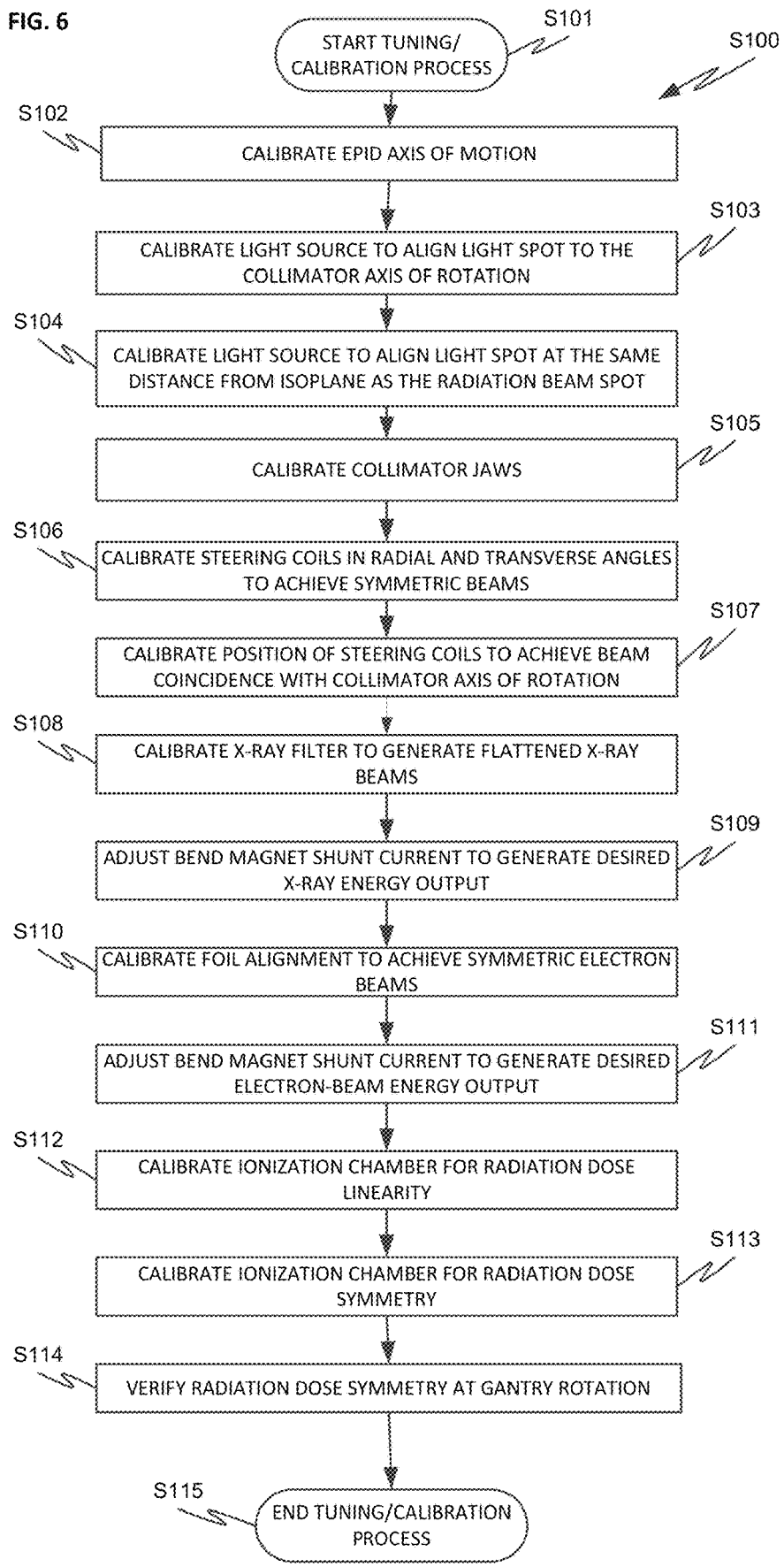
FIG. 6 illustrates an imaging-based calibration process for a radiation treatment device according to one or more embodiments of the disclosed subject matter.

An exemplary automatic tuning/calibration process S100 by which the system 100 is tuned/calibrated with an EPID to operate within expected parameters is shown in FIG. 6. The process S100 includes measuring, using an electronic portal imaging device, a plurality of parameters/characteristics of the radiation therapy system 100, evaluating the measured parameters/characteristics against predetermined standards, and tuning/calibrating the control elements of the system 100 based on the results of the evaluation so as to ensure that the dosimetric characteristics and the mechanical and geometric integrity of the radiation treatment device 103 is maintained. Process S100 only shows the steps which use the EPID. However, there are many more steps for fully tuning a system 100.

Process S100 includes a plurality of calibration tasks which could be fully or partially automatically performed during the initial tuning of the radiation treatment device 103 using an electronic portal imaging device EPID (112, 112', 112"). The process S100 includes calibration/tuning/adjustment of one or more of the: EPID's axis of motion (S102), light source (S103, S104), collimator jaws (S105), steering coils (S106, S107), X-ray filters (S108), bend magnet shunt current value (S109, S111), scattering foil (S110), ionization chamber (S112, S113), and gantry (S114).

The starting of the tuning/calibration process S100 can be initiated at the controller 120 in Step S101, or via a second computer adapted to communicate with controller 120 to execute the calibration tests. The individual calibration/tuning/adjustment steps are described in detail below.

1. Imager Arm Calibration (Step S102)

As part of the radiation treatment setup, it is important to calibrate the axes of motion of the imager arm 113 with respect to the radiation treatment device 103. A properly calibrated arm structure 113 allows for the accurate positioning of the EPID 112 relative to the isoplane (isoplane being the plane defined at a particular distance SDD of 100 cm, for example, from the radiation beam spot or radiation source). The arm structure 113 has three degrees of freedom, namely it can move along the X, Y, and Z axis, the X and Y axes being along the isoplane and the Z axis being the axis along which the arm structure 113 moves toward and away from the radiation beam spot. Using EPID imaging, in the calibration process described below, all three axes of motion can be automatically and objectively calibrated.

a. Calibration Process

The prerequisite for the accurate imager arm calibration process is that the EPID pixels are homogeneous and of known constant geometry. The EPID 112 so can be operated in various image acquisition modes that are a combination of beam energy, repetition rate, and scanning modes, including but not limited to, acquisition of a dark-field image and a flood-field image, the dark-field image, which provides information about background noise, being obtained by taking a base reading for each pixel in the absence of the radiation (or light in the case of an exposed/modified EPID 112' or 112"). The EPID can also be operated to acquire alternating image pairs (i.e., acquiring successive pairs of dark field/flood field images (described in detail below)).

The particular steps involved in the imager motion calibration process S102 are illustrated in FIG. 7. The first step (Step 1) in the calibration process S102 is to calibrate the center location of the EPID 112 with respect to the system 103 coordinate frame (FIG. 2B). This is done by determining the projection of the radiation beam center location on the EPID 112. There are multiple methods to determine the center of the radiation beam as projected onto the imager panel 112, the approach taken depending on the stage at which the tuning process S100 is, as well as the desired accuracy. For example:

If S102 occurs prior to step S107, namely, prior to the alignment of the radiation beam with the axis of rotation of the collimator, an error may be introduced into the imager arm calibration process S102 due to the radiation beam spot not being projected correctly onto the EPID 112. Therefore, if S102 occurs prior to S107, it may be desirable to use the Step 1 calibration process which accounts for this error. Through analysis of a particular geometry, it may also be determined that the size of error is acceptable and does not need to be accounted for.

If S102 occurs prior to step S105, namely, prior to the collimator jaws being calibrated, the error introduced into the imager arm calibration process S102 for a method which relies upon known jaw positions for finding the projected radiation beam spot onto the EPID 112 may not be minimal. Therefore, when S102 occurs prior to S105, a method for locating the radiation beam center location on the EPID 112 which does not rely upon known jaw positions is preferred. For such a method, it is assumed that S107 has been completed or the error of the radiation spot not being on the collimator axis of rotation is insignificant. This method does not require S103 to be completed.

To determine the projected radiation beam center location on the EPID 112 for this situation, the upper jaws 121, lower jaws 123, the MLC 125, and the EPID 112 are first moved to known imaging locations. Then, the upper and lower jaws, 121, 123, are positioned so as to create a small off-center field. This is done by moving the upper jaws 121 off-center while the lower jaws 123 are positioned symmetrically to generate a small 1-2 cm square or rectangular radiation field through the collimator aperture. Once the collimator jaws are in place, collimator rotation and image acquisition are initiated simultaneously. The image acquisition technique used is the "integral" image acquisition mode (also called dosimetry mode). Using the integral acquisition mode, while the collimator is rotated as close to 360 degrees as possible, images are taken using the EPID 112. The EPID 112 continuously captures the incident radiation (at a defined rate) and creates a single aggregate (integrated) image from the start of the image acquisition to the end of the image acquisition process. By integrating the resulting images, a characteristic donut shaped image is created. In the donut shaped image, the inner and outer rings are defined by the upper jaw 121 faces. Since the collimator cannot go a full 360 degrees, the image acquisition is repeated, but with the upper jaws 121 moved to an opposite offset location to generate a mirrored second image. Two mirror images are taken because with a less than 360 degree rotation there will be a missing arc segment resulting in an off-center error when determining the best fit center location. The pair of images so obtained is then analyzed to find the exact center of the donut using a precise edge-detection method with a best-fit circle algorithm as illustrated in detail in FIGS. 20-24.

Prior to applying the edge-detection algorithm, if desired, an image filter can be applied to reduce errors caused by image irregularities such as noise or image artifacts. When an image filter is applied, each pixel is reassigned either the value of the average of a given number of pixels around it in a two-dimensional (2D) or three-dimensional (3D) space (i.e., mean value) or the value of the median pixel (i.e., median value). A value weighting factor can be used in the averaging to achieve desired effects (Gaussian filtering).

In general, the precise edge-detection method applied to find the exact center of the donut includes analyzing the image to create a linear sequence of pixels and respective values to generate a profile from which the precise location of a percentile threshold can be determined. An edge detection method to be applied here is shown in FIGS. 20-24, and described in detail below. The prerequisite for the edge-detection method is that the general location of the edge is already known. The general location of the edge can be determined using any one of multiple methods, such as, but not limited to, a first pass with a general purpose edge-detection method followed by a best-fit line algorithm, or a Hough Transform technique fitting to a rectangle. The general edge location can also be determined from the known machine axis position for Jaws, MLC, Collimator rotation etc.

Once the general location of the edge is known, for a given edge, estimated edge points are generated. The estimated value for each edge point is taken from prior knowledge, such as, but not limited to, information regarding the radiation treatment device 103, or from a rough full-image edge-detection and line regression estimate using Sobel, Robert's cross, Laplacian of Gaussian, or Canny's transformations and straight regression or Hough's transform.

After the estimated edge points are generated, the exact edge profile for each point is created. This involves identifying a start point $p_0$ and an end point $p_1$ orthogonal to an expected edge line. Since the offset distance from the estimated edge point is system dependent, the certainty of the estimated point, the size of the penumbra, the potentially interfering geometry, and the homogony of dark and light areas need also be considered. Then, using a normalized line method, the start and end points are connected and, at given increments, steps are taken from 0 to 1 using the following normalized line equations:

$X(i)=(X2-X1)*i+X1$ $Y(i)=(Y2-Y1)*i+Y1$, where $i$ is the step from 0 to 1.

At each point between the start point $p_0$ and the end point $p_1$, the actual pixel value can be interpolated since it will typically be between pixel centers. There are numerous interpolation methods that can be used to determine the pixel value, such as, but not limited to, linear, bilinear, Bezier, and polynomial methods, all of which being incorporated herein by reference. Using a bilinear interpolation method, wherein four pixels surrounding each step location is taken into consideration, a penumbra profile is next generated. This penumbra profile is the result of the linear interpolated results along the normal line.

After the edge profile is generated, the exact edge point per profile is next calculated. Determination of an edge point includes analyzing the edge profile to determine the threshold of interest. A search is done to find the closest points above (i.e., maximum) and below (i.e., minimum) the threshold value and then direct linear interpolation is applied between these points to calculate a precise coordinate. Determination of the exact threshold is system dependent. In case of radiation delivery, a threshold of 50%, for example, can be selected. The determination of the minimum value (i.e., point below threshold value) can be done many different ways, including, but not limited to, selecting the minimum value in the profile or averaging of the first few values at the start or end points, or averaging a sample of the entire image area outside of the exposed area. Determination of the maximum value (i.e., point above threshold value) can be done in many different ways, including, but not limited to, selecting the maximum value in the profile, or averaging of the first few values at the start or end points, or averaging a given number of pixels at the center of the exposed area (i.e., center of the radiation field).

Next, the best-fit edge is determined to population of edge points. The best-fit line is calculated by analyzing all edge points found along an expected line region. Any of the available the best-fit algorithms can be applied to determine the best-fit line. Alternatively, if the edge profile is known to be arced, a best-fit arc or best-fit circle algorithm can be used with the population of edge points.

Using this precise edge-detection method with a best-fit circle calculation will determine the donut center location. The accuracy of this approach depends on the arc and radius of the donut, the distance of the radiation spot from the collimator rotation axis, and the distance of the radiation limiting device (collimator jaws) from the radiation spot (the greater the distance the less impact off-center radiation spot has). Another factor is the unknown scaling factor of the pixel size between EPID 112 and projection to isoplane, although this factor will be very small in magnitude.

Alternatively, a double donut approach, as described in detail under the calibration step of S107 can be taken to improve accuracy by 0.1 mm. This accuracy also depends on the arc and radius of donut (the closer the arc is to 360 degrees, the less improvement comes from a double donut).

Using the precise edge-detection method with a best-fit circle calculation will determine the donut center location for each of the two donut images. The radiation spot location projected onto the EPID 112 is the geometric average of the two donut centers. If for a given system the errors associated with not having completed step S107 are significant, a full 4-image pairs (donuts) can be generated to calculate a precise projected center location. Such a method is fully explained in step S107. Other edge detection and best fit algorithms can also be used, such as those disclosed in U.S. application Ser. No. 14/040,591, filed Sep. 27, 2013, entitled "Methods for Image Processing", assigned to Varian Medical Systems Inc., incorporated herein by reference in its entirety.

If S102 occurs after the collimator jaws have been calibrated (i.e., after S105), and if either S107 has been completed, or if the error associated with not having completed S107 is considered insignificant, then the following method can be employed. The radiation beam center on the EPID 112 can be calculated by first creating a square field about the beam centerline using the collimator jaws, and then analyzing the square field using an edge-detection method, such as the one described above and in FIGS. 20-24, together with a best-fit rectangle algorithm to determine the precise location of the beam center location on the EPID 112. The radiation beam center can also be calculated using the method disclosed in U.S. application Ser. No. 14/040,202, filed Sep. 27, 2013, entitled "Systems and Methods for Processing Images to Measure Multi-Leaf Collimator, Collimator Jaw, and Collimator Performance", assigned to Varian Medical Systems Inc., incorporated herein by reference in its entirety.

After the location of the projected radiation beam center on the EPID 112 is determined, the calibration process S102 moves on to Step 2 where the X and Y axes are calibrated. To calibrate the X and Y axes, using the calculated beam center location in Step 1, the X and Y origins can be set with respect to the specific pixel coordinates of the center location, since it is typical to calibrate the geometric center pixel with 0, 0 coordinates.

Next, the Z axis is calibrated in Step 3. To calibrate the Z axis, first the EPID 112 is moved to a first vertical location (Height 1), as shown in FIG. 8, and an image using the EPID 112 is acquired at this location. The first vertical location (Height 1) could be a known location, such as the location where the isoplane is expected to be. However, the first vertical location need not be a known location. The first image is acquired using a normal flood field/dark field adjusted technique. Then, in Step 4, the EPID 112 is moved to a second vertical position (Height 2) and a second EPID image is acquired. The second image can also be taken using a normal flood field/dark field adjusted technique. The field size can be set to a size small enough so that there is an unexposed border in the image obtained at the second vertical location. Next, in Step 5, the actual first vertical location can be calculated using equation 1, which is based on the geometric layout of the EPID 112 relative to the radiation source, as shown in FIG. 8:

$$Z = \frac{\partial Z}{\frac{D_B}{D_A} - 1} \qquad \text{Eq. 1}$$

where, Z is the distance of the EPID 112 from the radiation source along the Z axis; $\partial Z$ is the amount by which the EPID 112 was moved between the two locations; $D_A$ is the size of the radiation field at the first location of the EPID 112; and $D_B$ is the size of the radiation field at the second location of the EPID 112.

To calibrate the Z-axis, in Step 6, the EPID 112 can be moved to the calculated location Z of the EPID 112. Alternatively, the offset between current position and actual position can be used to adjust the calibration parameters directly. The calibration process can be terminated after Step 6.

Optionally, the accuracy of the calibration along the X, Y, and Z axes can be verified in Step 7. To verify the accuracy of the X and Y axes calibration, after the EPID 112 was moved to the calculated location Z, a first image is acquired using the EPID. Then, the EPID 112 is moved along the X or the Y axis by a known distance, and a second image is taken. Any field size can be used to generate the first and second images. Using the edge-detection and best-fit line (circle) algorithms described above, the actual distance by which the EPID 112 has been moved can be calculated and compared against the commanded move. Any discrepancy in the desired versus actual move can be used for calibration. For example, if there is a mixture of moves in the X and Y directions when only a move in the X direction is desired, the motion coordinates can be re-aligned using the calibration software so that accurate moves in the X and Y directions can be made.

To verify the accuracy of the Z axis calibration, a first image is taken at a first location along the Z axis, then the EPID 112 is moved to a second location along the Z axis and a second image is taken. Using the edge-detection and best fit line/circle algorithms described above, the field sizes and the centers of the fields can be determined from the acquired images. By comparing the field sizes in the images, it can be determined whether an accurate move along the Z axis was made by the EPID 112. By comparing the centers of the fields, it can also be determined whether there is any X or Y component in the move, and if there is either an X or Y component in the move along the Z axis, it can be included in the motion calibration algorithm to ensure that the EPID's arms structure 113 is correctly aligned.

To increase the accuracy of the Z axis calibration procedure, the Z-calibration method can be augmented by taking images at more than two locations. By taking a third or fourth image, the error in relative Z motion can be diminished and the error in field size determination can also be diminished.

Another way to increase the accuracy of the Z axis calibration procedure is to iterate the 2-height image acquisition method. In some cases with multi-link actuators, the relative move between heights can have an error before a calibration has not been completed. Iterating will increase the accuracy of the relative move and thus the overall calibration.

Although the imager arm structure calibration procedure S102 was described as using radiation beams (i.e., X-rays) as the radiation fields, and EPID 112 as the imager capturing the radiation beams, in an alternative embodiment, the calibration procedure S102 can be implemented using light from the light source 130 and one of the modified EPIDs 112' and 112" as the imager capturing the light fields.

2. Light Spot to Collimator Axis of Rotation Calibration (Step S103)

For attaining proper positioning of the patient 101 in the radiation field, the light source 130, which is used as a radiation field positioning aid, must be adjusted so that the light spot is at the same virtual point as the radiation source, and so that the light field remains on the axis of collimator rotation. In addition, the virtual light spot needs to be located the same distance from the patient as the radiation spot. In this manner, the light field will define the geometric boundaries of the radiation field and will allow the patient 101 to be positioned correctly on the treatment couch 102 prior to radiation treatment. Therefore, in S103, the light source 130 is calibrated to align the light spot to the collimator axis of rotation, and in S104, the light source is calibrated to align the light spot at the same distance from the isoplane as the radiation beam spot.

a. Calibration Process

Figure 9A:
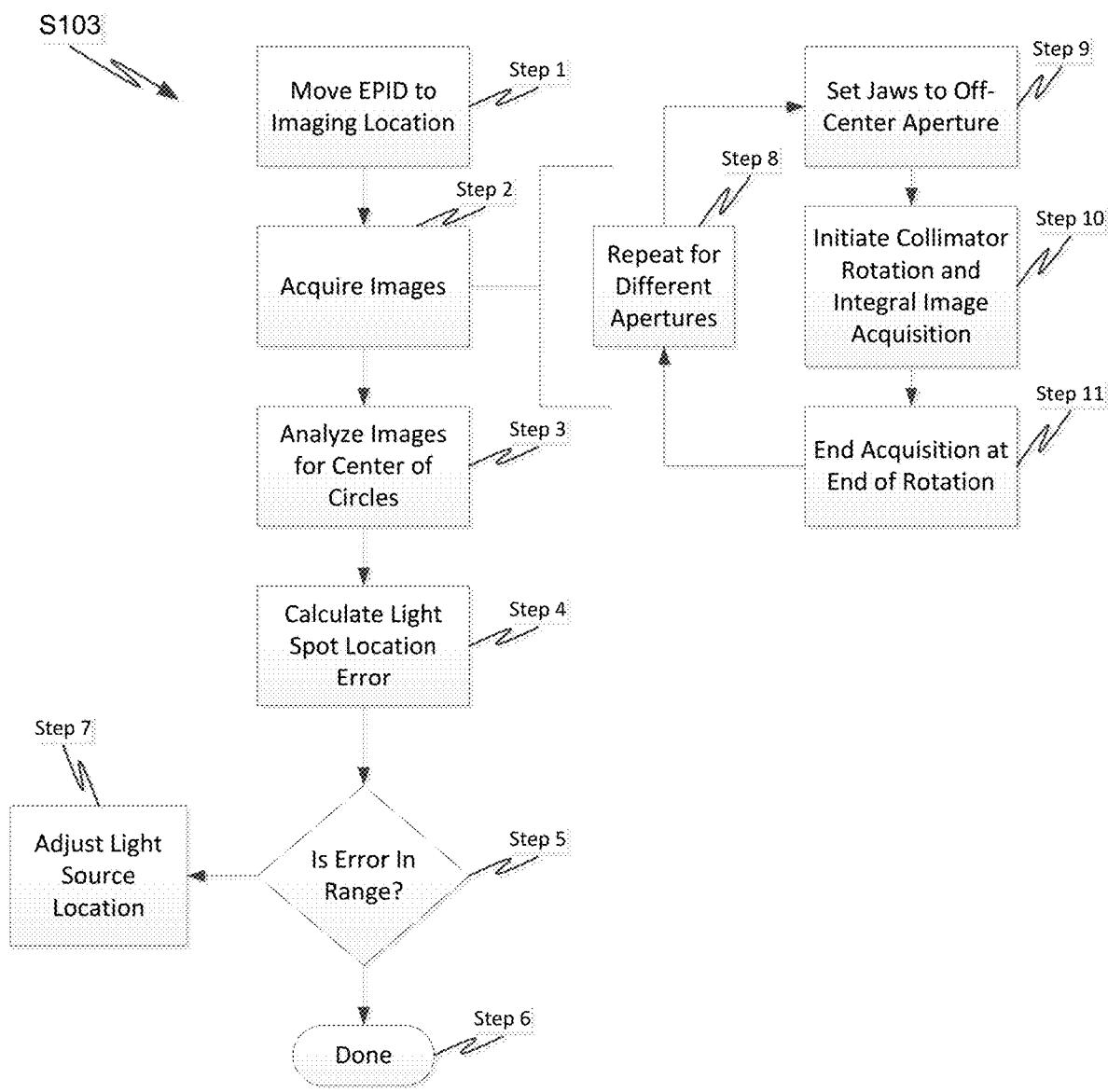
FIG. 9A illustrates a process flow for calibrating the light source of a radiation treatment device according to one or more embodiments of the disclosed subject matter.

The light field calibration process S103 is illustrated in FIG. 9A. The prerequisites for an accurate light field calibration process S103 is that a light-sensitive modified EPID 112' or 112" is used; the modified EPID 112' or 112" is at a known distance from the light source 130; the modified EPID 112' or 112" pixels are homogeneous and of known constant geometry; and that the light source 130 is located so as to be independent from the rotation of the collimator.

In Step 1 of the calibration process S103, the modified EPID 112' or 112" is moved to a known distance from the light source 130. This distance could be, but is not limited to the SDD distance of 100 cm or 170 cm from the light source 130. The greater the distance, the better the alignment accuracy. The upper jaws 121, lower jaws 123, as well as the MLC 125, are at known fixed distances $D_{ujaw}$, $D_{ljaw}$, and $D_{mlc}$, respectively, from the light source 130. The geometric layout of the collimator jaws 121, 123, 125 and EPID 112' or EPID 112" positions relative to the radiation source is illustrated in FIG. 10. Once the EPID 112' or 112" is positioned at the initial imaging locations, in Step 2, four images (i.e., two pairs) are acquired using the EPID 112' or 112". The images are taken in pairs.

Figure 11:
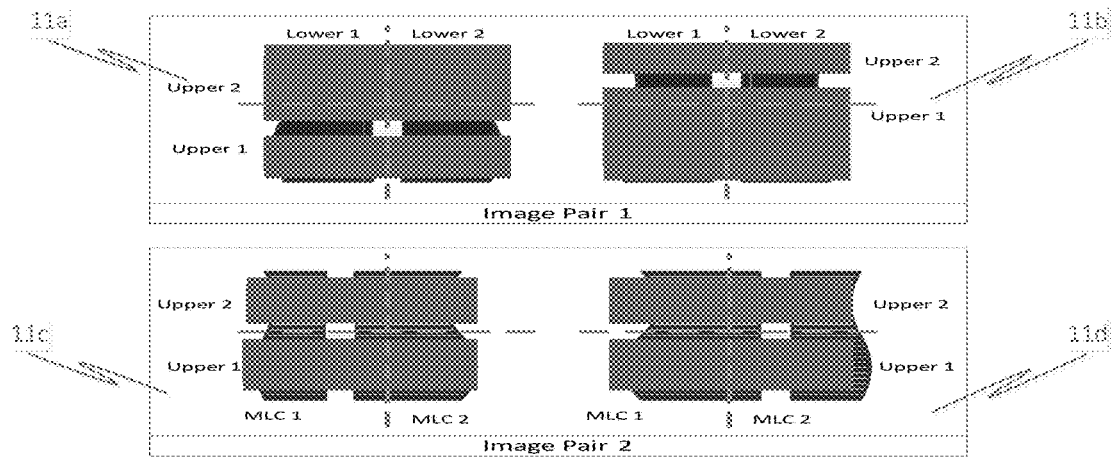
FIG. 11 illustrates collimator positions to generate image pairs according to one or more embodiments of the disclosed subject matter.

The first pair of images is taken by first positioning, in Step 3, the upper jaws 121 (Upper 1, Upper 2) and the lower jaws 123 (Lower 1 and Lower 2) as shown in FIG. 11a, to create a small off-center field. To create the small off-center field, the upper jaws 121 are moved off-center while the lower jaws 123 are positioned symmetrically to generate a small (1-2 cm, for example) square or rectangular light field through the exposed collimator aperture. After the upper and lower jaws are in place, the collimator rotation and the image acquisition is initiated simultaneously in Step 4. With all room and peripheral lights off, while the collimator is rotated as close to 360 degrees as possible, images are taken using the EPID 112' or 112". The sensitivity of the modified EPID 112' or 112" to ambient light can be reduced by including a light filter in front of the EPID 112' or 112". The light filter can be made so as to be transparent to the light that comes only from the direction of the light source 130. The light that comes from any other direction will thus be absorbed by the light filter.

Figure 12:
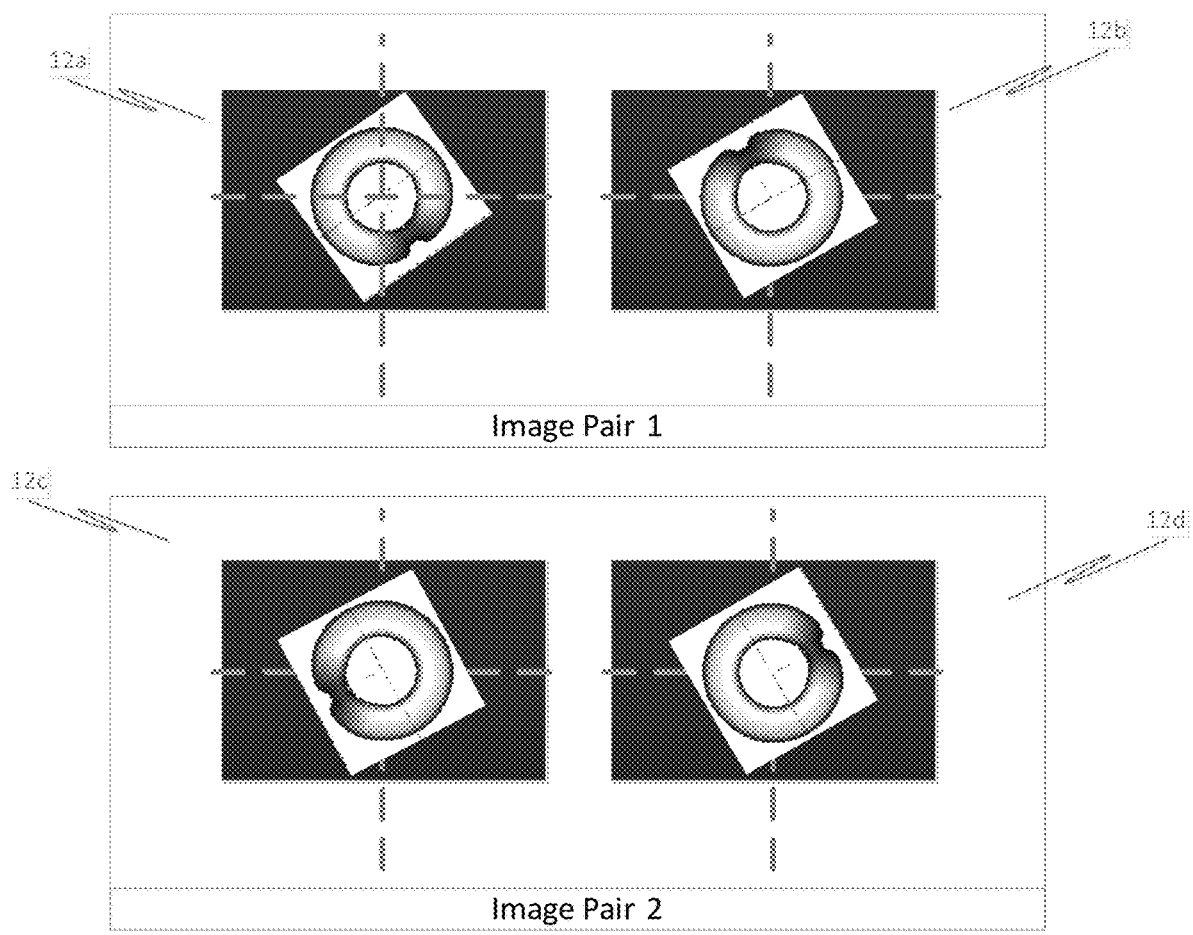
FIG. 12 illustrates two donut shaped image pairs obtained using the collimator positions of FIG. 11.

The image acquisition method used is the integral image acquisition method. As such, while the collimator is being rotated from a start position (0°, for example) to an end position, which is close to 360 degrees, the EPID 112' or 112" continuously captures the incident light, and ultimately generates a single aggregate image from the start to the end of the image acquisition process. Thus, at Step 5, an aggregate image is created. By integrating the resulting images, the aggregate image has a donut shape, as shown in FIG. 12a. In the donut shaped image, the inner and outer rings are defined by the upper jaw 121 faces. Since the collimator cannot go a full 360 degrees there will be a missing arc segment. The image acquisition is repeated in Step 6, but with the upper jaws 121 moved to an opposite offset, as shown in FIG. 12b, such that a mirrored image is created, as shown in FIG. 12b. The first image pair, as shown in FIGS. 12a and 12b, is thus generated.

After generating the first image pair, the imaging process of Steps 3-Step 6 are repeated using different jaw apertures in order to generate the second image pair. For the second image pair, in Step 3, the MLC 125 (MLC1, MLC2) and the upper jaws 121 (Upper 1, Upper 2) are positioned such that the MLC 125 is off-center and the upper jaws 121 (Upper 1, Upper 2) are symmetric, as shown in FIG. 11c. In Step 4, with all room and peripheral lights off, while the collimator is rotated as close to 360 degrees as possible, images are taken using the EPID 112' or 112". By integrating the resulting images in Step 5, a donut shaped image, as shown in FIG. 12c, is created. In the donut shaped image, the inner and outer rings of the donut are defined by the MLC 125 faces. Since the collimator cannot go a full 360 degrees, the image acquisition is repeated in Step 6, but with the MLC 125 moved to an opposite offset, as shown in FIG. 11d, such that a mirrored image is created, as shown in FIG. 12d. The first and second pair of images so created is illustrated in FIGS. 12c and 12d.

Next, in Step 7, the four (4) images are analyzed to find the exact centers of the donuts by using precise edge-detection methods together with a best-fit circle algorithm, as described in detail above, and as shown in FIGS. 20-24. To increase accuracy (due to the missing arc section), the circle centers of the opposite image pairs (FIG. 12a with 12b, and FIG. 12c with 12d) are geometrically averaged. This reduces the four (4) images to two (2) precise circle centers. The error $\delta_{cen}$ between the two circle centers is directly proportional and is deterministic of the distance ($\epsilon_{source}$) by which the light spot is offset from the collimator axis of rotation, as shown in FIG. 10. FIG. 10 shows the geometry of the setup with an off-center radiation spot. The equation to determine in Step 8, the light spot location error $\epsilon_{light\ source}$, in units of distance, is as follows:

$$\varepsilon_{light\ source} = \frac{\delta_{cen} * D_{ujaw} * D_{mlc}}{SDD * (D_{mlc} - D_{ujaw})} \quad \text{Eq. 2}$$

Where, $\delta_{cen}$ is the error between the two circle centers and is the difference between the center circle obtained from the first image pair and the center circle obtained from the second image pair; $D_{ujaw}$ is the distance between the light source and the upper jaws 121; $D_{mlc}$ is the distance between the light source and the MLC 125; and SDD is the distance between the light source and the EPID 112' or 112".

In Step 9, the offset ($\epsilon_{light\ source}$) is evaluated. If the offset ($\epsilon_{light\ source}$) falls within a prescribed range (0.4-1.2 mm, for example), the light spot is determined to be aligned with the collimator axis of rotation and no further calibration is needed. If no further calibration is needed, the calibration process is stopped at Step 10. If the offset $\epsilon_{light\ source}$ is determined to be outside of the prescribed range, the light spot location is adjusted in Step 11 by adjusting the position of the light source 130 in the radial (Y axis) and transverse (X axis) directions. By adjusting the radial (Y) and transverse (X) positions of the light source 130, the light spot can be moved to reduce the distance error until the offset ($\epsilon_{light\ source}$) falls within the accepted range, indicating that the light spot and the collimator axis of rotation are aligned. In a closed control loop algorithm, the position of the light source 130 can be automatically adjusted to align the two circle centers and thus achieve a precisely adjusted light beam. Accuracy is best with four (4) sets of images and with the EPID 112' or 112" as far from the light source as is practical. With this method, it is possible to determine the light spot alignment in the approximately 100 micron range. Alternatively, for lower accuracy or a rough pass, taking only one (1) image per pair without the mirrored image is enough. Once the light beam is adjusted, the calibration process S100 moves on to S114 to align the light spot to be at the same distance from the isoplane as the radiation beam spot.

b. Calibration Algorithm (Edge-Detection and Best-Fit Circle)

To find the exact center of each donut, and the circle center offset, an edge-detection method together with a best-fit circle algorithm, as described in detail above, and as shown in FIGS. 20-24 can be applied.

c. Alternative Embodiments

Figure 9B:
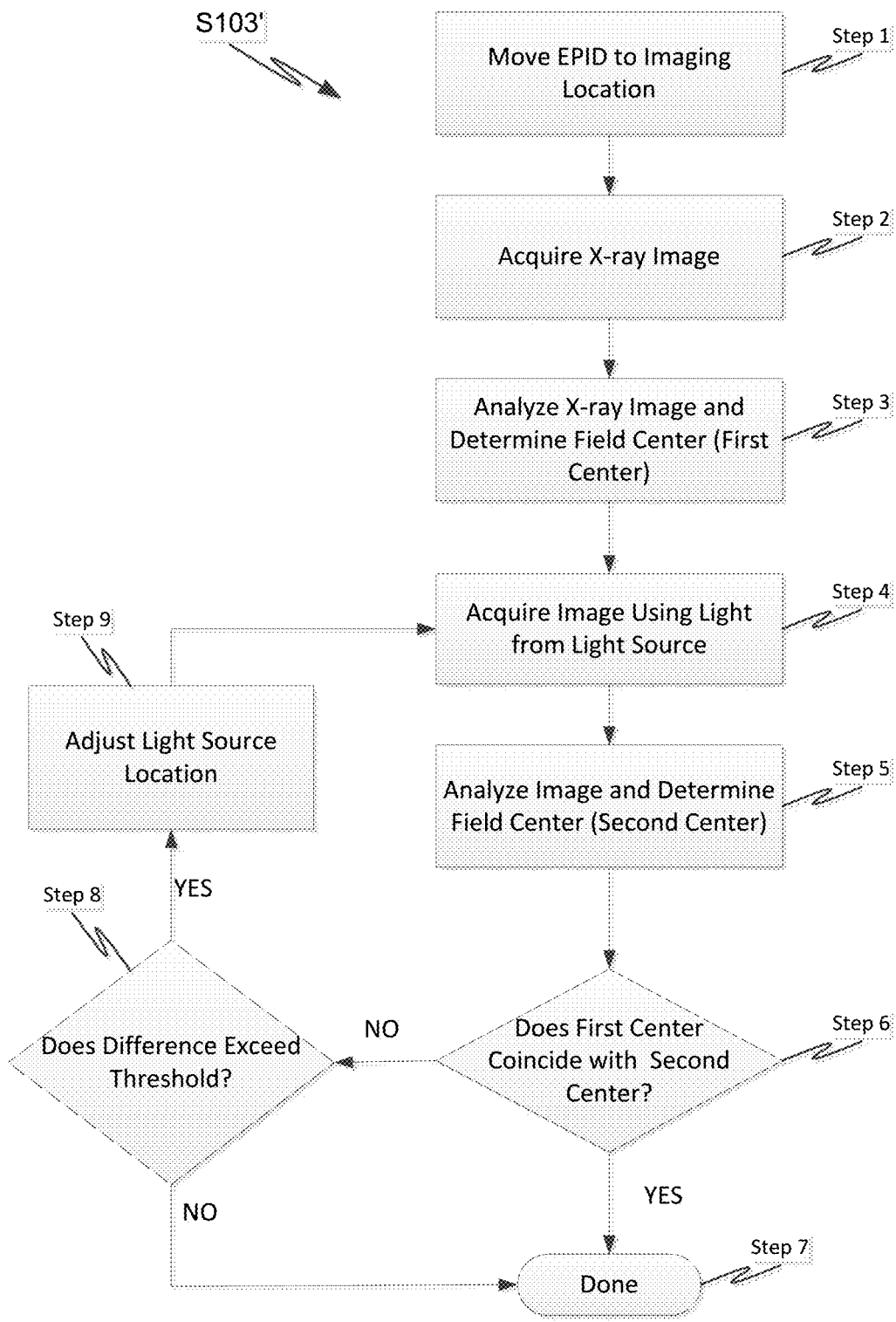
FIG. 9B illustrates an alternative process flow for calibrating the light source of a radiation treatment device according to one or more embodiments of the disclosed subject matter.

1. An alternative embodiment for aligning the light spot to the collimator axis of rotation is illustrated in FIG. 9B. The prerequisites for this alternative light field calibration process S103' is that a light-sensitive modified EPID 112' or 112" is used to capture both the X-ray radiation beam and the light beam; the modified EPID 112' or 112" pixels are homogeneous and of known constant geometry; the X-ray radiation beam has been calibrated so as to be aligned with the collimator axis of rotation; and the light source 130 is located so as to be independent from the rotation of the collimator.

In Step 1 of the calibration process, the modified EPID 112' or 112" is moved to an imaging location. This imaging location could be, but is not limited to, the SDD distance of 100 cm or 170 cm from the radiation source 118. The upper jaws 121, lower jaws 123, as well as the MLC 125 are positioned at known fixed distances $D_{ujaw}$, $D_{ljaw}$, and $D_{mlc}$, respectively, from the radiation source 118, and the upper jaws 121, lower jaws 123, and the MLC 125 are positioned to create a specific square or rectangular radiation field through the exposed collimator aperture.

After the collimator jaws are in place, an X-ray image having a given field size is acquired in Step 2 using the modified EPID 112' or 112". The acquired X-ray image is analyzed in Step 3 and, using an edge-detection method together with best-fit line/rectangle algorithms as described in detail below, the center of the X-ray image is determined. Using the same collimator jaw setup, a light field image is taken in Step 4 using the modified EPID 112' or 112". In similar fashion as for the X-ray image, the light field image is analyzed in Step 5 to determine the center of the light field image.

In Step 6, the first and second field centers are compared to determine whether there is a difference between the location of the first field center and the location of the second field center. If the two image centers coincide, within a desired tolerance range, it is determined that the light field coincides with the collimator rotation axis and the calibration ends at Step 7. If the two field centers do not coincide within a given range, the difference between the two center locations is determined in Step 8, and the light source 130 position is adjusted in Step 9. The difference between the first and second center locations is directly proportional to the light source position error. In a closed control loop algorithm, the position of the light source 130 can be automatically adjusted to align the two centers and thus, achieve a precisely adjusted light beam.

Figure 13:
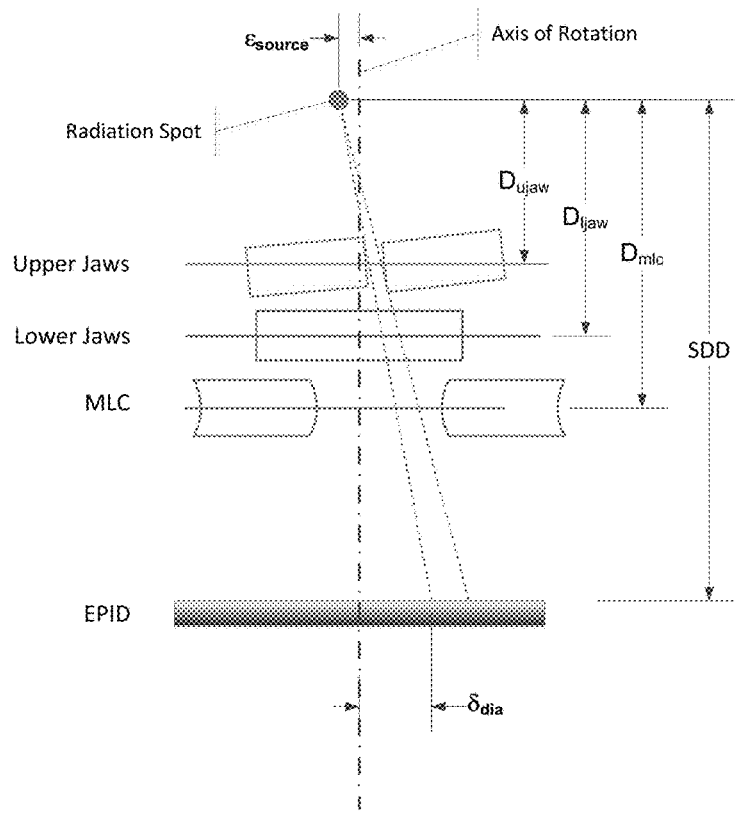
FIG. 13 illustrates the geometric layout of a collimator device and an electronic portal imaging device relative to a radiation source according to one or more embodiments of the disclosed subject matter.
Figure 14:
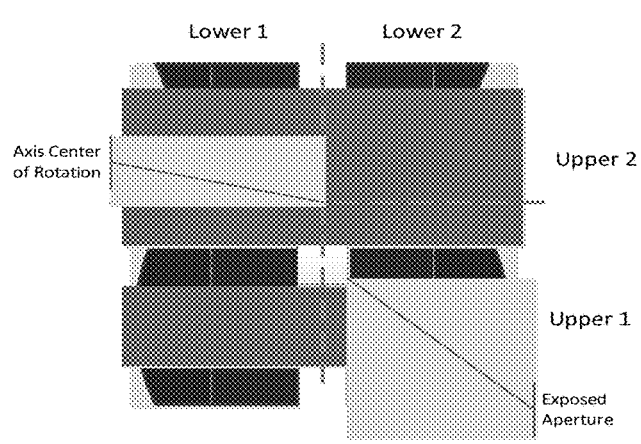
FIG. 14 illustrates collimator positions to generate an off-center field according to one or more embodiments of the disclosed subject matter.
Figure 15:
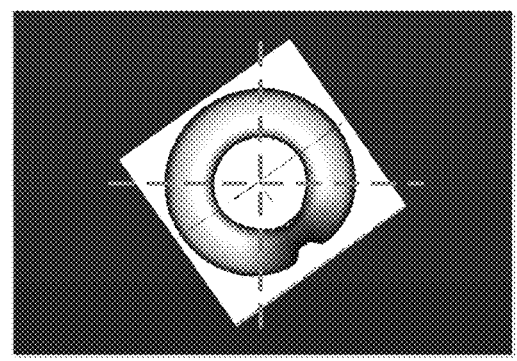
FIG. 15 illustrates a donut shaped image obtained using the collimator positions of FIG. 14.

2. In a case where the light source 130 is positioned so as to rotate with the collimator, a process S103" by which the light spot is aligned to the collimator axis of rotation is illustrated in FIG. 9C. In Step 1, the modified EPID 112' or 112" is moved to an imaging location, where the off-center image (in Step 2) is visible. The further the distance, the greater the alignment accuracy. The upper jaws 121, lower jaws 123, as well as the MLC 125, are at known fixed distances $D_{ujaw}$, $D_{ljaw}$, and $D_{mlc}$, respectively, from the light source 130. The geometric layout of the collimator jaws 121, 123, 125 and EPID positions relative to the radiation source is illustrated in FIG. 13. In Step 2, the collimator upper jaws 121 (Upper 1, Upper 2), and the lower jaws 123 (Lower 1, Lower 2) are positioned, as shown in FIG. 14, to generate a small off-center rectangular or square light field from the light source 130. Then, while the collimator is rotated from an initial first position through approximately 360 degrees to an end position, the EPID 112' or 112" acquires images of the light field in Step 3. The images so obtained are aggregated to generate an integrated donut-shaped image in Step 4, as shown in FIG. 15.

From the integrated image, the inner diameter of the donut is determined in Step 5 using any applicable algorithms. The light source 130 is then adjusted in Step 6, and the processes of Steps 3-Step 5 repeated to obtain a second aggregate image in Step 5. The diameter of this second donut-shaped image is then compared in Step 7 with the diameter of the donut shaped image obtained in the previous image. If the second diameter is smaller than the first diameter and it is the smallest diameter that can be obtained, the calibration is stopped in Step 8. If, however, the second diameter is not smaller than the first diameter, the light source 130 is adjusted again and the processes of Steps 3-Step 7 are repeated until the smallest possible circle and thus, the smallest possible diameter is generated. When the light source 130 is located along the axis of rotation of the collimator, the diameter of the circle is at the minimum. At this point the calibration is completed and the process ends at Step 8.

3. In yet another alternative embodiment where the light source 130 is positioned so as to rotate with the collimator, the light source 130 can be aligned with the collimator axis of rotation by first inserting optical cross-hairs in the path of the light field and then images are acquired at a plurality of collimator positions while the collimator is rotated through approximately 360 degrees using the modified EPID 112' or 112". The plurality of images (one at each collimator position) so obtained are then analyzed by looking at the cross-hair shadows in the images. The image circle diameters associated with the moving cross-hair positions are calculated and the light source 130 adjusted until the diameter of the circle is the smallest possible. When the light source 130 is located along the collimator axis of rotation, the diameter of the circle will be at a minimum.

3. Light Spot Alignment with the Radiation Source (Step S104)

As previously discussed, for attaining proper positioning of the patient 101 in the radiation field, the light source 130, which is used as a radiation field positioning aid, must be adjusted so that the light spot is at the same virtual point as the radiation source from the isoplane. Thus, the light source 130 needs to be at the same distance from the isoplane as the radiation spot.

The process S104 by which the light source 130 is aligned with the radiation spot is illustrated in FIG. 16. In Step 1 of this calibration process, a modified EPID 112' or 112" is first positioned at a first imaging location, which is at or near the isoplane. Then, in Step 2, an X-ray image is acquired using the radiation beam from the X-ray source 118. Without moving the EPID 112' or 112", and with all room and peripheral lights turned off, a second image is acquired using he light-field from the light source 130 in Step 3. The X-ray image acquired in Step 2 and the light-field image acquired in Step 3 are compared to each other in Step 4, and using precise edge-detection and best fit line/rectangle algorithms, such as those described in detail above, the size difference between the two images is determined. If it is determined in Step 5 that there is no size difference between the two images, or that it is within an acceptable range, the light spot is aligned with the radiation source (i.e., the light source 130 and the radiation source 118 are at the same distance from the isoplane), the calibration process ends at Step 6.

If, on the other hand, it is determined that there is a sufficient size difference between the two images, the light source 130 needs to be adjusted in Step 7. The difference between the two image field sizes is directly proportional to the distance by which the light source 130 is offset from the radiation spot location. By adjusting the light source 130 by the amount of the determined difference in the image sizes, the light source 130 can be moved to the correct location. After the light source 130 is adjusted in Step 7, the process of acquiring a light field image and comparing it to the X-ray image for the size difference can be repeated until the image sizes coincide. At that point, the light source 130 is calibrated and the process ends at Step 6.

4. Collimator Jaw Calibration (Step S105)

Calibration of the collimator jaws (121, 123) is important so that the delivered radiation to the patients is accurate to the planned treatment. Asymmetric collimators and/or non-intersecting collimator and gantry rotational axis can introduce a shift in the alignment of the axis of rotation of the collimator, the axis of rotation of the gantry, and the collimator symmetry. Since both the radiation field and the radiation source are aligned to these motion axes, the collimator jaws need to be calibrated so that they do not displace the radiation field edges by more than a set tolerance value at the plane of the isocenter. Therefore, in step S105, the collimator jaws are calibrated to establish a distance relationship between the different axes of motion of the radiation treatment device 103 and the distance of the collimator jaws at the isoplane.

a. Calibration Process

The jaw calibration procedure S105 for a drive mechanism which needs a multi-point calibration for linearization is illustrated in FIG. 17. The prerequisites for the accurate jaw calibration process is that the EPID 112 is at a known distance from the radiation source (i.e., X-ray target 118), and that the EPID 112 pixels are homogeneous and of known constant geometry. For instance, the geometric layout of the collimator jaw positions and the EPID's position relative to the radiation source is illustrated in FIG. 18 where distances $D_{ujaw}$, for the upper jaws 121 and $D_{ljaw}$ for the lower jaws 123 are known distance from the radiation spot.

In Step 1 of the jaw calibration procedure S105, the EPID 112 is moved to a known imaging location, such as, but not limited to, a distance SDD from the radiation source. In Step 2, the collimator is positioned at a first location, such that both upper jaws 121 and lower jaws 123 are positioned at a commanded distance $D_{jaw\_face}$ from the collimator center of rotation, commanded distance meaning the location where the control system moves the jaw faces.

After the collimator is set to the first location, one or more images are acquired using the EPID 112. The EPID 112 can be operated in various image acquisition modes, which can include a combination of beam energy, repetition rate, and scanning modes, including, but not limited to, acquisition of a dark-field image and a flood-field image, the dark-field image providing information about background noise and being obtained by taking a base reading for each pixel in the absence of the radiation. The EPID can also be operated to acquire alternating image pairs.

The collimator jaws 121, 123 are next set to a second $D_{jaw\_face}$ location in Step 3 and one or more images are acquired using the EPID 112. The images obtained at the first collimator jaw positions, and the images obtained at the second collimator jaw positions are analyzed in Step 4 on a per-jaw basis using a precise edge-detection method and best-fit line algorithm described in detail within this document. During Step 4, the projected distances of the collimator jaws (121, 123) on the isoplane are determined. The projected distances of the collimator jaws on the isoplane represent the distances $\delta_{face\_iso}$ of the jaws from the radiation beam centerline. The projected distances in pixels are then converted to linear distance (e.g., in mm) based upon the known geometry and known distance of the EPID 112 from the radiation source. The linear gain factor per jaw is calculated in Step 4 by comparing the difference in commanded distance versus image captured distance to create a relation between move of axis and distance at isoplane.

The calibration of the collimator jaws is done in Step 5 by setting the collimator jaws to a desired location, $D_{jaw\_face}$, to achieve a desired isoplane value of $\delta_{face\_iso}$. The software parameters are then set to associate this location with the actual $\delta_{face\_iso}$ value and thus establishing the fixed relation between motion distances and isoplane distances. With some control system 120 programs, it may be possible to directly take the information from the existing images to update the parameters fixing the relation between motion distance and isoplane distance.

In order to verify that the expected collimator positions are the correct positions, as an optional verification step, the collimator jaws are moved to an expected positions and one or more images are taken using the EPID 112. The images obtained are again analyzed and the projected distances are again calculated and evaluated in Step 6 using the edge-detection and best-fit line algorithms. If the calculated projected distances are within the prescribed values, the jaw calibration is complete (Step 7). If, on the other hand, the projected distances are not within the prescribed values, the jaws are again adjusted based on the difference between the calculated and prescribed distance values. This process can be repeated until the collimator jaws are accurate within prescribed specifications. When the jaws are within prescribed specifications, the jaws are calibrated, and process S100 moves on to the next calibration step S106.

If the collimator jaws, by design, have sufficient linear accuracy, it is not necessary to calibrate the collimator jaws at two different positions. In such a situation, the calibration procedure follows the process S105' illustrated in FIG. 19. In Step 1 of process S105', the EPID 112 is moved to a known imaging position, such as, but not limited to, a known distance SDD from the radiation source. Then, in Step 2, the upper jaws 121 and lower jaws 123 are positioned to an initial imaging location, such as, an expected distance $D_{jaw\_face}$ from the collimator rotation axis (or system global coordinate), as shown in FIG. 18, and one or more images are acquired using the EPID 112. The images obtained are then analyzed in Step 3 on a per-jaw basis using precise edge-detection methods and best-fit line algorithms to precisely determine projected distances of the collimator jaws on the isoplane, and to calculate offset error between expected position and actual position.

If the determined projected distances are within prescribed values, the collimator jaws are in the correct position and need not be adjusted. If, one the other hand, the determined projected distances are not within prescribed values, the collimator jaws are repositioned to the expected locations in Step 4, which are determined based on the differences between the calculated projected distances and the prescribed values. With some control system 120 programs, it may be possible to directly take the information from the existing images to update the parameters fixing the relation between motion distance and isoplane distance.

In order to verify that the expected positions are correct, as an optional verification step, once the collimator jaws are moved to their respective expected positions, one or more images are taken using the EPID 112 in Step 5. The images so obtained are again analyzed and the projected distances are again calculated and evaluated using the edge-detection and best-fit line algorithms. If the calculated projected distances are within the prescribed values, the collimator jaw calibration is complete in Step 6. If, on the other hand, the projected distances are not within the prescribed values, the jaws are again adjusted based on the difference between the newly calculated and the prescribed values. This process can be repeated until the collimator jaws are accurate within prescribed specifications. When the jaws are within prescribed specifications, the collimator jaws are calibrated, and process S100 moves to the next calibration step S106.

Although the collimator jaw calibration procedures S105 and S105' were described as using radiation beams (i.e., X-rays) as the radiation fields, and EPID 112 as the imager capturing the radiation beams, in alternative embodiments, the calibration procedures S105 and S105' can be implemented using light from the light source 130 and one of the modified EPIDs 112' and 112" as the imager capturing the light fields.

b. Calibration Algorithm (Edge-Detection and Best-Fit Line)

There are numerous edge-detection algorithms that can be used for the image analysis described above, one of which is illustrated in FIG. 20. The basics of the edge-detection method are to analyze the EPID image to create a linear sequence of pixels and respective values to generate a profile from which the precise location of a percentile threshold can be determined. The prerequisite for this edge-detection method is that the general location of the edge is known. This general location of the edge can be determined using any available methods, such as, but not limited to, a first pass with a general purpose edge-detection method followed by a best fit line algorithm, or a Hough Transform technique fitting method.

Prior to applying the edge-detection algorithm, if desired, an image filter is applied in Step 1 to reduce errors caused by image irregularities such as noise or image artifacts. When filters are applied, each pixel is reassigned either the value of the average of a given number of pixels around it in 2D or 3D (i.e., mean value), or the value of the median pixel (i.e., median value).

Next, in Step 2, for a given edge, estimated edge points are generated. The estimated values for each edge point are taken from prior knowledge, such as, but not limited to, information regarding the radiation treatment device 103 which has already been stored in a memory of the controller 120, or from a rough full-image edge-detection and line regression estimate using Sobel, Robert's cross, Laplacian of Gaussian, Canny's transforms and straight regression, or Hough's transform.

After the estimated edge points are calculated, the exact edge profile for each point is created in Step 3. This involves identifying a start point $p_0$ and an end point $p_1$ orthogonal to the expected edge line. Since the offset distance from the estimated edge point is system dependent, the certainty of estimated point, the size of the penumbra, the potentially interfering geometry, and the homogony of dark and light areas can also be considered. Then using the normalized line method, the start and end points are connected in both radial (Y) and transverse (X) directions and, at a given increment, steps are taken from 0 to 1 using the following normalized line equations:

$$X_{(i)} = (X_2 - X_1)*i + X_1 \qquad \text{Eq. 3}$$

$$Y_{(i)} = (Y_2 - Y_1)*i + Y_1 \qquad \text{Eq. 4}$$

where i is the step from 0 to 1.

Figure 21:
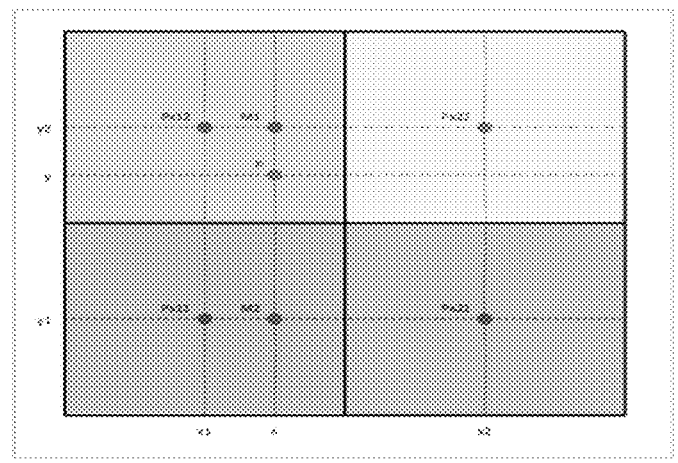
FIG. 21 illustrates a bilinear interpolation method according to one or more embodiments of the disclosed subject matter.
Figure 22:
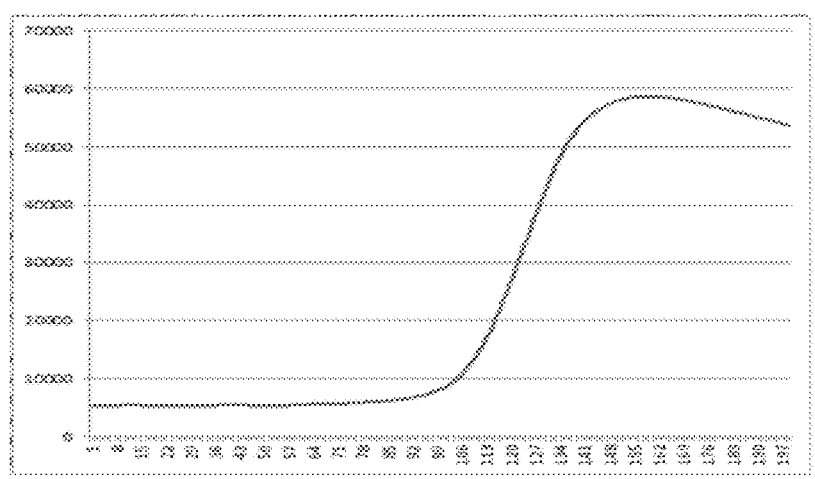
FIG. 22 illustrates a penumbra profile according to one or more embodiments of the disclosed subject matter.

At each point between the start point $p_0$ and the end point $p_1$, the actual pixel value can be interpolated since it will typically be between pixel centers. There are numerous interpolation methods that can be used to determine the pixel value, such as, but not limited to, linear, bilinear, Bezier, polynomial, methods, incorporated herein by reference. Using a bilinear interpolation method as shown in FIG. 21, wherein four pixels surrounding each step location is taken into consideration, a penumbra profile as shown in FIG. 22 is generated. This penumbra profile is the result of the linear interpolated results along the normal line.

After the edge profile is generated as shown in FIG. 22, the exact edge point per profile is calculated in Step 4. Determination of an edge point includes analyzing the edge profile to determine the threshold of interest. For this, a search is done to find the closest points above (i.e., maximum value) and below (i.e., minimum value) the threshold value and then direct linear interpolation between these points to calculate a precise coordinate. Determination of the exact threshold is system dependent. In case of radiation delivery, a threshold of 50%, for example, can be selected. The determination of the minimum value (i.e., point below threshold value) can be done many different ways, including, but not limited to, selecting the minimum value in the profile or averaging of the first few values at the start or end points, or average a sample of the entire image area outside of the exposed area. Determination of the maximum value (i.e., point above threshold value) can be done in many different ways, including, but not limited to selecting the maximum value in the profile, or averaging of the first few values at the start or end points, or averaging of a given number of pixels at the center of the exposed area (i.e., center of the radiation field). Next, the best-fit edge to population of edge points is determined in Step 5.

Figure 23:
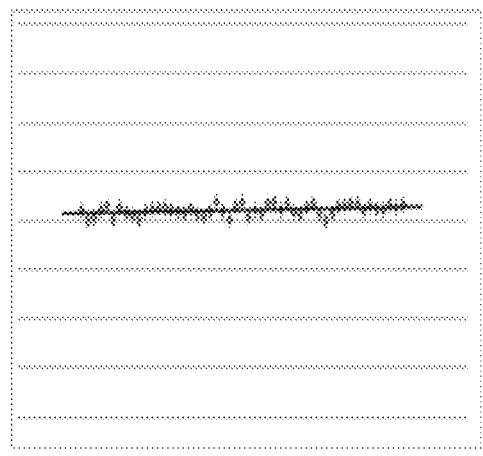
FIG. 23 illustrates an exemplary best-fit line according to one or more embodiments of the disclosed subject matter.
Figure 24:
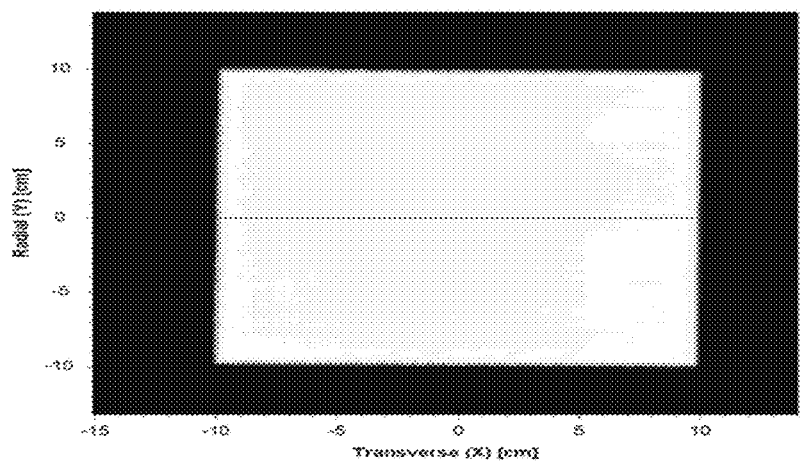
FIG. 24 illustrates an exemplary image with a best-fit line according to one or more embodiments of the disclosed subject matter.

The best-fit line, as shown in FIG. 23, is calculated by analyzing all edge points found along an expected line region. Any of available the best-fit algorithms can be applied to determine the best-fit line. FIG. 24 illustrates an example of an image with the best-fit line.

5. Angle Steering Coil Calibration (Step S106)

For the accurate radiation delivery to the patient 101 under the radiation treatment device 103, it is important that the electron pencil beam hits the X-ray target 118 at a perpendicular angle. When the electron pencil beam hits the X-ray target 118 at a perpendicular angle, the radiation beam generated from the X-ray target 118 is symmetric. The symmetry of a radiation beam is considered with regards to the radiation beam center as it is projected from the radiation source 118 past the radiation limiting devices (collimator jaws) to the isoplane. In the radiation treatment field, the symmetry is considered along the X-axis and the Y-axis, with the Z axis being from the radiation source to the isoplane, and the Y axis increasing from the center toward the gantry stand structure, as shown in FIGS. 2A and 2B. Adjusting the angle of incidence of the electron pencil beam onto the X-ray target 118 can be accomplished by adjusting the angle steering coils in the radial and transverse directions.

If the electron beam does not hit the target 118 orthogonally, it will create an asymmetric radiation beam when looking at an un-flattened beam (i.e., no flattening filters 117 present). An asymmetric beam may introduce errors in the radiation beam delivered onto the patient. Since the angle of incidence of the electron pencil beam onto the X-ray target 118 is adjusted by adjusting the angle steering coils in the radial and transverse directions, in S106, the angle steering coils of the radiation treatment device 103 are calibrated in the radial and transverse angles so that the electron pencil beam hits the X-ray target 118 at a perpendicular angle.

a. Normalizing the EPID Image (Generating the Normalized Conversion Map)

Prior to the commencement of the angle steering coil calibration process, the EPID 112 is normalized. In order to accurately capture the radiation output and resulting radiation beam profile, the EPID 112 is calibrated such that the pixel sensitivities are normalized. This enables converting a standard EPID image into a relative radiation beam profile from which it becomes possible to analyze the radiation beam symmetry as well as the radiation beam flatness.

An exemplary algorithm to normalize the EPID 112 is disclosed in U.S. Patent Publication US 2012/0014618, filed Mar. 23, 2011, which is incorporated herein by reference in its entirety. In essence, the normalization algorithm determines the gain at each pixel of an area of the imager 112, as well as the radiation beam profile at each space in a radiation beam field corresponding to a set of one dimensional arrays of regularly spaced regions of interest. The normalization algorithm also provides a two-dimensional map of radiation beam profile and imager gain. This is obtained by first generating the beam profile and gain map for two spatially correlated images by determining a second set of one-dimensional beam profiles for the images in a separate direction (dimension) from the first one-dimensional beam profiles, followed by correlating the images by selecting the same sampling points within the two images.

The two-dimensional map of radiation beam profile and imager gain (i.e., normalized conversion map) can be stored in a processor of the controller 120 and selectively implemented to normalize the EPID 112 images, when needed.

The so calibrated EPID 112 system is hereinafter referred to as the "normalized EPID image." The output normalized EPID image reflects the relative incident flux intensity distribution. As such, the normalized EPID measures the real time relative flux map. The image is relative since during the normalization calibration approach the actual delivered flux is not absolutely measured.

b. Calibration Process

Figure 25:
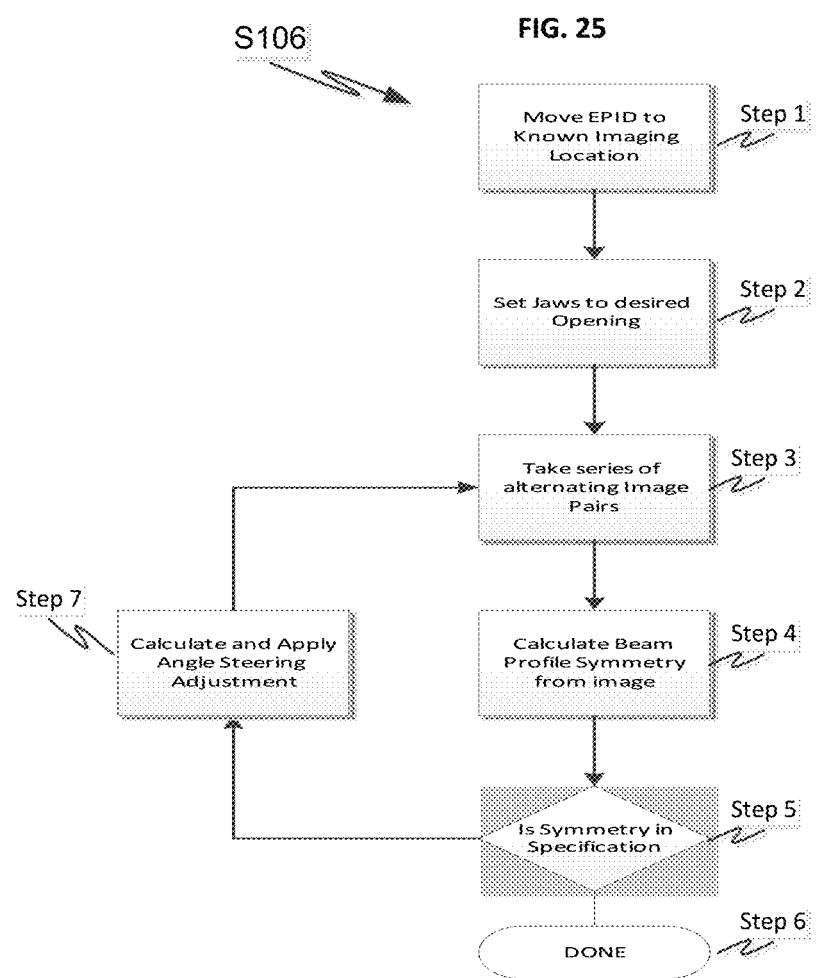
FIG. 25 illustrates a process flow for calibrating the angle steering coils of a radiation treatment device according to one or more embodiments of the disclosed subject matter.

An exemplary calibration process for the angle steering coils is illustrated in FIG. 25. Since a given radiation system 103 can deliver multiple X-ray energies, the calibration procedure is repeated for each energy independently. Through this calibration process, using an EPID 112 or modified EPIDs 12', 112" at or near the isoplane, it is possible to accurately capture the radiation beam profile and subsequently determine the symmetry of the radiation beam. With real-time symmetry information, an automatic loop can be implemented to dynamically adjust the angle steering coils in both the radial (Y-axis) and the transverse (X-axis) planes to achieve a symmetric beam and thus a perpendicular electron beam.

In Step 1 of the angle steering coil calibration process S106, the EPID 112 is moved to a known imaging location. In order to capture a large field size (40×40 cm, for example), the EPID 112 can be moved to the isoplane location. Next, the collimator jaws 121, 123, and 125 are set, in Step 2, to a desired aperture, which could be, but is not limited to, a 40×40 cm field size. In general, the largest field size that the EPID 112 can capture is selected. Otherwise, the largest imaging size is selected, provided that there is an unexposed region of the EPID 112 still visible. The desired X-ray energy mode is next selected and the flattening filters 117 are removed from the radiation beam path. With this setup, a series of alternating image pairs are acquired in Step 3 using the EPID 112. The taking of alternating image pairs involves taking successive pairs of dark and flood field images. The image pairs are generally captured for a period of time (i.e., a set number of image pairs, or image pairs captured within an elapsed image acquisition time) and an average image is generated from these plurality of image pairs. The resulting integrated image has a superior accuracy. The image acquisition mode by which alternating pairs of dark field and flood field images are taken is described in detail in U.S. Patent Publication US 2012/0014618, filed Mar. 23, 2011, and is incorporated herein by reference in its entirety.

From the average image generated from the series of alternating image pairs, the beam profile symmetry is next calculated in Step 4. To calculate the beam profile symmetry, the image is first converted into a radiation dose map using the normalized conversion map, then, if desired, an image filtering algorithm, such as, but not limited to, mean, median, Gaussian, or a combination of median and Gaussian filtering algorithms are applied to remove imaging errors. The symmetry of the delivered radiation beam can be computed using any one of a symmetry calculation algorithm described in detail below.

After the beam symmetry is calculated from the EPID image, the symmetry is evaluated in Step 5 to determine whether it falls within a prescribed symmetry range. If it does, the angle steering coils need not be adjusted and the calibration is complete. The calibration procedure is then stopped in Step 6. If the determined radiation beam symmetry does not fall within the prescribed range, the angle steering coils are adjusted in the radial and transverse angles in Step 7 according the determined asymmetry. After the initial adjustment in Step 7, another series of alternating image pairs are again taken with the EPID 112 and the symmetry of the radiation beam again calculated and evaluated. This automatic loop is repeated until the symmetry of the radiation beam is within specification. At that point, the angle steering coils are considered to be tuned and the electron pencil beam hits the X-ray target 118 perpendicularly. The calibration process S100 can move on to Step S107.

c. Calibration Algorithm (Symmetry Calculation)

The symmetry of the delivered radiation beam can be computed using a plurality of algorithms, such as, but not limited to, a 2-Point difference method, Area (2D) method, 2D slope deviation method, Volume (3D) method, 2D centroid method, and 3D centroid method.

1. 2-Point Difference Symmetry Calculation Method

Figure 26:
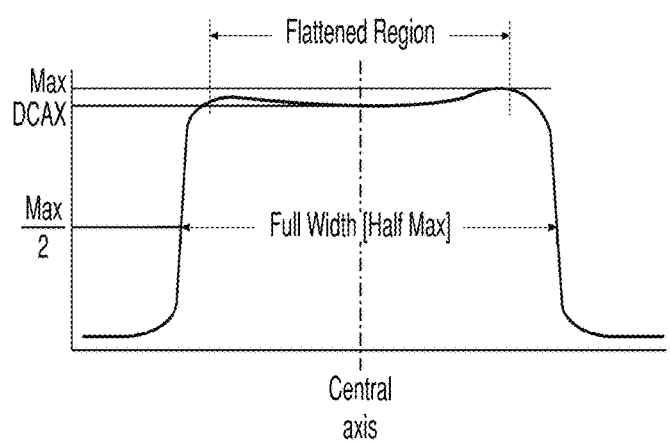
FIG. 26 illustrates a radiation beam profile according to one or more embodiments of the disclosed subject matter.

In the 2-Point difference symmetry calculation method, a profile shape is generated, as shown in FIG. 26, by either scanning a radio-sensitive sensor across the radiation field, or by generating a cross section cut of the normalized EPID image. The main profiles are along the X and Y axis. The symmetry is calculated according to the following equation:

$$\text{Symmetry} = 100 * \frac{\text{Max}(|Point_L - Point_R|)}{DCAX} \quad \text{Eq. 5}$$

Where, DCAX is the dose at central axis (CAX); and Max(|PointL-PointR|) is a search resulting in the absolute value maximum dose variation between two points within the region of 80% of Full Width [Half Max] (FWHM). FWHM is the horizontal region bound on the Left (L) and Right (R) by the region where the curve intersects half of the maximum value.

2. Area (2D) Symmetry Calculation Method

Figure 27:
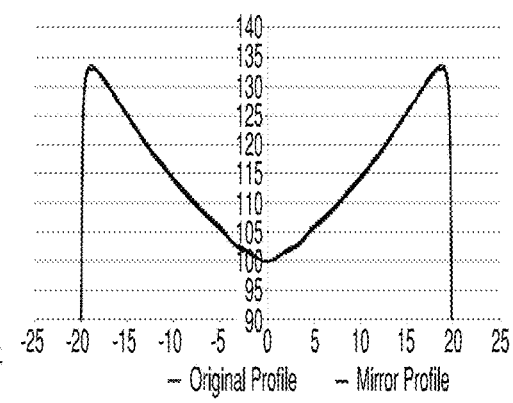
FIG. 27 illustrates a radiation beam profile according to one or more embodiments of the disclosed subject matter.

In the Area (2D) symmetry calculation method, a profile shape is generated, as shown in FIG. 27, by scanning a radio-sensitive sensor across the radiation field or by generating cross section cuts of the normalized EPID image. The main profiles are also along the X and Y axis. This symmetry calculation method involves comparing areas (Right-Left) down to 50% of CAX. The symmetry is calculated according to:

$$\text{Symmetry} = 100 * \frac{|Area_L - Area_R|}{|Area_L + Area_R|} \quad \text{Eq. 6}$$

$Area_L$ is the area under the curve bound on the left (L) by where the curve intersects the half Maximum value and on the right (R) by the Central Axis (CAX); and AreaR is defined similarly as Areas except on the other side of CAX.

This method has an advantage over the 2-Point method because the noise which is inherently generated in the 2-Point method is filtered out.

3. 2D Slope Deviation Symmetry Calculation Method

Figure 28:
FIG. 28 illustrates a radiation beam profile according to one or more embodiments of the disclosed subject matter.

In this method the profile is generated, as shown in FIG. 28, by scanning a radio-sensitive sensor across the radiation field or by generating cross section cuts of the normalized EPID image. The main profiles are along the X and Y axis. In this method, the profile and mirror imaged profile of the FWHM region are subtracted to generate a symmetry difference profile. From the symmetry difference profile, a best-fit line is generated and the slope of the points are calculated from CAX to the end. This method has the advantage over both the 2-Point and Area (2D) symmetry calculation methods because the noise filtering is increased. Further, the Area (2D) method does not take into account profile shape and trends, whereas the slope method considers the profile shape and anticipates greater deviation away from the center where more radiation is delivered meaning it may be more sensitive or responsive for asymmetric beams.

4. Volume (3D) Symmetry Calculation Method

Figure 29A:
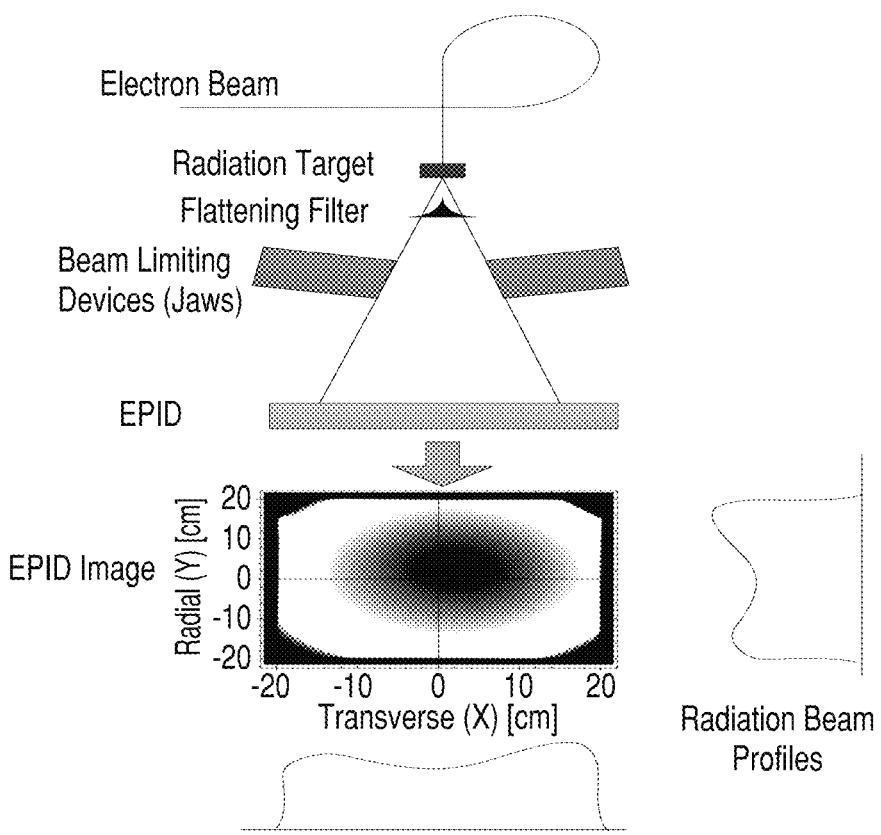
FIGS. 29A and 29B illustrate radiation beam profiles generated from electronic images according to one or more embodiments of the disclosed subject matter.
Figure 29B:
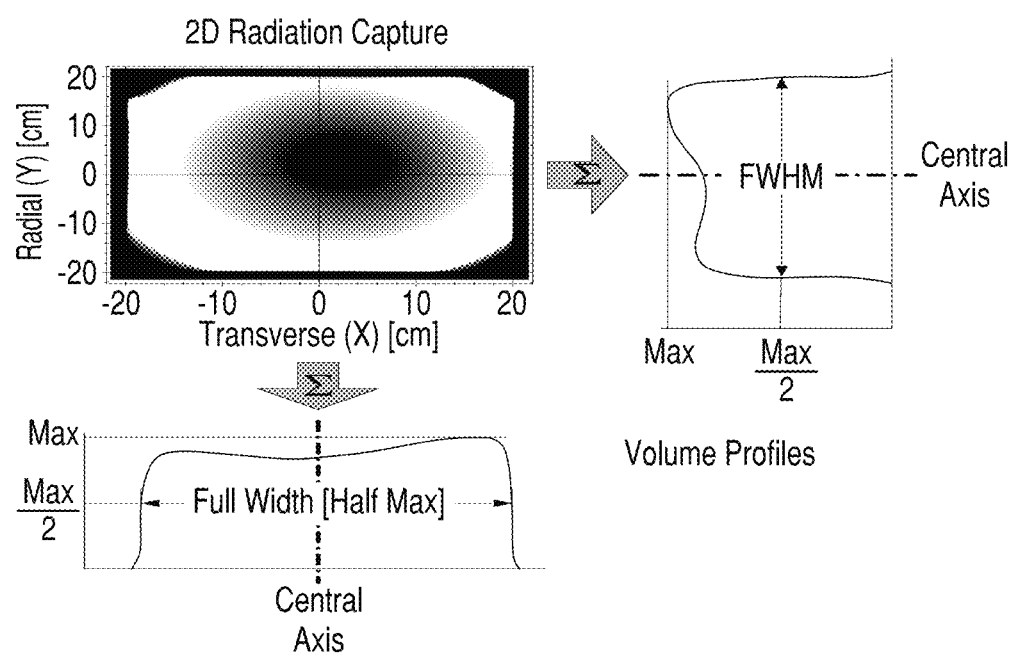

This symmetry calculation method is a variant of the Area (2D) method. The analysis starts with a full 2D scan of the radiation area, which is the same as the normalized EPID image. From this 2D map aggregate, shown in FIG. 29A, volume profiles are created along the X and Y axes by summing discrete 'rows' of values. These volume profiles are analyzed to comparing right (R) and left (L) regions to generate symmetry metrics, as shown in FIG. 29B. For symmetry, the areas (Right-Left) down to 50% of CAX are compared according to:

$$\text{Symmetry} = 100 * \frac{|Area_L - Area_R|}{|Area_L + Area_R|} \quad \text{Eq. 7}$$

Where, $Area_L$ is the area under the curve bound on the left (L) by where the curve intersects the half Maximum value and on the right (R) by the Central Axis (CAX); and AreaR is defined similarly as Areas except on the other side of CAX.

The advantage of the Volume method is that it considers the entire beam delivery and is not affected by any local anomalies which would exist along the X and Y cut planes. This method further filters out the noisiness of a field capture.

5. 2D Centroid Symmetry Calculation Method

Figure 30:
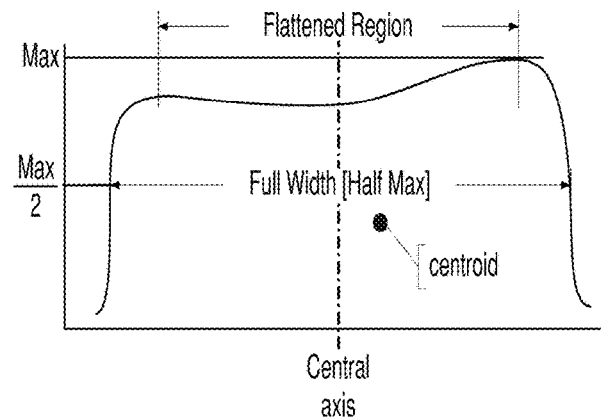
FIG. 30 illustrates a radiation beam profile according to one or more embodiments of the disclosed subject matter.

This method is a variant of the Area method. The profile, as shown in FIG. 30, is generated by scanning a radio-sensitive sensor across the radiation field or by generating cross section cuts of the normalized EPID image. The main profiles are along the X and Y axis. In this symmetry calculation method, the centroid of the area under the profile bound by the Flattened Region is calculated to find the distance error between the CAX and the centroid, according to:

$$\text{Symmetry} = \frac{\sum (Ra_i * dD_i) * D_i}{\sum Ra_i * dD} - CAX \quad \text{Eq. 8}$$

Where i is an incremental step; $dD_i$ is the incremental step; $D_i$ is the distance from CAX; and $Ra_i$ is the dose value of the profile at location i.

The advantage of this method is that it considers all of the data from the profile. This method also puts additional importance to the radiation further from the central axis.

6. The 3D Centroid Symmetry Calculation Method

This method is a variant of the 2D Centroid method. The analysis starts with a full 2D scan of the radiation area, which would come from the normalized EPID image. From this 2D map aggregate, volume profiles are created along the X and Y axes by summing discrete 'rows' of values. These volume profiles are then analyzed to compare right (R) and left (L) regions to generate symmetry metrics. In this method, the centroid of the area under the volume profile bound by the Flattened Region is computed to find the distance error between the CAX and the centroid, according to:

$$\text{Symmetry} = \frac{\sum (Ra_i * dD_i) * D_i}{\sum Ra_i * dD} - CAX \quad \text{Eq. 9}$$

Where i is an incremental step; $dD_i$ is the incremental step; $D_i$ is the distance from CAX; and $Ra_i$ is the dose value of the profile at location i.

The advantage of this method is that it considers all of the data from the radiation delivery. This method also puts additional importance to the radiation further from the central axis. In addition, by using the entire radiated region, local anomalies are also filtered out.

4. Calibration of Position Steering Coils (Step S107)

For the accurate radiation delivery to the patient 101 under the radiation treatment device 103, it is important that the radiation beam follows the path along the axis of rotation of the collimator. This is possible if the radiation beam spot is aligned to the axis of rotation of the collimator. Such an alignment is achieved in S107 by adjusting the electron pencil beam position in radial and transverse directions by tuning the position steering coils within the beam steering system 116 until the radiation spot is aligned with the collimator axis of rotation.

a. Calibration Process

The position steering coil calibration process S107 is illustrated in FIG. 31A. Since a given radiation system 103 can deliver multiple X-ray energies, the calibration procedure is repeated for each energy independently. The prerequisites for an accurate steering coil calibration process S107 is that the EPID 112 is at a known distance from the radiation source (X-ray target 118), and that the EPID 112 pixels are homogeneous and of known constant geometry.

Figure 32:
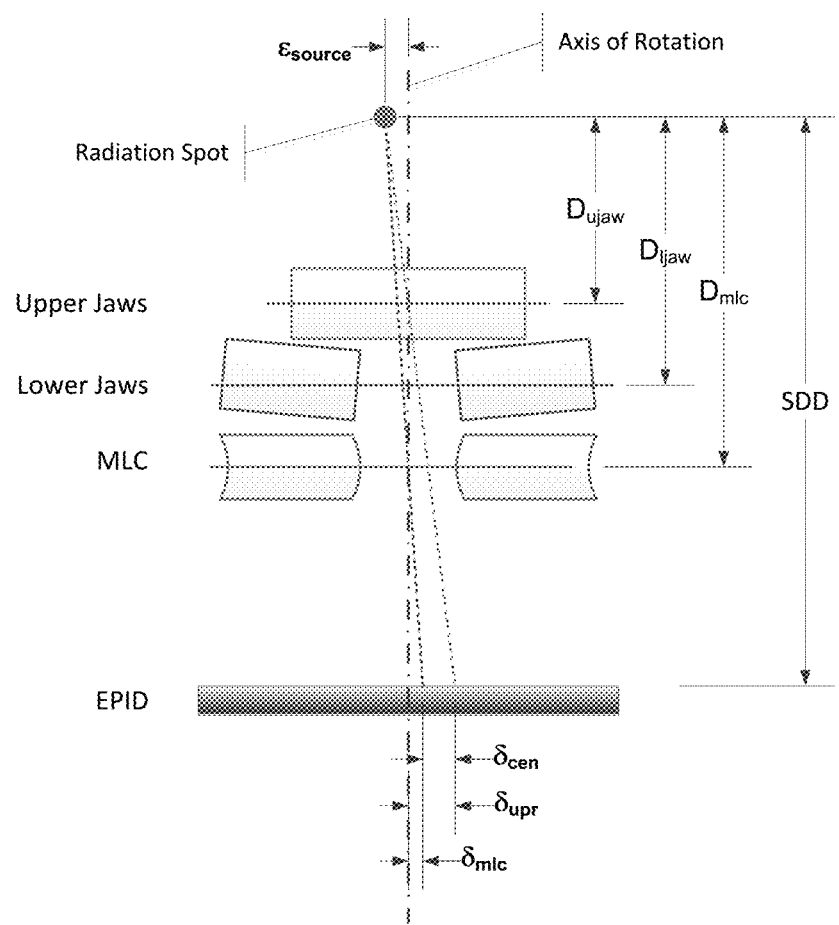
FIG. 32 illustrates a geometric layout of a collimator and an electronic portal imaging device positions from a radiation source according to one or more embodiments of the disclosed subject matter.

In Step 1 of the calibration process, the EPID 112 is moved to a known distance from the radiation source. This distance could be, but is not limited to, the SDD distance of 100 cm or 170 cm from the radiation source. The upper jaws 121, lower jaws 123, as well as the MLC 125 are at a known fixed distances $D_{ujaw}$, $D_{ljaw}$ and $D_{mlc}$, respectively, from the radiation source. The geometric layout of the collimator jaws 121, 123, 125 and EPID 112 positions relative to the radiation source is illustrated in FIG. 32. Once the EPID 112 is positioned to the initial imaging location, in Step 2, four images (i.e., two pairs) are acquired using the EPID 112. The images are taken in pairs.

The first pair of images is taken by first positioning, in Step 3, the upper jaws 121 (Upper 1, Upper 2) and the lower jaws 123 (Lower 1, Lower 2), as shown in FIG. 11a, to create a small off-center field. To create the small off-center field, the upper jaws 123 are moved off-center while the lower jaws 121 are positioned symmetrically to generate a small (1-2 cm, for example) square or rectangular radiation field through the exposed collimator aperture. Once the upper and lower jaws are in place, the collimator rotation and the image acquisition is initiated simultaneously in Step 4. During Step 4, while the collimator is rotated as close to 360 degrees as possible, images are taken using the EPID 112. The image acquisition method used is the integral image acquisition method. As such, while the collimator is being rotated from a start position to an end position, which is close to 360 degrees, the EPID 112 continuously captures the incident radiation, and ultimately generates a single aggregate image from the start to the end of the image acquisition process. Thus, at Step 5, an aggregate image is created. By integrating the resulting images, a donut shaped image, as shown in FIG. 12a is created. In the donut shaped image, the inner and outer rings are defined by the upper jaw 121 faces. Since the collimator cannot go a full 360 degrees there will be a missing arc segment. The image acquisition is repeated in Step 6, but with the upper jaws 121 moved to an opposite offset, as shown in FIG. 11b, such that a mirrored image is created, as shown in FIG. 12b. The first image pair, as shown in FIGS. 12a, 12b is thus generated.

After acquiring the first image pair, Steps 3-Step 6 of the calibration process are repeated using different jaw apertures in order to generate the second image pair. For the second image pair, in Step 3, the MLC 125 (MLC1, MLC2) and the upper jaws 121 (Upper 1, Upper 2) are positioned such that the MLC is off-center and the upper jaws (Upper 1, Upper 2) are symmetric, as shown in FIG. 11c. In Step 4, while the collimator is rotated as close to 360 degrees as possible, images are taken using the EPID 112. By integrating the resulting images in Step 5, a donut shaped image, as shown in FIG. 12c is created. In the donut shaped image, the inner and outer edges of the donut are defined by the MLC 125 faces. Since the collimator cannot go a full 360 degrees, the image acquisition is repeated in Step 6, but with the MLC moved to an opposite offset, as shown in FIG. 11d, such that a mirrored image is created, as shown in FIG. 12d, completing the second image pair. The first and second pair of images so created is illustrated in FIGS. 12c and 12d.

Next, in Step 7, the four (4) images are analyzed to find the exact centers of the donuts by using a precise edge-detection method together with a best-fit circle algorithm, as described in detail above. To increase accuracy (due to the missing arc section), the circle centers of the opposite image pairs (FIGS. 12a and 12b, and FIGS. 12c and 12d) are geometrically averaged. This reduces the four (4) images to two (2) precise circle centers. The error $\delta_{cen}$ between the two circle centers is directly proportional and is deterministic of the distance ($\epsilon_{source}$) by which the radiation spot is offset from the collimator axis of rotation, as shown in FIG. 32. FIG. 32 shows the geometry of the setup with an off-center radiation spot. Also shown are lines between the radiation spot and the determined circle centers. All of the dimensions shown in the diagram are known after image analysis and circle center calculations. The equation to determine, in Step 8, the radiation spot location error $\epsilon_{source}$, in units of distance, is as follows:

$$\varepsilon_{source} = \frac{\delta_{cen} * D_{ujaw} * D_{mlc}}{SDD * (D_{mlc} - D_{ujaw})} \quad \text{Eq. 10}$$

Where, $\delta_{cen}$ is the error between the two circle centers and is the difference between the center of the circle obtained from the first image pair and the center of the circle obtained from the second image pair; $D_{ujaw}$ is the distance between the radiation source and the upper jaws 121; $D_{mlc}$ is the distance between the radiation source and the MLC 125; and SDD is the distance between the radiation source and the EPID 112.

In Step 9, the offset is evaluated. If the offset (ϵsource) falls within a prescribed range, the radiation beam spot is determined to be aligned with the collimator axis of rotation and no further calibration is needed. If no further calibration is needed, the calibration process is stopped at Step 10. If the offset $\epsilon_{source}$ is determined to be outside of the prescribed range, the radiation spot location is adjusted in Step 11 by adjusting the position steering coil currents. The $\epsilon_{source}$ value can be converted into their Radial (Y-axis) and Transverse (X-axis) components by using the similar coordinates of the EPID 112. Adjusting the radial (Y axis) and transverse (X axis) steering currents, the radiation beam spot can be moved to reduce the distance error until the offset ($\epsilon_{source}$) falls within the accepted range, indicating that the radiation beam spot and the collimator axis of rotation are aligned. In a closed control loop algorithm, the position steering of the beam can be automatically adjusted to align the two circle centers and thus achieve a precisely adjusted radiation beam. Accuracy is best with four (4) sets of images and with the EPID 112 as far from the radiation source as is practical. With this method, the spot alignment can be determined with approximately a 10 micron range.

Alternatively, for lower accuracy or a rough pass, taking only one (1) image per image pair (i.e., without the mirrored image) could be enough. Also, for a general knowledge as to where the center of rotation is, any single image may be used. Once the radiation beam is adjusted, the calibration process S100 moves on to S108 to align the flattening filters 117 to generate flattened X-ray beams.

b. Calibration Algorithm

Figure 20:
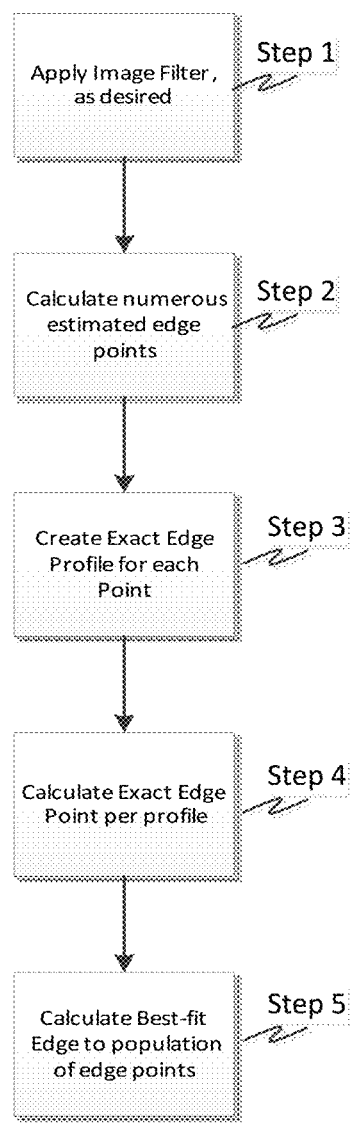
FIG. 20 illustrates a process flow for an edge-detection algorithm according to one or more embodiments of the disclosed subject matter.

To find the exact center of each donut, and the circle center offset, the edge-detection method as shown in FIG. 20 and as described in detail above, together with a best-fit circle algorithm can be applied. Using the edge-detection method and a bets-fit circle algorithm, Equation 10 can be arrived from the geometry shown in FIG. 32. From this geometry:

$$\varepsilon_{source} = D_{ujaw}\left(\frac{\delta_{upr}}{SDD - D_{ujaw}}\right) \quad \text{Eq. 11}$$

$$\varepsilon_{source} = D_{ujaw}\left(\frac{\delta_{mlc}}{SDD - D_{mlc}}\right) \quad \text{Eq. 12}$$

$$\delta_{cen} = \delta_{upr} - \delta_{mlc} \quad \text{Eq. 13}$$

Where $\delta_{supr}$ is the center of the circle obtained from the first image pair; and $\delta_{mlc}$ is the center of the circle obtained from the second image pair.

Substituting Eq. 13 into Eq. 12 gives:

$$\varepsilon_{source} = (\delta_{upr} - \delta_{mlc})\left(\frac{D_{mlc}}{SDD - D_{mlc}}\right) \quad \text{Eq. 14}$$

Solving Eq. 11 for $\delta_{upr}$ $$\varepsilon_{source} = D_{ujaw}\left(\frac{\delta_{upr}}{SDD - D_{ujaw}}\right) \text{ solve,}$$

$$\delta_{up} \to -\frac{\varepsilon_{source}(Dujaw - SDD)}{D_{ujaw}}$$

Substituting Eq. 11 solved for $\delta_{up}$ into Eq. 14 gives:

$$\varepsilon_{source} = \left[\frac{-\varepsilon_{source}}{D_{ujaw}}(-SDD + D_{ujaw}) - \delta_{cen}\right]\left(\frac{D_{mlc}}{SDD - D_{mlc}}\right) \text{ solve,}$$

$$\varepsilon_{source} \to \frac{D_{mlc}D_{ujaw}\delta_{cen}}{D_{mlc}SDD - D_{ujaw}SDD}$$

Final Equation gives:

$$\varepsilon_{source} = \frac{D_{mlc}D_{ujaw}}{SDD(D_{mlc} - D_{ujaw})}\delta_{cen} \text{ solve,} \quad \text{Eq. 15}$$

$$\delta_{cen} \to \frac{SDD\varepsilon_{source}(D_{mlc} - D_{ujaw})}{D_{mlc}D_{ujaw}}$$

$$\varepsilon_{source}(D_{ujaw}, D_{ljaw}, SDD, \delta_{cen}) = \frac{D_{ljaw}D_{ujaw}}{SDD(D_{ljaw} - D_{ujaw})}\delta_{cen}$$

$$\delta_{cen}(D_{ujaw}, D_{ljaw}, SDD, \varepsilon_{source}) = \frac{SDD(D_{ljaw} - D_{ujaw})}{D_{ljaw}D_{ujaw}}\varepsilon_{source} \quad \text{Eq. 16}$$

Calculating the center to center error $\delta_{error}$ as found on the detector is as follows:

$$\delta_{error}(X_{top}, Y_{top}, X_{btm}, Y_{btm}) = \sqrt{(X_{top}-X_{btm})^2+(Y_{top}-Y_{btm})^2} \quad \text{Eq. 17}$$

Where $X_{top}$ is the upper jaws center location in the X direction; $X_{btm}$ is the lower jaws center location in the X direction; $Y_{top}$ is the upper jaws center location in Y direction; and $Y_{btm}$ is the lower jaws center location in the Y direction.

From Eq. 17, the normalized X and Y vectors based on center locations can be calculated, as follows:

$$Xv(X_{top}, X_{btm}, \delta_{error}) = \frac{X_{top} - X_{btm}}{\delta_{error}} \quad \text{Eq. 18}$$

$$Yv(Y_{top}, Y_{btm}, \delta_{error}) = \frac{Y_{top} - Y_{btm}}{\delta_{error}} \quad \text{Eq. 19}$$

From Eqs. 18 and 19:

$$\text{Error}_{source}(Xv, Yv) = (_{Yv}{}^{Xv}) \quad \text{Eq. 20}$$

Converting source error into X (radial) and Y (transverse) offset distances gives:

$$\text{Error}_{source}(\text{Error}_{vec}, \delta_{source}) = \delta_{source} \cdot \text{Error}_{vec} \quad \text{Eq. 21}$$

which defines the radial and transverse positioning errors for the radiation source.

c. Alternative Embodiment

Figure 31B:
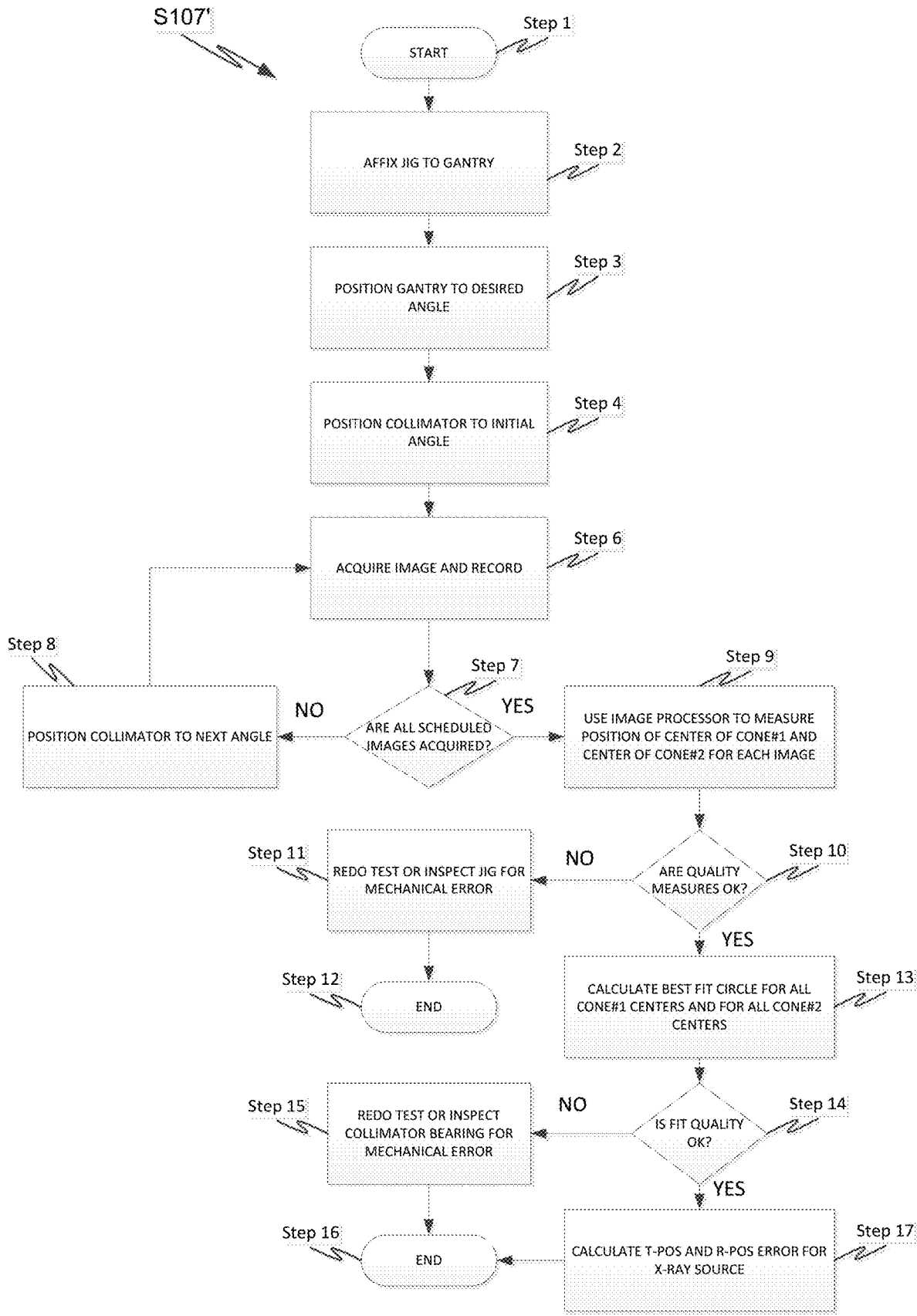
FIG. 31B illustrates an alternative process flow for calibrating the steering coils of a radiation treatment device according to one or more embodiments of the disclosed subject matter.

An alternative embodiment for the position steering coil calibration process is illustrated in FIG. 31B as process S107'. The calibration process S107' starts at Step 1. In Step 2, an alignment jig 140, as shown in FIG. 33A, is affixed to the gantry 106 such that it rotates with the collimator rotation stage, as shown in FIG. 33B. The alignment jig 140 is essentially a mechanical mask that can be mounted to the collimator face and serves as means to attenuate the radiation beam and thus create artifacts in an image captured by the EPID 112 with objects of known geometry. The alignment jig 140 can include a first circular cone-shaped center hole (Cone #1) that attenuates radiation from the X-ray source, and a second cone-shaped center hole (Cone #2) which is coaxial with the first circular cone-shaped center hole (Cone #1) and further attenuates the radiation beam in the image captured by the EPID 112. The two through-holes serve as the functional cones with regard to attenuating radiation. The alignment jig 140 can be installed on the collimator face as an accessory. The cones (i.e., the two through-holes) need not be aligned to the collimator axis of rotation.

Figure 33C:
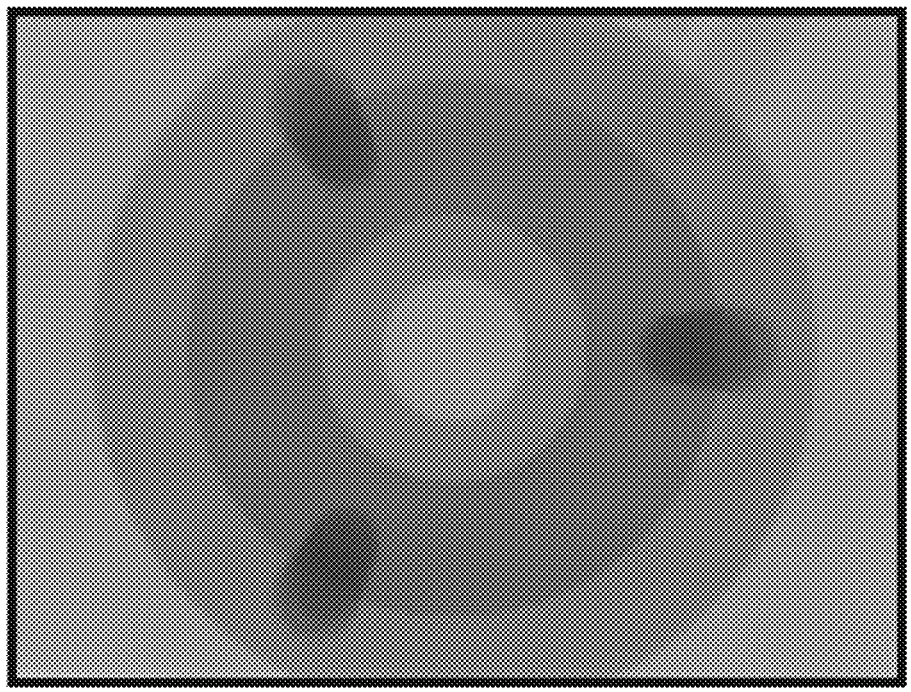
FIG. 33C illustrates an image obtained using the alignment mechanism of FIG. 33A.

Next, the gantry is positioned at a desired angle in Step 3, and the collimator is positioned to an initial angle in Step 4. The gantry angle can be defined as being at 180 degrees when the collimator is positioned at the top (head up), at 0 degrees when the collimator is positioned at the bottom (head down), and at 90 degrees when the collimator is on the right side (if the observer is standing in front of the machine, looking toward the gantry stand). Once the gantry and collimator positions are set, in Step 6, an image is acquired using the EPID 112. Generally, images at a set number of collimator angles are acquired. If the scheduled number of images is not yet acquired, the collimator is positioned to the next angle in Step 8 and another image is taken. This closed loop is repeated until all scheduled mages are acquired in Step 7. A typical image so acquired is shown in FIG. 33C.

Figure 33D:
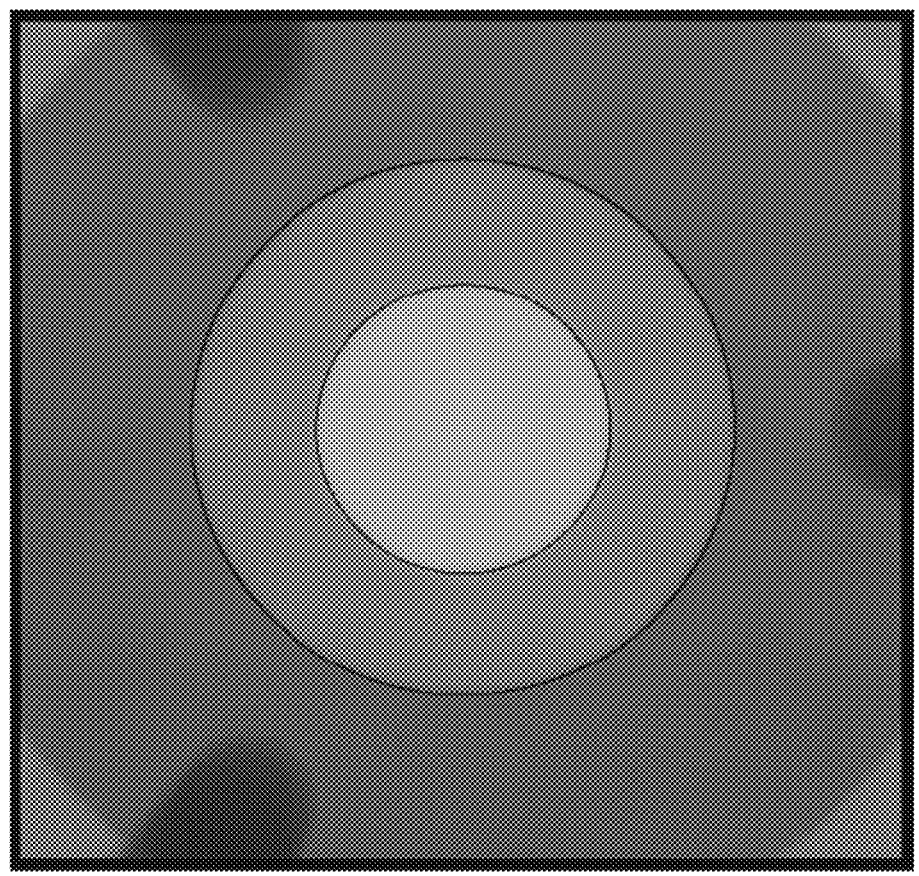
FIG. 33D illustrates a close-up of the image of FIG. 33C.

If it is determined in Step 7 that all scheduled images are acquired, the image processor of controller 120 measures, in Step 9, the position of the center of Cone #1 and the center of Cone #2 for each image. The images captures in step 6 are individually analyzed to find the circle centers. To find the exact center of each cone, an edge-detection method together with a best-fit circle algorithm, as described in detail above, and as shown in FIGS. 20-24 can be applied. Each image has two expected circles at a given locations and radii, as shown in FIG. 33C. Each circle is individually analyzed for edge and circle center, as shown in FIG. 33D.

In Step 10, the image processor provides a measure of data quality by analyzing the circle edge points captured in Step 9 recording the cone center locations in image coordinates. The image quality data represents the circularity of the image itself, as shown in FIG. 33D (FIG. 33D represents a close-up of the image with two circles to illustrate image processor output). The centers of all cone (Cone #1, Cone #2) images usually fall into a circular form due to the finite eccentricity between the cone edge and the collimator axis. A poor measure of data quality indicates an imaging problem or mechanical deviation of the circular hole in a cone due to damage, for example. This would signal erroneous data, halting the process until remedied. Thus, if image quality is poor in Step 10, the test needs to be redone or the jig 140 needs to be inspected for mechanical errors in Step 11. The process is halted in Step 12 until the problem is remedied.

The quality measure ($Q_{cir}$) can be calculated according to:

$$Q_{cir} = \text{stdev}(D_i) \quad \text{Eq. 22}$$

Where $D_i$ is the error distance between the best-fit circle and each edge point (i). The quality measure is a standard deviation value where a value of zero means all edge points are exactly on the circle and represents a perfect match. A threshold value can be set to determine an acceptable image. Alternatively, the quality metric can be based on maximum/minimum criteria with acceptance criteria base on one or more adjoining points exceeding a given threshold; the threshold can be previously determined according to desired process controls.

Figure 33E:
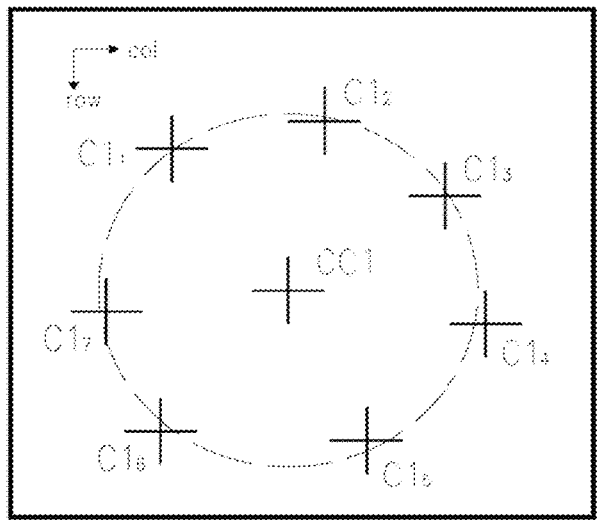
FIG. 33E illustrates the center of a best-fit circle fitting associated with a cone image center.

Continue to step 13 if it is determined in Step 10 that the image quality is good. In step 13, the centers of all Cone #1 circles are combined and a best-fit circle to those centers is calculated in Step 13, as shown in FIG. 33E. The centers of the individual cone images are designated as C1n, where n is the image number for Cone #1 images. The center of the best-fit circle is CC1 for Cone #1. The analysis is repeated for Cone #2 circle centers (C2n) and best-fit calculated center CC2.

Figure 33F:
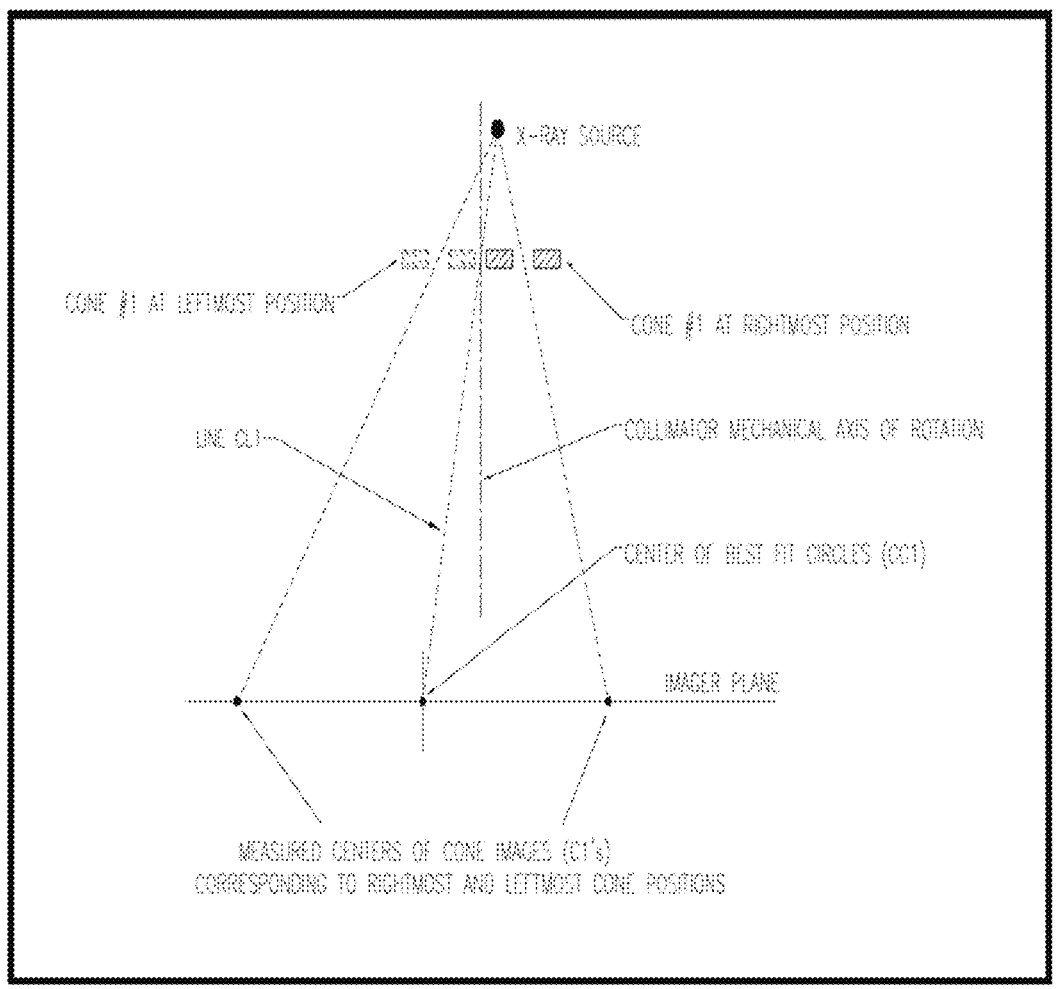
FIG. 33F illustrates a projection of the center of a cone of FIG. 33E onto the imager.

The quality fit (Q) is calculated according to:

$$Q = \text{stdev}(D_n) \quad \text{Eq. 23}$$

where Dn is the distance between CC1 (or CC2) and C1n (or C2n). CC1 (or CC2) is the projection onto the imager 112 of the point in space which is formed by the intersection of the collimator mechanical axis and the plane containing Cone #1 (or the plane containing Cone #2), as shown in FIG. 33F.

If all of the C1's lie in a perfect circle, the value of Q will be zero. The value of Q will increase as the C1's arrangement deviates from a circular form. Acceptable values for Q can be previously determined according to desired process control. Alternatively, the quality fit equation can be based on a maximum/minimum criteria with an acceptance criteria based on one or more adjoining points exceeding a given threshold; the threshold can be previously determined according to desired process controls. If the fit quality is not acceptable in Step 14, namely, if the Q value calculated is excessive, the test needs to be redone or the collimator bearing needs to be inspected for mechanical error in Step 15. In such a case, the process is halted in Step 16 until the problem is remedied. If the fit quality Q in Step 14 is acceptable, the X-ray source error in the transverse and radial positions is calculated in Step 17.

Figure 33G:
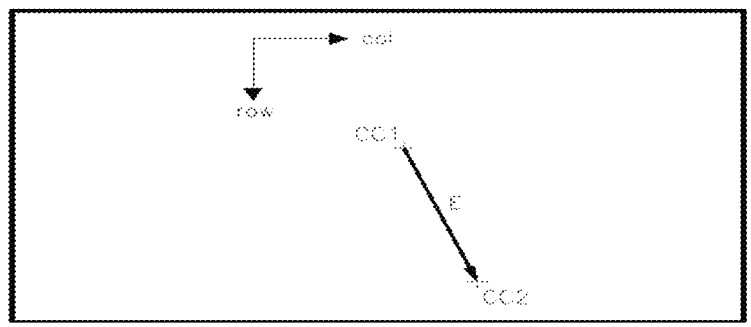
FIG. 33G illustrates an eccentricity vector computed between the imaging centers of the cones of FIG. 33A.
Figure 33H:
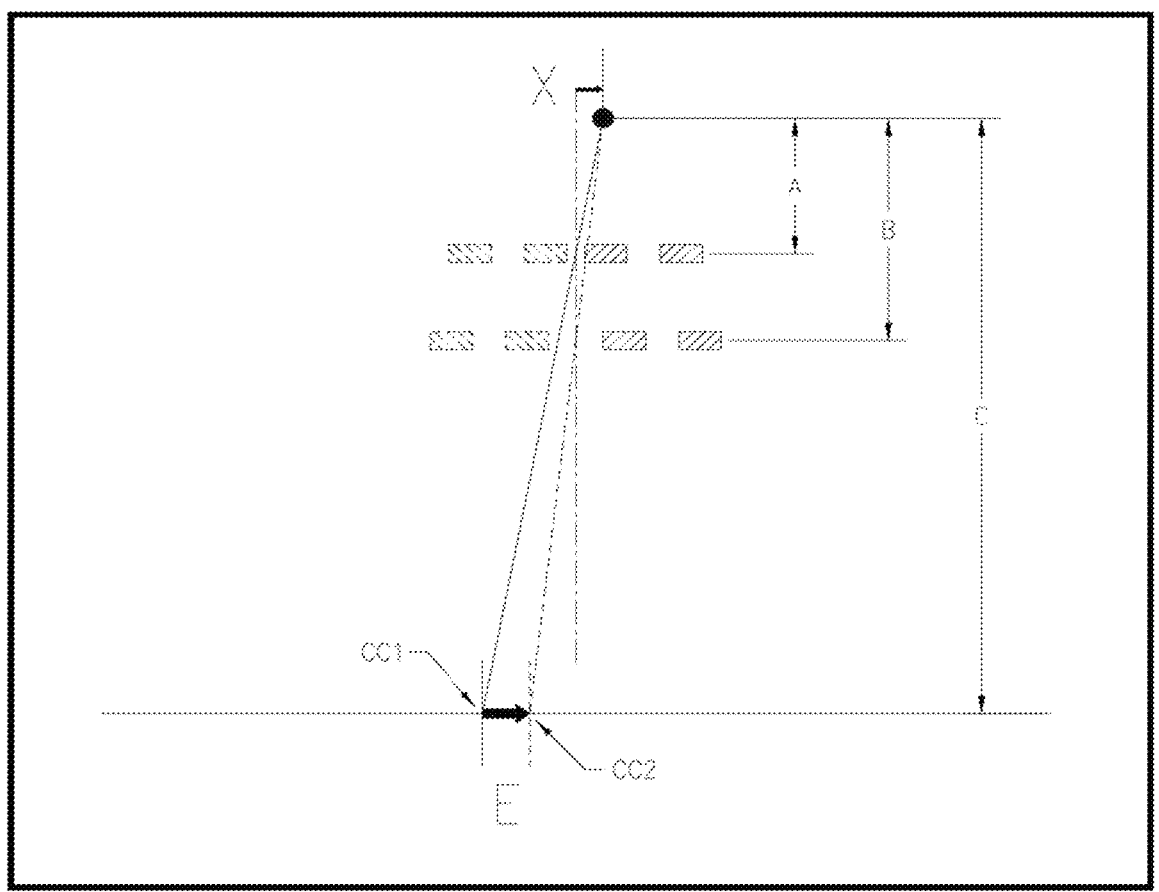
FIG. 33H illustrates a relationship between the eccentricity vector of FIG. 33G on the imager and a radiation source misalignment vector.

To calculate the X-ray source position error, first the difference between CC1 and CC2 needs to be determined. The difference between CC1 and CC2 represents the eccentricity vector in the image space E, as shown in FIG. 33G, and it is the scaled projection of the X-ray source misalignment vector X as shown in FIG. 33H. The relationship between E and X is a scale factor determined by lengths A, B, and C, and it is as follows:

$$E = X\left(\frac{C-A}{A} - \frac{C-B}{B}\right) \quad \text{Eq. 24}$$

Or, if solved in for X:

$$X = \frac{E*A*B}{C(B-A)} \quad \text{Eq. 25}$$

where A is the distance of Cone #1 from the X-ray source at the rightmost position, B is the distance of Con #2 from the X-ray source at the rightmost position, and C is the distance of the EPID 112 from the X-ray source. The row component of E generates the radial (Y axis) component of X (i.e., the R-pos error), and the column component of E generates the transverse (X axis) component of X (i.e, the T-pos error). It can be seen that equation xx matches equation 10 where $X=\epsilon_{\text{ооυρχ}\epsilon}$, $E=\delta_{cen}$, $A=D_{ujaw}$, $B=D_{mlc}$; and C=SSD 5. Calibration of X-ray Filters (Step S108)

After the beam angle steering coils are calibrated (i.e., after S106) and the radiation beam is aligned with the collimator axis of rotation (i.e., S107), the X-ray flattening filter 117 position is next calibrated in S108. A correctly located flattening filter generates a flattened radiation beam, which is characterized by a symmetric radiation beam profile. The radiation flattening filters 117 have specific geometries and are required to be precisely aligned to the radiation beam in order to generate flattened, and thus, symmetric radiation beams to the patient 101.

In S108, using the EPID and taking alternating image pairs, the symmetry can be computed and, based upon magnitude and orientation, the flattening filters 117 can be automatically moved until the desired symmetry has been achieved. In a closed control loop, it is possible for the system 100 to quickly and accurately align the flattening filters 117.

a. Calibration Process

Figure 34:
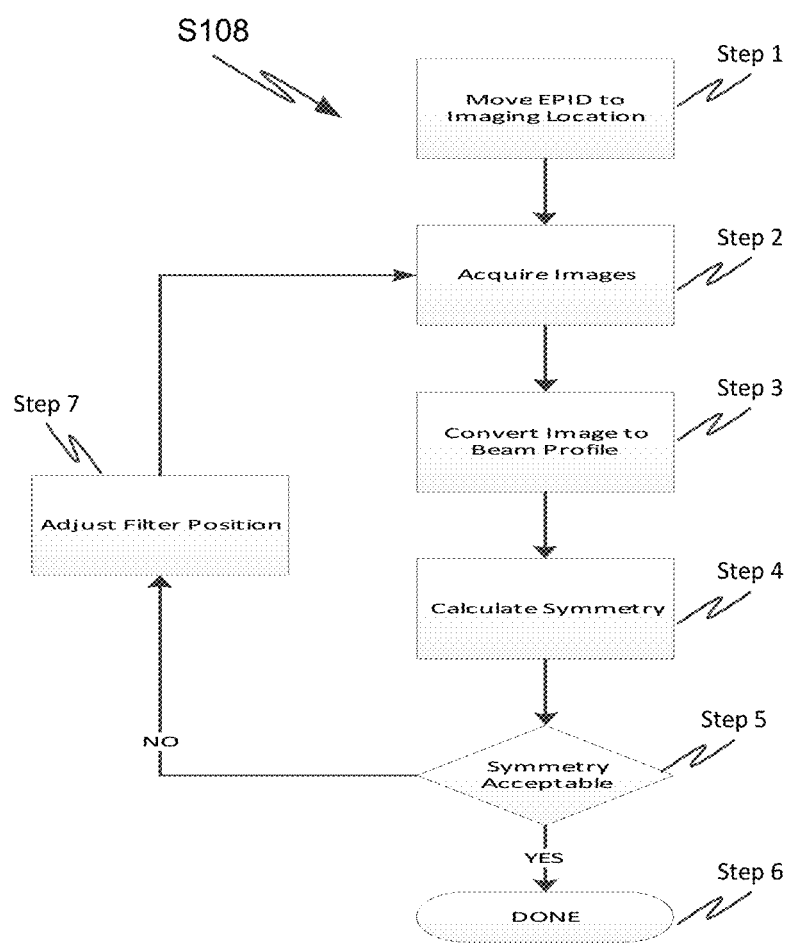
FIG. 34 illustrates a process flow for calibrating X-ray filters of a radiation treatment device according to one or more embodiments of the disclosed subject matter.

The X-ray filter calibration procedure S108 is illustrated in FIG. 34. Since a given system 103 can deliver multiple X-ray energies, each energy has its own flattening filter 117 which needs to be calibrated.

In Step 1, the EPID 112 is moved to an imaging location. The accuracy of locating the EPID 112 is not essential, since all images are analyzed relatively. During this step, the collimator jaws 121, 123, and optionally the MLC 125, are set so as to deliver a specific radiation field size. Then the flattening filters 117 are moved into a default flattening filter position. With this setup, a series of alternating image pairs are acquired in Step 2 using the EPID 112. The taking of alternating image pairs involves taking successive pairs of dark and flood field images. The image pairs are generally captured for a period of time (i.e., a number of image pairs or elapsed image acquisition time) and an average image is generated from the plurality of image pairs.

From the average image generated from the series of alternating image pairs, the beam profile symmetry is next calculated in Step 4. To calculate the beam profile symmetry, the image is first converted, using the normalized conversion map, into a radiation dose map in Step 3, then, if desired, an image filtering algorithm, such as, but not limited to, mean, median, Gaussian, or a combination of median and Gaussian filtering algorithms are applied to remove imaging errors. The symmetry of the delivered radiation beam can be computed using any one of the symmetry calculation algorithm described in detail above. After the beam symmetry is calculated from the EPID image, the symmetry is evaluated in Step 5 to determine whether it falls within a prescribed symmetry range. The symmetry of the beam is analyzed in the transverse (X-axis) and the radial (Y-axis) directions.

If the radiation beam symmetry does fall within the prescribed range, the position of the X-ray flattening filters 117 need not be adjusted and the calibration is complete. The calibration process S108 is then stopped at Step 6. If the determined beam symmetry does not fall within the prescribed range, the position of the X-ray flattening filters 117 is adjusted in Step 7. Since the magnitude and direction of the asymmetry is directly proportional to the location of the flattening filter 117 with respect to the radiation beam, using the asymmetry information, the position of the filters 117 can be adjusted in transverse (X) and radial (Y) axis direction until the symmetry is acceptable. The multiplication factor or exact distance adjustment for a given asymmetry amount can either be calculated or empirically determined using any available calculation methods.

After an initial adjustment in Step 7, a series of alternating image pairs are again taken with the EPID 112 and the symmetry of the radiation beam again calculated and evaluated. This automatic loop is repeated until the symmetry (for both axes) of the radiation beam is within specification. At that point, the X-ray flattening filters 117 are considered to be tuned and the delivered radiation beam is symmetric. At this point, the calibration process S100 can move on to Step S109.

b. Calibration Algorithm (Symmetry Calculation)

The symmetry of the delivered radiation beam can be computed using a plurality of algorithms, such as, but not limited to, the 2-Point difference method, Area (2D) method, 2D slope deviation method, Volume (3D) method, 2D centroid method, and 3D centroid method, as described in detail above.

6. X-ray Enemy Adjustment (Step S109)

Each delivered X-ray radiation energy from the radiation treatment device 103 needs to be adjusted to assure that it is at the desired energy. Adjusting the radiation energy can be done by adjusting the bend magnet shunt current value. Using an EPID 112, and taking images using the alternating image pair acquisition method, the radiation beam profile can be captured. From the radiation beam profile, the radiation beam energy can be calculated. The flatness of the diagonal cross section of the radiation beam is directly proportional to the energy level (or depth dose). The EPID image of the radiation beam profile shares this proportional relationship to beam energy. Therefore, from the EPID images, the energy error can be calculated and used to adjust the energy output by adjusting the bend magnet shunt current until the desired energy output is achieved.

a. Calibration Process

Figure 35:
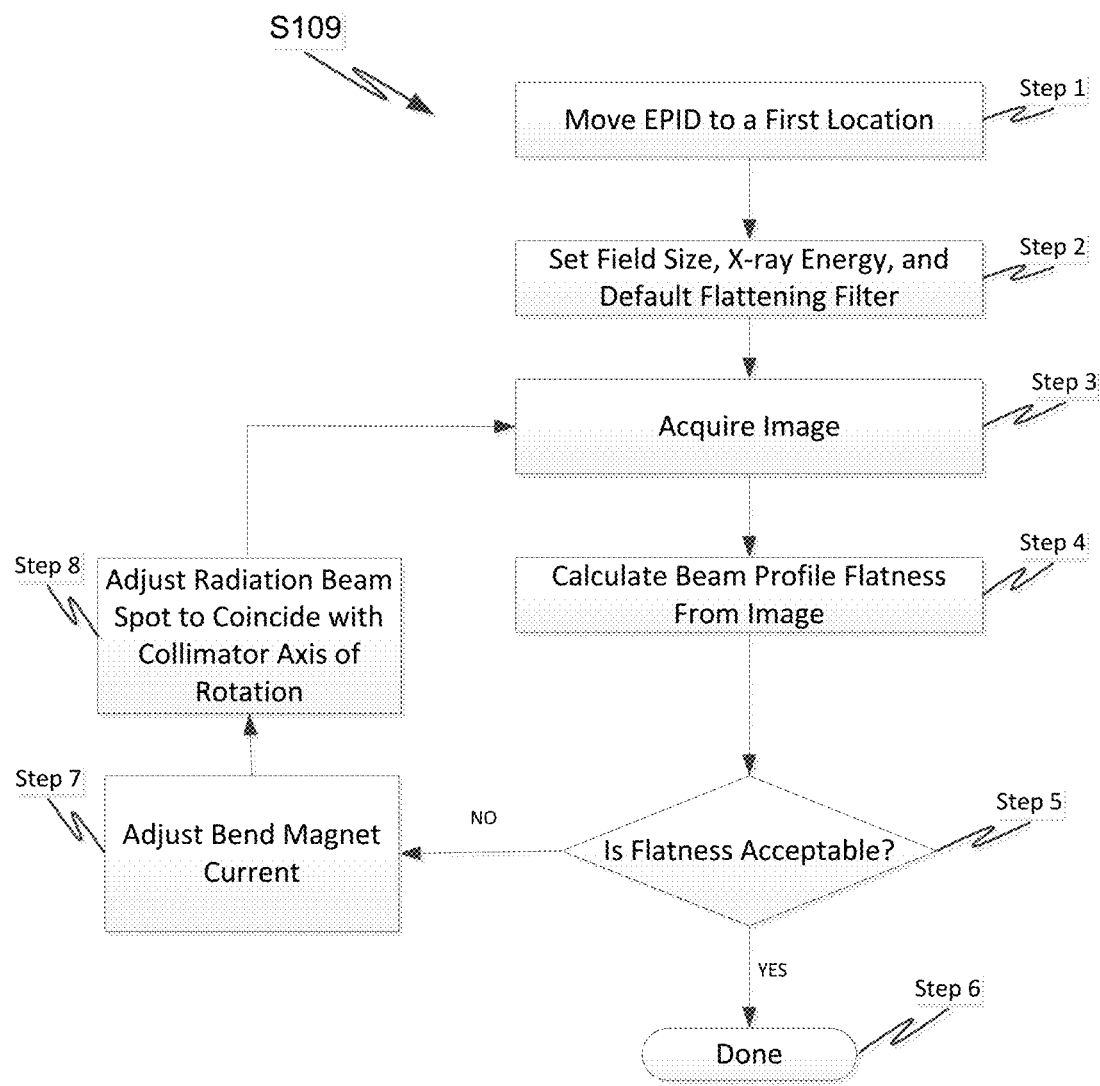
FIG. 35 illustrates a process flow for X-ray energy adjustment according to one or more embodiments of the disclosed subject matter.

The X-ray energy adjustment process S109 is illustrated in FIG. 35. Prior to applying the X-ray energy adjustment process, it is important that the angle steering calibration step S106, position steering calibration step S107, and the flattening filter calibration step S108 are completed.

In Step 1, the EPID 112 is moved to an imaging location. The accuracy of locating the EPID 112 is not critical since all images are analyzed relatively. In Step 2, the bend magnet shunt current is adjusted in order to deliver a desired X-ray energy output. Each delivered X-ray radiation energy from the device 103 needs to be adjusted to assure that it is at the desired energy within a specified range. During this step, the collimator jaws 121, 123, and optionally MLC 125, are set so as to deliver a specific radiation field size, and the flattening filters 117 are moved into the calibrated flattening filter position. With this setup, a series of alternating image pairs are acquired in Step 3 using the EPID 112. The taking of alternating image pairs involves taking successive pairs of dark and flood field images. The image pairs are generally captured for a period of time (i.e., a number of image pairs or elapsed image acquisition time), and an average image is generated from these image pairs.

From the average image generated from the series of alternating image pairs and the conversion to the beam profile, flatness is next calculated in Step 4. To calculate the beam profile flatness, the image is first converted into a radiation dose map using the normalized conversion map, then, if desired, an image filtering algorithm, such as, but not limited to, mean, median, Gaussian, or a combination of median and Gaussian filtering algorithms are applied to remove imaging errors. The flatness of the delivered radiation beam can be computed using a flatness calculation algorithm described below. After the beam flatness is calculated from the EPID image, the flatness is evaluated in Step 5 to determine whether it falls within a prescribed flatness range. The flatness of the beam is analyzed along the two diagonal axes (45 degrees from X and Y axes). For a given paired energy and flattening filter 117, the flatness value of the diagonal profile is proportional to the delivered beam energy. The proportional factor is energy dependent and can be empirically determined.

If the flatness is acceptable, the output energy is acceptable and the tuning is completed in Step 6. If the beam flatness is not acceptable, the bend magnet shunt current value can be automatically adjusted based upon the captured flatness error to correct the output energy. After any bend magnet current adjustment, the angle steering may need to be adjusted (i.e., repeat step S106) and the radiation beam spot may need to be re-adjusted for coincidence with the collimator axis of rotation (i.e., repeat step S105). After the radiation beam is adjusted to be coincident with the collimator axis of rotation, a series of alternating image pairs are again taken with the EPID 112 and the flatness of the radiation beam again calculated and evaluated. This automatic loop is repeated until the flatness (for both diagonal axes) of the radiation beam is within specification. At that point, the delivered radiation beam is considered to have the specified energy, and the energy adjustment process S100 can move on to Step S110.

b. Calibration Algorithm (Beam Flatness Calculation)

Figure 36:
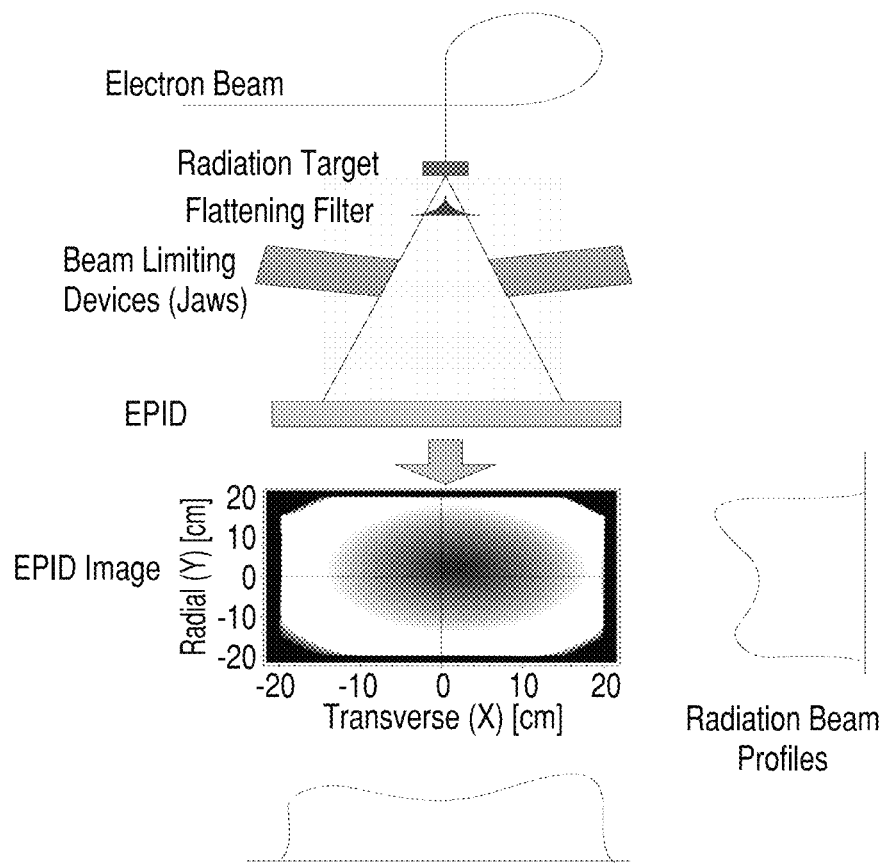
FIG. 36 illustrates a 2D map aggregate according to one or more embodiments of the disclosed subject matter.
Figure 37:
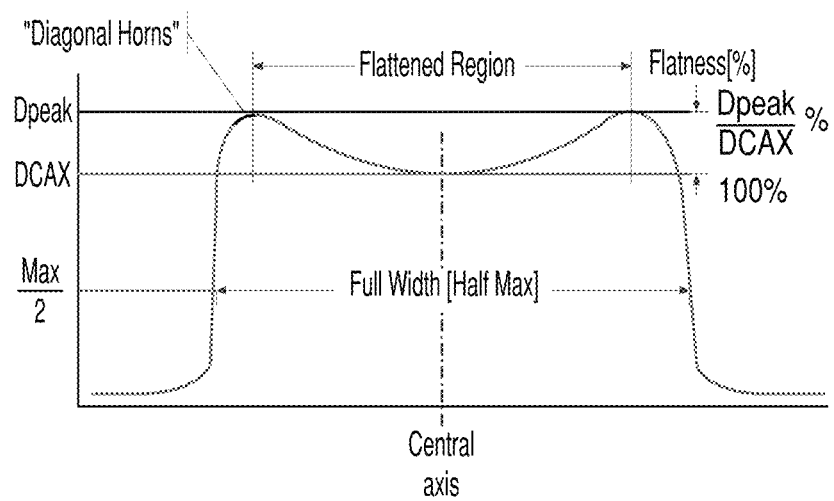
FIG. 37 illustrates a radiation beam profile according to one or more embodiments of the disclosed subject matter.

To calculate the beam profile flatness along the two diagonal axes (45 degrees from X and Y axes), the analysis starts with the radiation beam profile, as shown in FIGS. 36, 37. FIG. 37 shows the annotated terms and shape of a typical radiation profile beam. The diagonal horns indicate deviations from the beam flatness. Taking the radiation dose at the center of the beam DCAX and capturing the maximum peak values ($D_{peak}$), the beam flatness can be calculated according to:

$$\text{Flatness } [\%] = \frac{D_{peak}}{DCAX} * 100 \qquad \text{Eq. 26}$$

c. Alternative Embodiment

In an alternative embodiment, the radiation beam energy can be determined and adjusted using a calibration device, such as a calibration phantom, positioned on the EPID 112. For a given radiation energy and material, the radiation attenuation (i.e., the drop in radiation) for a given material thickness is known. Therefore, by capturing the radiation dose through the phantom using the EPID, the actual energy delivered can be calculated using a back-calculation technique. To detect the radiation dose, one or more dark field/flood field alternating images are acquired using the EPID by illuminating a calibration phantom having a known material and known material thickness. From the generated images, the radiation dose is determined. Knowing the radiation dose, the phantom material and thickness, and the radiation attenuation for a given material thickness, the radiation energy can be calculated. If the calculated radiation energy is not within an acceptable range, the bend magnet shunt current value can be automatically adjusted based upon the captured energy error to correct the output energy. By using calibration phantoms with different materials and material thicknesses, the accuracy of detection across many different energy ranges can be improved.

7. Scattering Foil Alignment (Step S110)

In order to achieve a symmetric electron beam profile, the position of the radiation scattering foil 127 needs to be calibrated. The radiation scattering foil 127 has a specific geometry for a given treatment energy and is a part of the radiation treatment device 103. It is required that it be precisely aligned to the electron beam in order to generate a symmetric electron beam which is delivered to the patient 101. In the imaging-based calibration method S110, the scattering foil 127 is moved until the electron beam has achieved a desired symmetry. This process, S110, is repeated for each scattering foil 127 and respective energy. A radiation device 103 typically has multiple available foils and respective energies. Using an EPID and taking alternating image pairs, it is possible to capture and compute the symmetry, and then, based upon magnitude and orientation, automatically move the scattering foil 127 until the desired symmetry has been achieved. In a closed control loop, the system 100 can quickly and accurately align the scattering foil 127.

a. Calibration Process

Figure 38:
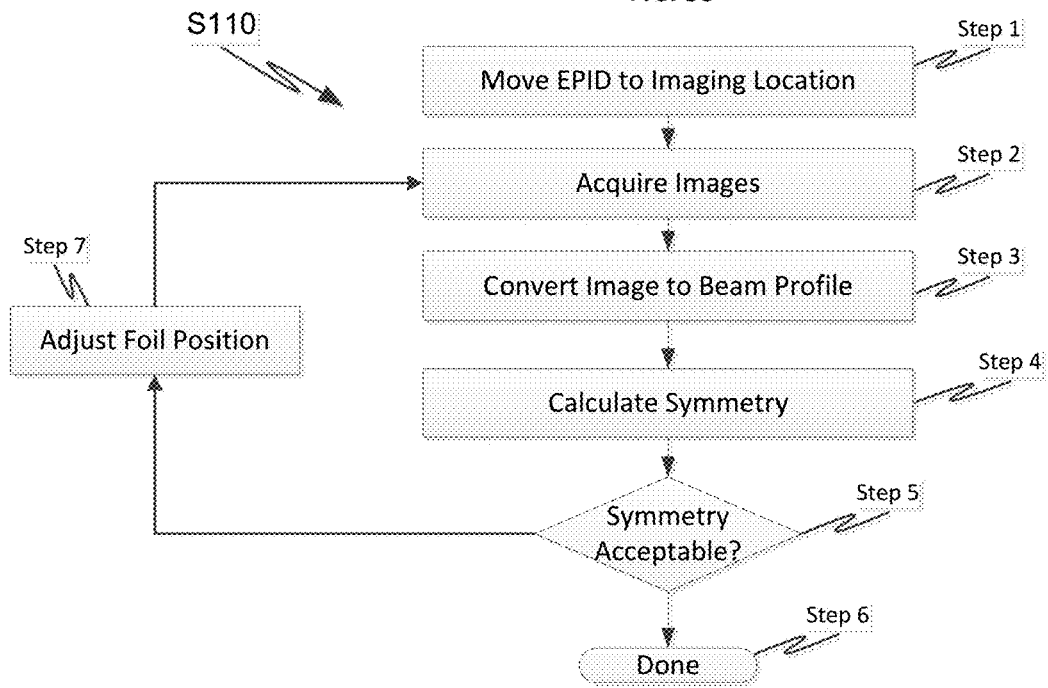
FIG. 38 illustrates a process flow for calibrating the scattering foils of a radiation treatment device according to one or more embodiments of the disclosed subject matter.

The scattering foil alignment process S110 is illustrated in FIG. 38. Since a given system 103 can deliver multiple electron energies, and since each of the energies is associated with its own scattering foil 127, each scattering foil 127 needs to be separately aligned.

In Step 1, the EPID 112 is moved to an imaging location. The accuracy of locating the EPID 112 is not essential, since all images are analyzed relatively. During this step, the collimator jaws 121, 123, and optionally MLC 125 are set to deliver a specific radiation field size. In some cases, an electron beam applicator (cone) 129 is affixed to the collimator system 110 to improve the image clarity by making the edge penumbra more distinct and clear. Then the scattering foil 127 is moved into a default position. With this setup, a series of alternating image pairs are acquired in Step 2 using the EPID 112. The taking of alternating image pairs involves taking successive pairs of dark and flood field images. The image pairs are generally captured for a period of time (i.e., a number of image pairs or elapsed image acquisition time) and an average image is generated from the image pairs.

From the average image generated from the series of alternating image pairs, the electron-beam profile symmetry is next calculated in Step 4. To calculate the beam profile symmetry, the image is first converted into a radiation dose map using the normalized conversion map (Step 3), then, if desired, an image filtering algorithm, such as, but not limited to, mean, median, Gaussian, or a combination of median and Gaussian filtering algorithms are applied to remove imaging errors. The symmetry of the delivered electron-beam can be computed using any one of the symmetry calculation algorithm described above. Once the electron-beam symmetry is calculated from the EPID image, the symmetry is evaluated in Step 5 to determine whether it falls within a prescribed symmetry range. The symmetry of the electron-beam is analyzed in both the transverse (X axis) and the radial (Y-axis) directions. If the electron-beam symmetry does fall within the prescribed range, the position of the scattering foil 127 need not be adjusted and the calibration is complete. The calibration process S110 is then stopped in Step 6. If the determined electron-beam symmetry does not fall within the prescribed range, the position of the scattering foil 127 is adjusted in Step 7. Since the magnitude and direction of the asymmetry is directly proportional to the location of the scattering foil 127 with respect to the electron-beam, using the asymmetry information, the position of the scattering foil 127 can be adjusted in X and Y axes until the symmetry is acceptable. The multiplication factor or exact distance adjustment for a given asymmetry amount can either be calculated or empirically determined.

After an initial adjustment in Step 7, a series of alternating image pairs are again taken with the EPID 112 and the symmetry of the electron-beam again calculated and evaluated. This automatic loop is repeated until the symmetry of the electron-beam is within specification. At that point, the scattering foil 127 is considered to be tuned and the delivered electron-beam is symmetric. At this point, the calibration process S100 can move on to Step S111, for a given energy.

Although the scattering foil calibration procedure described above used electron-beams as the radiation field, and an EPID 112 as the imager, in an alternative embodiment, the calibration procedure can be implemented using the a modified EPID 112' or 112" which may offer better detection sensitivity for electron radiation compared to EPID 112 which is optimized for X-ray radiation.

b. Calibration Algorithm (Symmetry Calculation)

The symmetry of the delivered electron-beam can be computed using a plurality of algorithms, such as, but not limited to, the 2-Point difference method, area (2D) method, 2D slope deviation method, Volume (3D) method, 2D centroid method, and 3D centroid method, as described in detail above.

8. Electron-Beam Energy Adjustment (Step S111)

Each delivered electron-beam energy from the radiation treatment device 103 needs to be adjusted to assure that it is at the desired energy within a specified range. Using an EPID and taking images using the alternating image pair acquisition method, the electron-beam profile can be captured. From the radiation beam profile, the electron-beam energy can be calculated. The flatness of the diagonal cross section of the electron-beam is directly proportional to the energy level (or depth dose). The EPID image of the electron-beam profile shares this proportional relationship to electron-beam energy. Therefore, from EPID images, the electron-beam energy error can be calculated and used to adjust the energy output by adjusting the bend magnet shunt current until the desired energy output is achieved.

a. Calibration Process

Figure 39A:
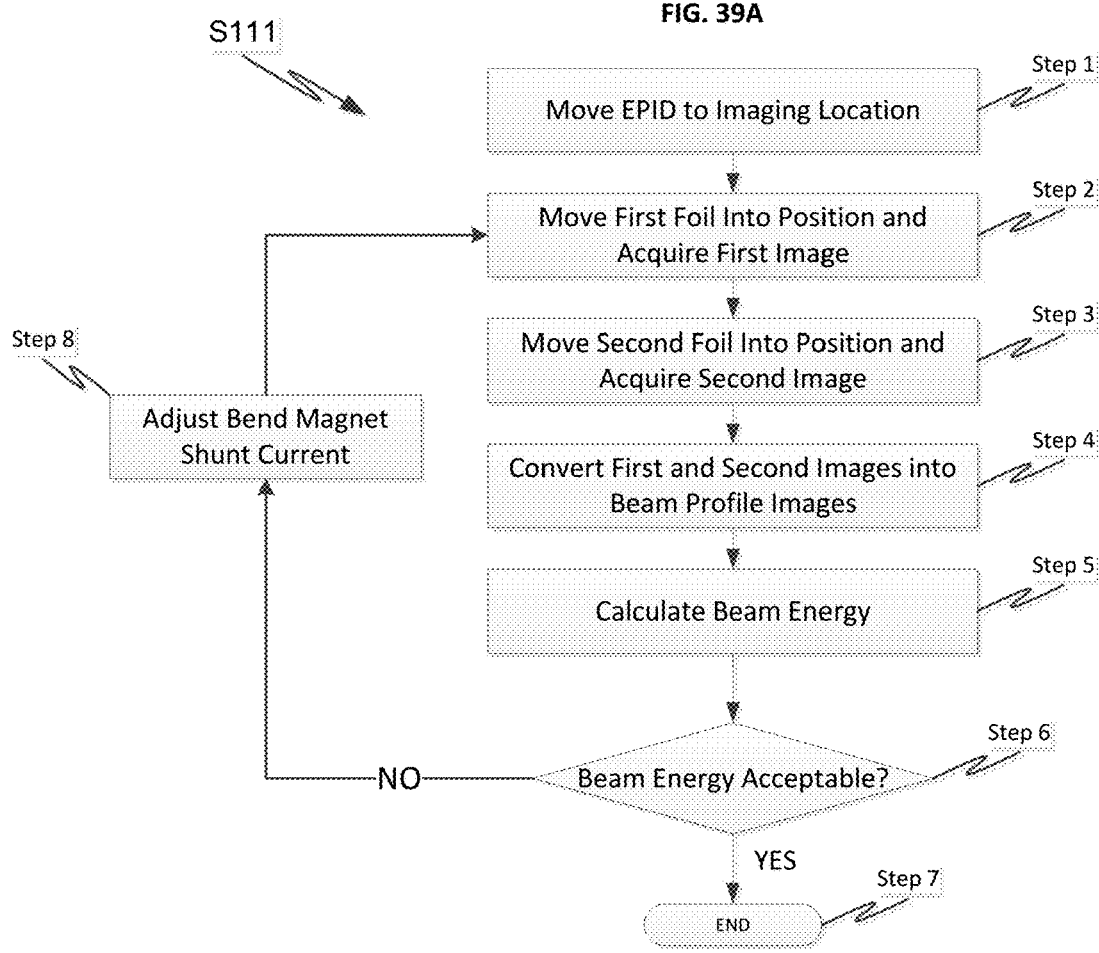
FIG. 39A illustrates a process flow for electron-beam adjustment according to one or more embodiments of the disclosed subject matter.

The electron beam energy adjustment process S111 is illustrated in FIG. 39A. Multiple (at least two) scattering foils 127, each having a specific thickness, material composition, and geometry, are placed in between the electron-beam and the EPID 112, and the EPID 112 is used to capture the electron-beam profile for each scattering foil 127. By comparing the relative image intensities obtained for each scattering foil 127, the exact energy delivered can be determined. This allows for adjustment and re-checking of the energy level in a closed iterative control loop, until the desired energy value has been achieved. FIG. 39A illustrates this energy verification and adjustment procedure S111. In Step 1 the EPID 112 is moved to an imaging location. The EPID 112 is moved along the vertical direction as close to the radiation source as possible, in order to minimize electron scatter. Alternatively, or in conjunction, an electron beam applicator (cone) 129 can be installed to improve image edge detection quality. In Step 2, a first scattering foil 127 is moved into position and an alternating pair of field/flood images is acquired using the EPID 112. The taking of alternating image pairs involves taking successive pairs of dark and flood field images. The image pairs are generally captured for a period of time (i.e., a number of image pairs or elapsed image acquisition time) and an average (integrated) first image is generated from the image pairs. In Step 3, a second scattering foil 127 is moved into position and an alternating pair of field/flood images is acquired using the EPID 112. The taking of alternating image pairs involves taking successive pairs of dark and flood field images. The image pairs are generally captured for a period of time (i.e., a number of image pairs or elapsed time) and an average (integrated) second image is generated from the image pairs. In Step 4, the first and second images are converted into beam profile images using the normalized conversion map, then, if desired, an image filtering algorithm, such as, but not limited to, mean, median, Gaussian, or a combination of median and Gaussian filtering algorithms are applied to remove imaging errors.

The beam energy of the delivered electron-beam can be calculated in Step 5 using the following equation:

$$HVL = \frac{\ln(2^{t1-t2})}{\ln\left(\frac{I2}{I1}\right)} \qquad \text{Eq. 27}$$

Where, I1 and I2 are the image intensities for the first and second scattering foils 127, respectively; t1 and t2 are the thicknesses of the first and second scattering foils, respectively; (HVL) is the half value layer of the scattering foil material. The intensities I1 and I2 can be average intensities over corresponding central image regions.

Since the energy of the incident electron-beam is directly related to the half value layer (HVL), determining the HVL from the known parameters, such as the image intensities I1 and I2 and the individual thicknesses of the first and second scattering foils 127, the electron-beam energy can be inversely determined.

After the electron-beam energy is computed from the beam profile images, the beam energy is evaluated in Step 6 to determine whether it falls within a prescribed energy range. If the energy is acceptable, there is no adjustment of the bend magnet shunt current needed and the tuning is completed in Step 7. If the beam energy is not acceptable, the bend magnet shunt current can be automatically adjusted to correct the output energy in Step 8 based upon the magnitude of error.

After the adjustment Step 8 has completed, the process repeats starting with Step 2 through Step 6 where a series of alternating image pairs are again taken with the first scattering foil 127 in a first position and then with the second scattering foil 127 in a second position, and the energy of the electron-beam again calculated and evaluated. This automatic loop is repeated until the energy of the electron-beam is within specification. At that point, the delivered electron-beam is considered to have the specified energy, and the energy adjustment process S100 can move on to Step S112.

Although the electron-beam energy calibration procedure S111 uses electron-beams as the radiation field, and an EPID 112 as the imager, in an alternative embodiment, the calibration procedure can be implemented with a modified EPID 112' or 112", which may offer better detection sensitivity for electron radiation compared to EPID 112 which is optimized for X-ray radiation.

c. Alternative Embodiment

Figure 39B:
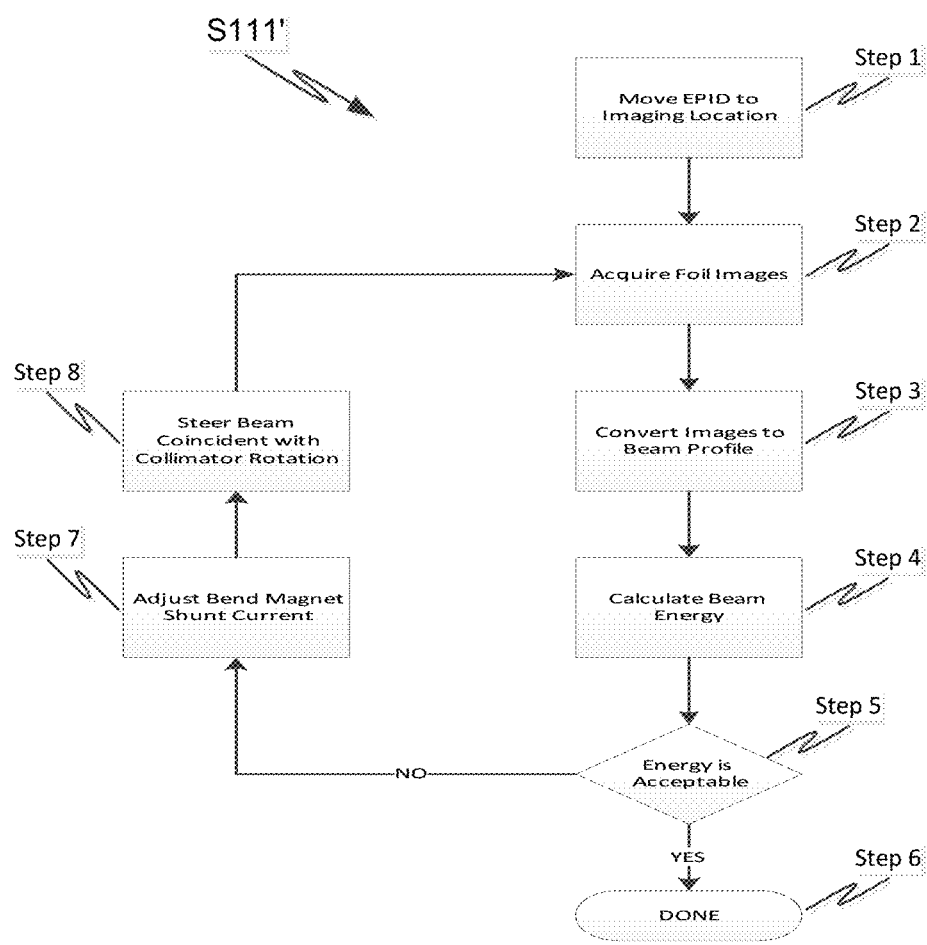
FIG. 39B illustrates an alternative process flow for electron-beam adjustment according one or more embodiments of the disclosed subject matter.

An alternative electron-beam energy adjustment process S111' is illustrated in FIG. 39B. In Step 1, the normalized EPID 112 is moved to an imaging location. The accuracy of locating the EPID 112 is not essential, since all images are analyzed relatively. In Step 2, the bend magnet shunt current is adjusted in order to deliver a desired electron-beam energy output. Each delivered electron-beam energy from the device 103 needs to be adjusted to assure that it is at the desired energy within a specified range. During this step, the collimator jaws 121, 123, and optionally the MLC 125, are set so as to deliver a specific radiation field size, and the scattering foil 127 is moved into a default position. With this setup, a series of alternating image pairs are acquired in Step 3 using the normalized EPID 112. The taking of alternating image pairs involves taking successive pairs of dark and flood field images. The image pairs are generally captured for a period of time (i.e., a number of image pairs or elapsed image acquisition time) and an average image is generated from the image pairs.

From the average image generated from the series of alternating image pairs, the electron-beam profile flatness is next calculated in Step 4. To calculate the electron-beam profile flatness, the image is first converted into a radiation dose map using the normalized conversion map, then, if desired, an image filtering algorithm, such as, but not limited to, mean, median, Gaussian, or a combination of median and Gaussian filtering algorithms are applied to remove imaging errors. The flatness of the delivered radiation beam can be computed using a flatness calculation algorithm described below. Once the beam flatness is calculated from the EPID image, the flatness is evaluated in Step 5 to determine whether it falls within a prescribed flatness range. The flatness of the electron-beam is analyzed along the two diagonal axes (45 degrees from X and Y axes). Per energy and scattering foil 127, the flatness value of the diagonal profiles is proportional to the delivered electron-beam energy. The proportional factor is energy dependent and can be empirically determined.

If the beam flatness is acceptable, the output electron-beam energy is acceptable and tuning is completed in Step 6. If the beam flatness is not acceptable, the bend magnet shunt current value can be automatically adjusted to correct it. After an initial bend magnet current adjustment, the radiation beam spot may need to be re-adjusted to be coincident with the collimator axis of rotation (i.e., repeat step S105). After the radiation beam is adjusted to be coincident with the collimator axis of rotation, a series of alternating image pairs are again taken with the EPID 112 and the flatness of the electron-beam again calculated and evaluated. This automatic loop is repeated until the flatness (for both diagonal axes) of the electron-beam is within specification. At that point, the delivered electron-beam is considered to have the specified energy, and the energy adjustment process S100 can move on to Step S112.

Although the electron-beam energy calibration procedure described above used electron-beams as the radiation field, and an EPID 112 as the imager, in an alternative embodiment, the calibration procedure can be implemented using a modified EPID 112' or 112".

b. Calibration Algorithm (Electron-Beam Flatness Calculation)

To calculate the beam profile flatness along the two diagonal axes (45 degrees from X and Y axes), the analysis is similar to the X-ray profile flatness described in detail above. The radiation beam profile is analyzed to determine the diagonal horns, the dose at center of the beam DCAX, and the maximum peak values ($D_{peak}$). Taking the radiation dose at the center of the beam DCAX and capturing the maximum peak values ($D_{peak}$), the electron-beam flatness can be calculated according to:

$$\text{Flatness } [\%] = \frac{D_{peak}}{DCAX} * 100 \qquad \text{Eq. 28}$$

9. Ionization Chamber Calibration (Step S112)

In the setup sequence of the radiation treatment device 103, it is important to calibrate the ionization chamber 119, which is used as the internal dosimeter, to read accurately. Thus, in S112, the ionization chamber 119 is calibrated for radiation dose linearity. The method of using an EPID 112 to calibrate the ionization chamber 119 for dose linearity includes making a one-time calibration between the EPID 112 and a calibrated dosimeter. This is necessary in order that the images obtained with a given EPID 112 is corrected for single device behaviors of the electronics, inhomogeneous pixel sensitivities, scattering in the detector, and the panel's complex energy response.

To calibrate the EPID 112, the EPID 112 is positioned at a known distance from the radiation source. A solid water phantom can be positioned in between the radiation source and the EPID 112 at a known location. The solid water phantom can be any available phantom that can be used for photon and electron beam calibrations including relative ionization, depth dose measurements, and absolute calibrations without the need for correction and scaling factors. The water phantom scatters and attenuates diagnostic and radiotherapy range X-rays the same way as water for the same depth and exposure duration. The phantom can be a phantom which was molded and accurately machined into standard dimensions to achieve accurate calibrations within 1% of the true dose. The phantom could be made of epoxy resins and powders to control density and radiation properties, and can have dimensions in the order of 50×50 cm and a thickness from 0.5 to 20 cm, for example. The type and dimension of the phantom is not a limiting factor and any other phantoms with known dimensions and composition could be used for the calibration of the EPID 112.

After the phantom is positioned, a measurement is made using the EPID 112. Using the same set-up, a calibrated dosimeter, such as an ion chamber, for example, is positioned so as to have its central axis at the EPID panel's height, and a measurement is also made using the calibrated ion chamber. The measurements by the EPID and the calibrated ion chamber are next compared to each other. A plurality of measurements can be made using both the ion chamber and the EPID for different phantom thicknesses and the responses compared to each other. By comparing the measurements, the ion chamber is used to calibrate each flat panel measurement leading to a calibration curve indicating the calibrated EPID measurement.

It is similarly possible to create this relationship without a phantom between the radiation source and EPID 112. In either case, the relationship will need to be established for all treatment energies for which the ionization chamber 119 needs to be calibrated.

After the relationship between the EPID's response and the calibrated ion chamber's response has been established, the now calibrated EPID 112 can be used to make a comparison between the radiation dose measured by the ionization chamber 119 and the radiation dose measured by the calibrated EPID 112. If the difference between the two falls within a prescribed range, the ionization chamber 119 need not be calibrated. However, if the difference between two measurements does not fall within a prescribed range, the ionization chamber 119 needs to be calibrated with the value from the EPID 112.

10. Ionization Chamber Symmetry Calibration (Step S113)

Figure 40:
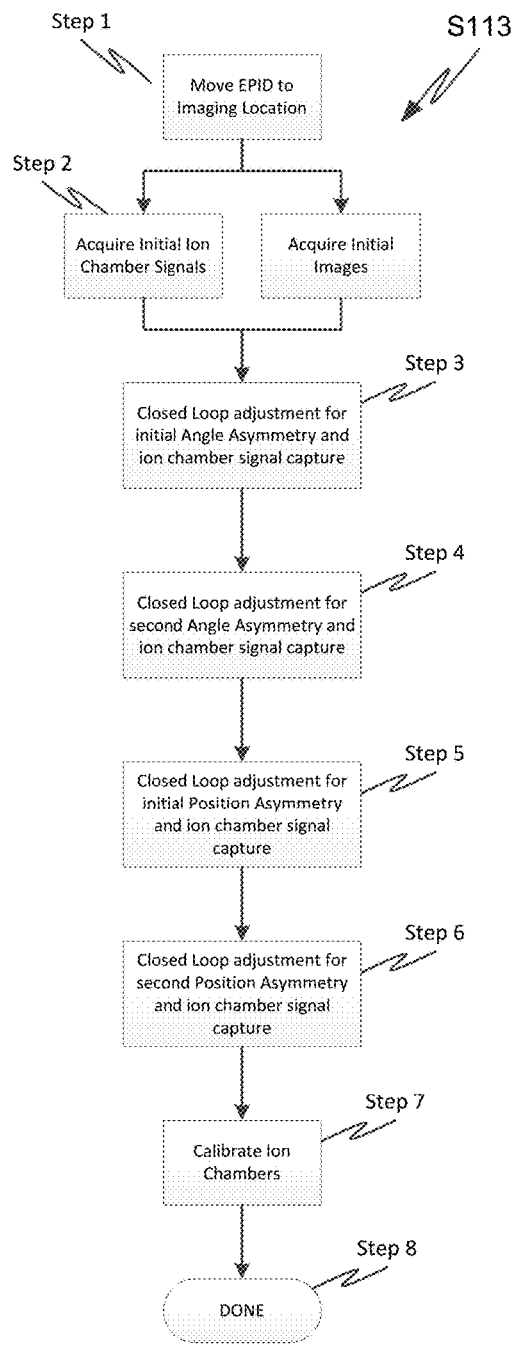
FIGS. 40-40B illustrate a process flow for calibrating the ionization chamber of a radiation treatment device according to one or more embodiments of the disclosed subject matter.
Figure 41:
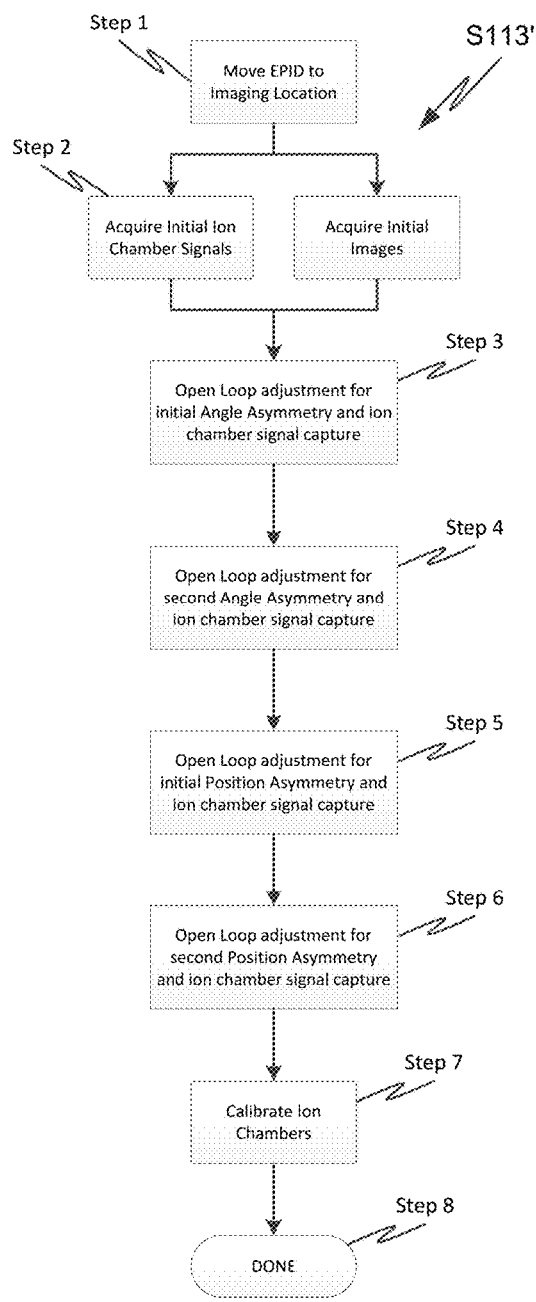
FIGS. 41-41B illustrate an alternative process flow for calibrating the ionization chamber of a radiation treatment device according one or more embodiments of the disclosed subject matter.

The internal dosimeter, such as the ionization chamber 119, of the radiation treatment device 103, has at least eight (8) main detection zones. These zones are configured in pairs: 1) symmetry due to angle in the radial (Y) axis; 2) symmetry due to angle in the transverse (X) axis; 3) symmetry due to position in the radial (Y) axis; and 4) symmetry due to position in the transverse (X) axis. In order to read accurately in each of the four zones, the ionization chamber 119 needs to be calibrated. A process S113 to calibrate the ionization chamber to correctly read the radiation beam symmetry in all four zones using an EPID 112 is illustrated in FIG. 40. An alternative method is shown in FIG. 41 as process S113'.

In Step 1 of the calibration process S113, a normalized EPID 112 is positioned at a desired position, central to the radiation beam axis, typically at 100 cm. Then in Step 2, a series of alternating image pairs are acquired using the EPID 112. The taking of alternating image pairs involves taking successive pairs of dark and flood field images. The image pairs are generally captured for a period of time (i.e., a number of image pairs or elapsed time) and an average integrated image is generated from the image pairs. While the images are acquired using the EPID 112 in Step 2, the ionization chamber 119 also captures the dosimeter values.

Figure 40A:
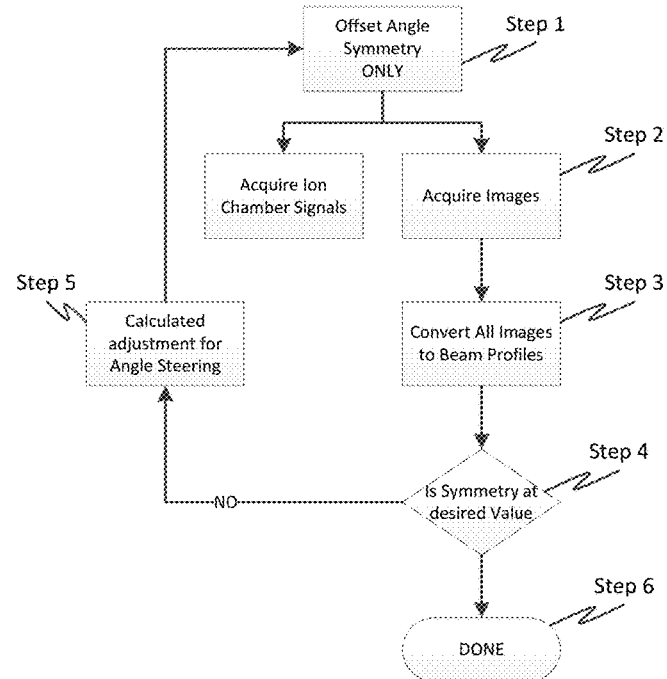

In Step 3, a closed loop procedure, as shown in FIG. 40A, is employed to achieve an initial value of desired asymmetry using the EPID 112 all while capturing the ionization chamber 119 dosimeter values.

The closed loop procedure, FIG. 40A, is executed as follows. In Step 1, expected asymmetries are introduced into the radiation beam profile by systematically varying the 2R (radial) and 2T (transverse) angle steering coil currents. This allows for the introduction of an asymmetry error of an expected magnitude. Then in Step 2 a series of alternating image pairs are acquired using the EPID 112. While the images are acquired using the EPID 112 in Step 2, the ionization chamber 119 also captures the dosimeter values. In Step 3, each of the integrated images is converted to a beam profile using the normalized conversion map. In Step 4, the symmetry for each beam profile can be computed using any one of the symmetry calculation algorithm described above. If the symmetry matches the desired amount, the process in FIG. 40A proceeds to Step 6 and is complete. If the symmetry is not within the desired range, the process in FIG. 40A goes to Step 5 where adjusted steering angle values are calculated based upon the actual symmetry value taken from the EPID 112 radiation beam images. This adjustment is used in Step 1 where iteration through Step 6 is made to achieve the desired asymmetry.

In Step 4 of process S113, the same closed loop procedure as shown in FIG. 40A is applied to achieve a second value of desired asymmetry using the EPID 112 all while capturing the ionization chamber 119 dosimeter values.

Figure 40B:
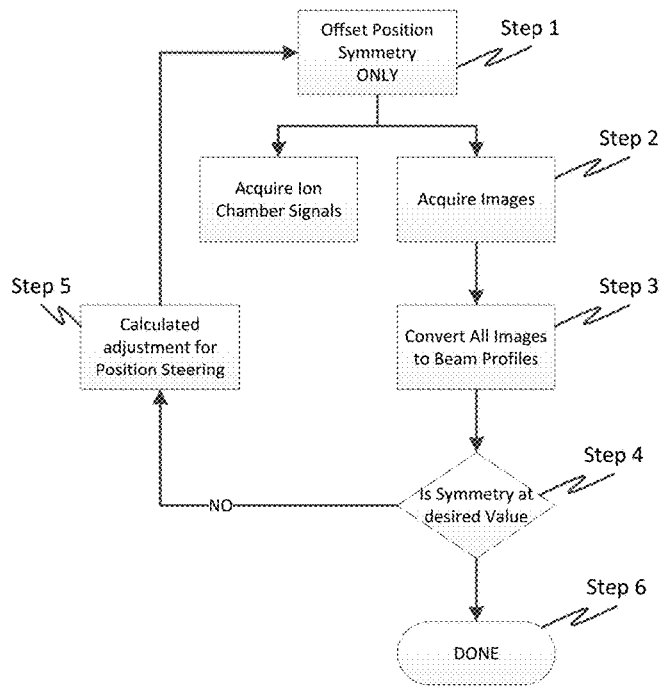

In Step 5 and Step 6 of process S113, a closed loop procedure, as shown in FIG. 40B, is utilized to achieve a first and second asymmetry value and respective ionization chamber 119 values. FIG. 40B follows the same process as FIG. 40A with the difference that position steering is used to create the asymmetry rather than angle steering.

In Step 7 the ionization chamber 119 values are calibrated for all 4 zones of angle and position feedbacks. The exact calibration equation is system 103 dependent but will utilize the set of 3 asymmetry values for each angle and position steering induced asymmetries. Once the calibration has been completed, process S113 can conclude at Step 8.

b. Alternative Embodiment

In Step 1 of the alternative calibration process S113', as shown in FIG. 41, an EPID 112 is positioned at a desired position, central to the radiation beam axis, typically at 100 cm. Then in Step 2, a series of alternating image pairs are acquired using the EPID 112. The taking of alternating image pairs involves taking successive pairs of dark and flood field images. The image pairs are generally so captured for a period of time (i.e., a number of image pairs or elapsed time) and an average integrated image is generated from the image pairs. While the images are acquired using the EPID 112 in Step 2, the ionization chamber 119 also captures the dosimeter values.

Figure 41A:
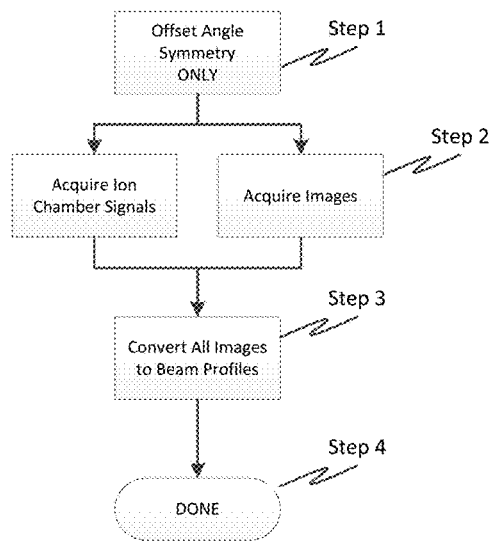

In Step 3, an open loop procedure, as shown in FIG. 41A, is employed to set an initial value of desired asymmetry using the EPID 112 all while capturing the ionization chamber 119 dosimeter values.

The open loop procedure, as shown in FIG. 41A, is executed as follows. In Step 1, expected asymmetries are introduced into the radiation beam profile by systematically varying the 2R (radial) and 2T (transverse) angle steering coil currents. This allows for the introduction of an asymmetry error of an expected magnitude. Then in Step 2 a series of alternating image pairs are acquired using the EPID 112. While the images are acquired using the EPID 112 in Step 2, the ionization chamber 119 also captures the dosimeter values. In Step 3, each of the integrated images is converted to a beam profile using the normalized conversion map.

In Step 4 of process S113', the same open loop procedure as shown in FIG. 41A is followed to achieve a second value of expected asymmetry using the EPID 112 all while capturing the ionization chamber 119 dosimeter values.

Figure 41B:
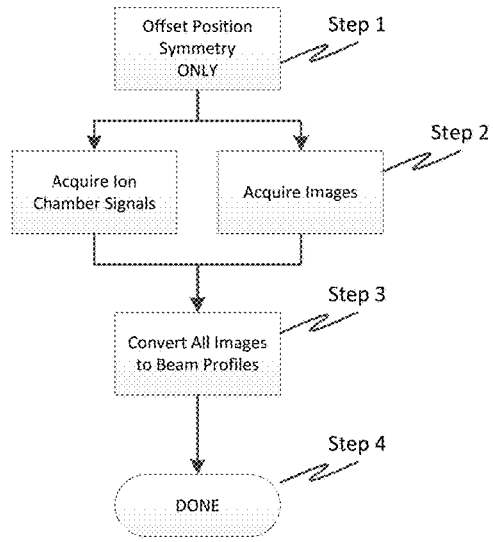

In Step 5 and Step 6 of process S113', an open loop procedure as shown in FIG. 41B is utilized to achieve a first and a second asymmetry value and respective ionization chamber 119 values. FIG. 41B follows the same process as FIG. 41A with the difference that position steering is used to create the asymmetry rather than angle steering.

In Step 7, the ionization chamber 119 values are calibrated for all 4 zones of angle and position feedbacks. The exact calibration equation is system (103) dependent but will utilize the set of 3 asymmetry values for each angle and position steering induced asymmetries. This process differs from S113 in that the calibration equations use actual asymmetry values captured by the EPID 112, rather than using set default values. Once the calibration has been completed, process S113' can conclude at Step 8.

11. Radiation Symmetry versus Gantry Rotation Verification (Step S114)

Figure 42:
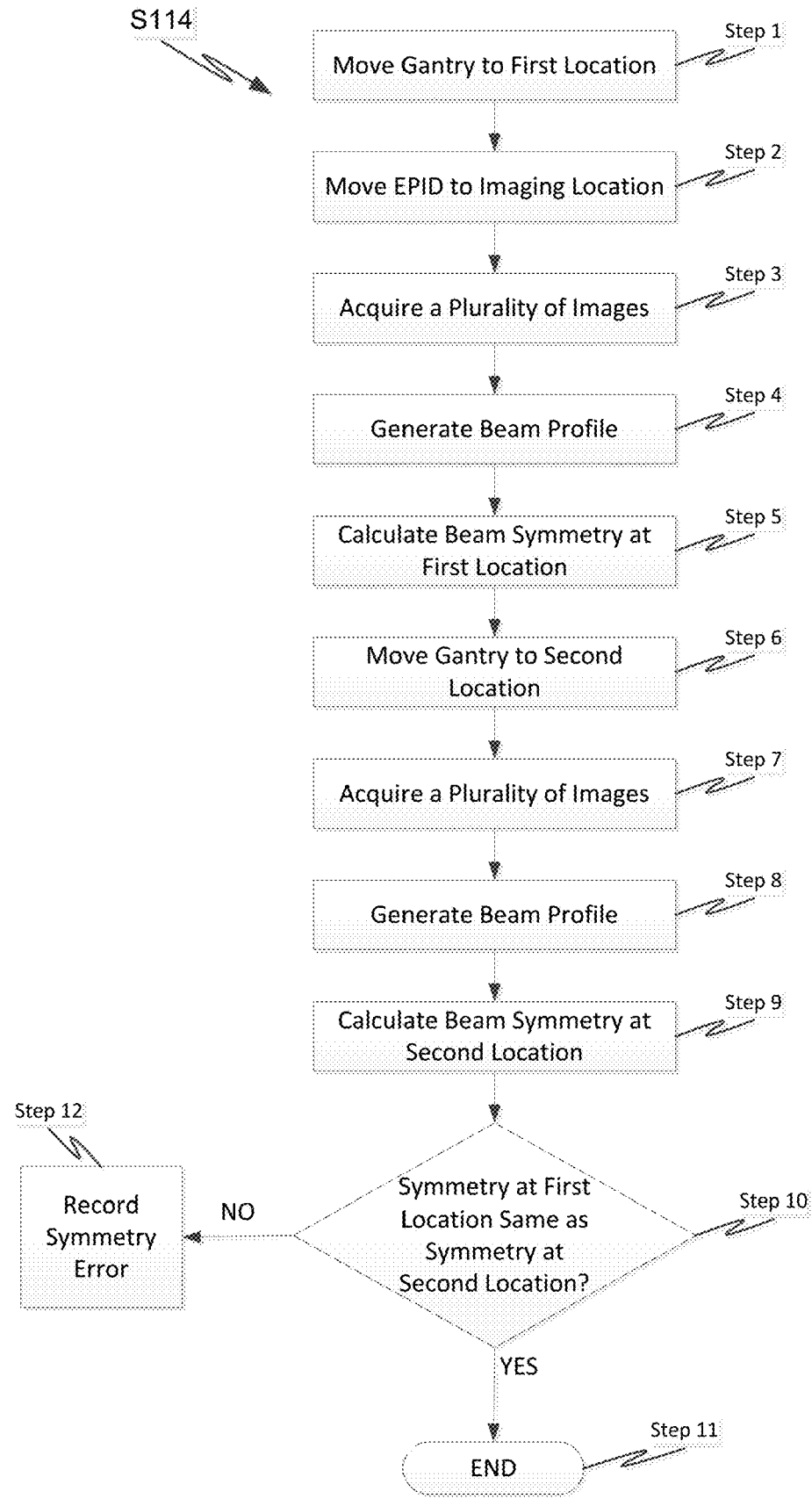
FIG. 42 illustrates a process flow for verifying radiation dose symmetry at different gantry locations.

In order to ensure that the delivered radiation beam retains its beam profile during the gantry 106 rotations, in S114, the radiation beam symmetry is verified at different gantry angles. The verification process S114 is illustrated in FIG. 42 and includes moving the gantry to a first location in Step 1 and moving an EPID 112 to a first imaging location in Step 2. Using the EPID 112, a plurality of alternating image pairs are acquired in Step 3. The taking of alternating image pairs involves taking successive pairs of dark and flood field images. The image pairs are generally captured for a period of time (i.e., a number of image pairs or a certain amount of elapsed image acquisition time) after which an average integrated image is generated from the image pairs.

In Step 4, the integrated image is converted to a beam profile using the normalized conversion map. In Step 5, the beam symmetry is computed using any one of the symmetry calculation algorithm described above. Next, the gantry 106 is moved (rotated) to a second gantry location in Step 6 and using the EPID 112, a plurality of alternating image pairs are acquired in Step 7. The taking of alternating image pairs again involves taking successive pairs of dark and flood field images. The image pairs are generally captured for a period of time (i.e., a number of image pairs or a certain amount of elapsed time) and an average integrated image is generated from the plurality of image pairs.

In Step 8, the integrated image is converted to a beam profile using the normalized conversion map. In Step 9, the beam symmetry is computed using any one of the symmetry calculation algorithms described above. In Step 10, the symmetry calculated for the first gantry location is compared to the symmetry calculated for the second gantry location. If the symmetries are the same or fall within a prescribed error range, it is concluded that the radiation beam symmetry is maintained during the gantry 106 rotation and the verification steps ends at Step 11. If the symmetries are not the same or do not fall within an accepted error range, it is determined that the radiation beam symmetry is not maintained during the gantry 106 rotation. In such a case, in Step 12, the difference between the symmetries can be recorded and used as a compensation factor to compensate for the gantry inaccuracies by adjusting the gantry rotation axis. Alternatively, if the symmetries do not match, the system 100 can be flagged for needing correction. The beam symmetry can be checked at multiple locations, such as, but not limited to, the gantry at 0°, 90°, 270°, or 360°.

The calibration/tuning process S100 of the radiation treatment device 103 which utilizes EPID 112, 112', or 112" is then terminated at S115. After the system 100 is properly tuned, the automated self-alignment system may change various parameters in order to verify and/or adjust the various determined machine characteristics, such as the flatness and symmetry, for example, of the radiation beam. For such verifications, the EPID can be used to independently offset a parameter while the radiation treatment device 103 can verify its built-in components or parameters. Further, in order to remove cross-effects between various tuning tasks, each tuning step can be automatically or manually repeated.

Automatic Self-Tuning Process

Figure 43:
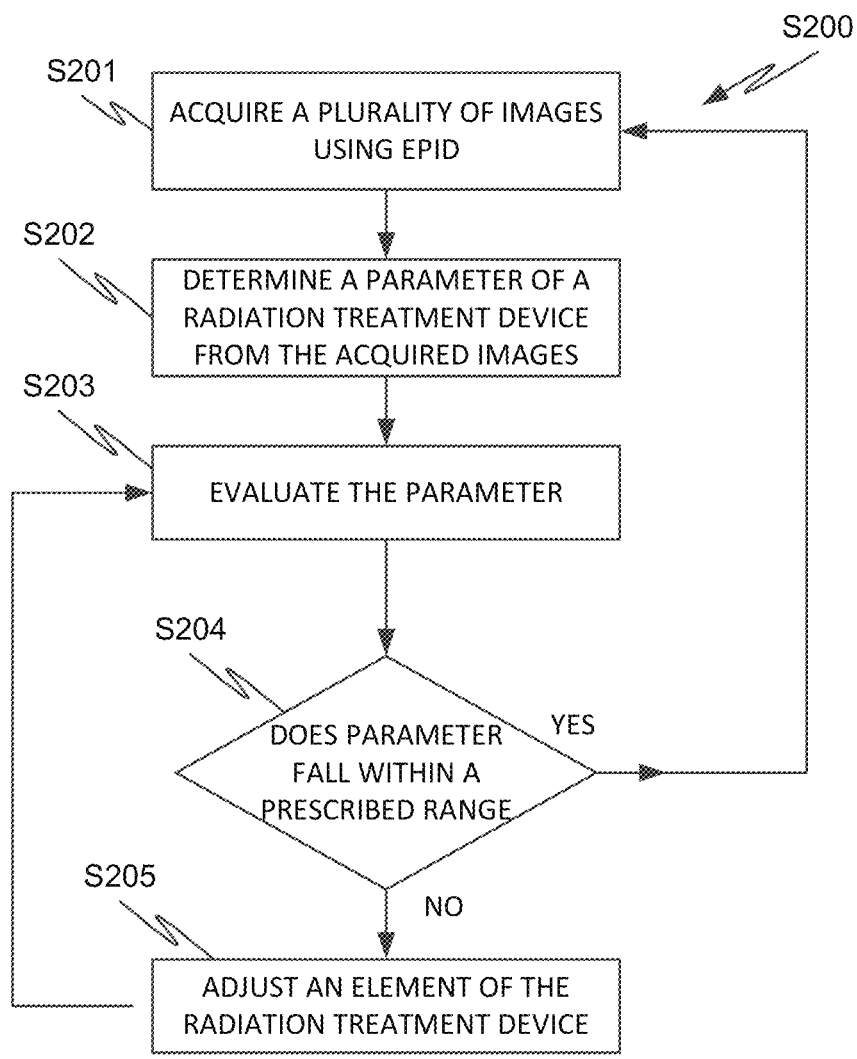
FIG. 43 illustrates process flow for self-tuning of a radiation treatment device according to one or more embodiments of the disclosed subject matter.
Figure 44B:
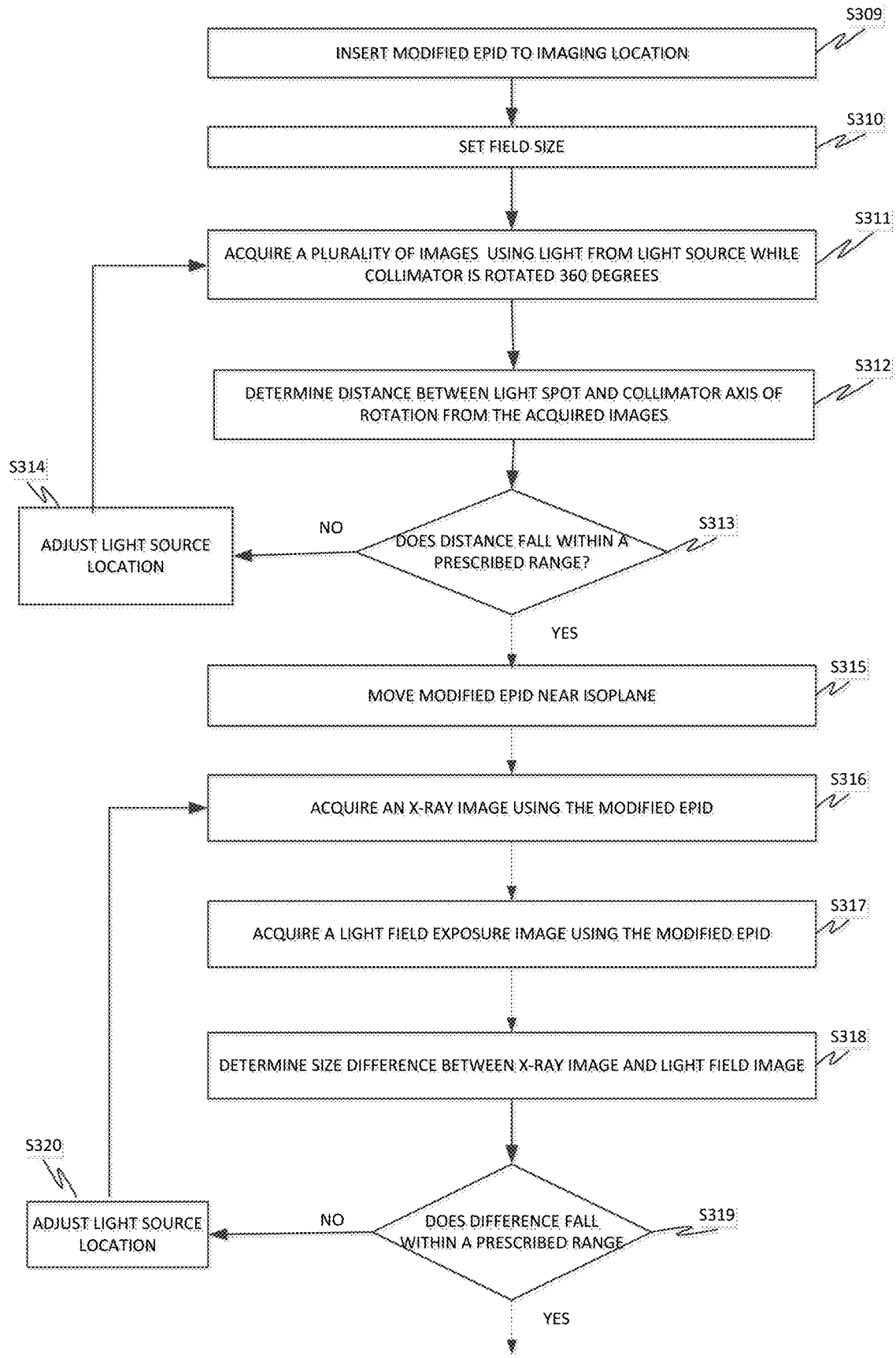
FIG. 44(A-H) illustrates, over multiple drawings sheets, a process flow for self-tuning of a radiation treatment device according to one or more embodiments of the disclosed subject matter.
Figure 44D:
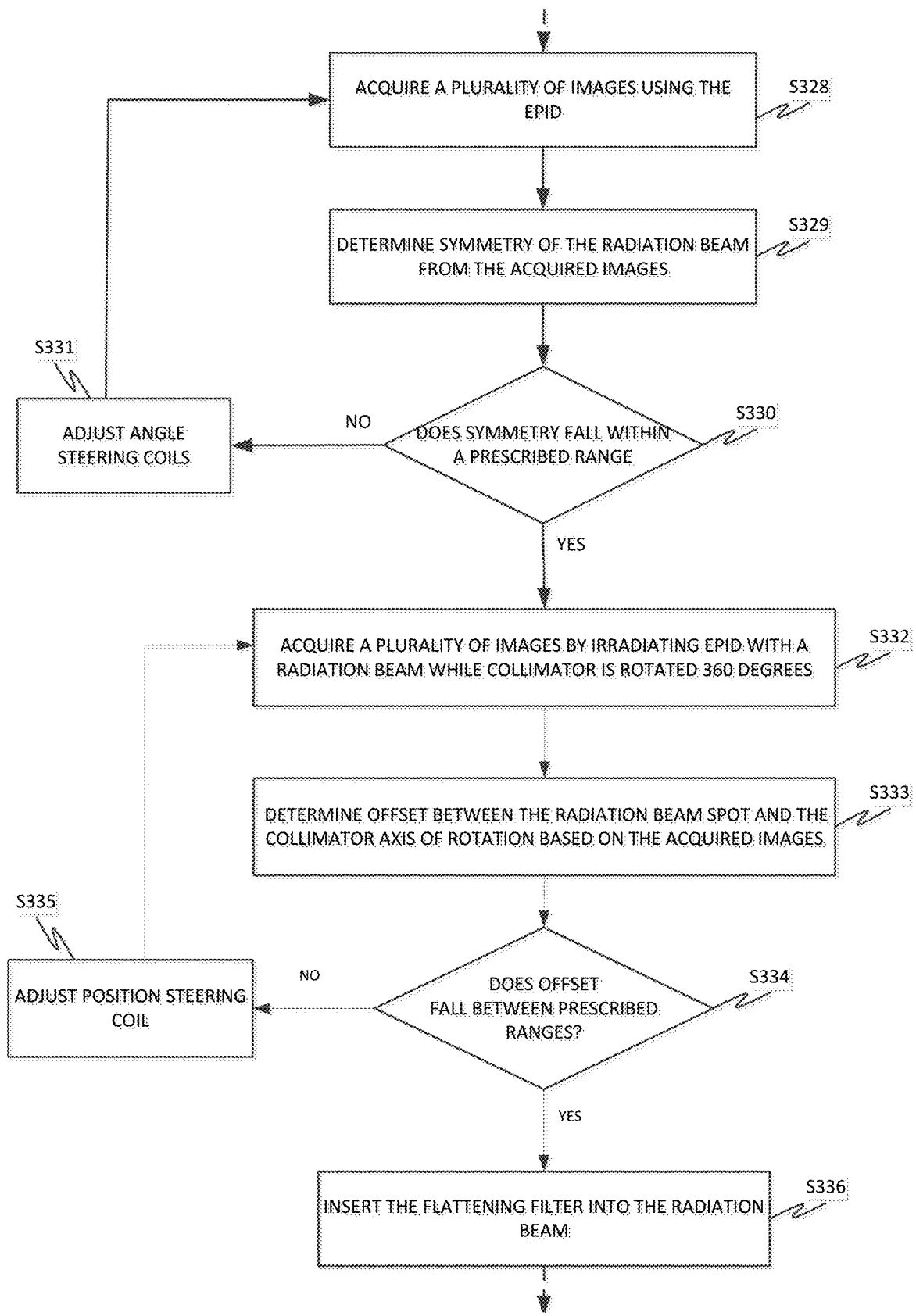
Figure 44E:
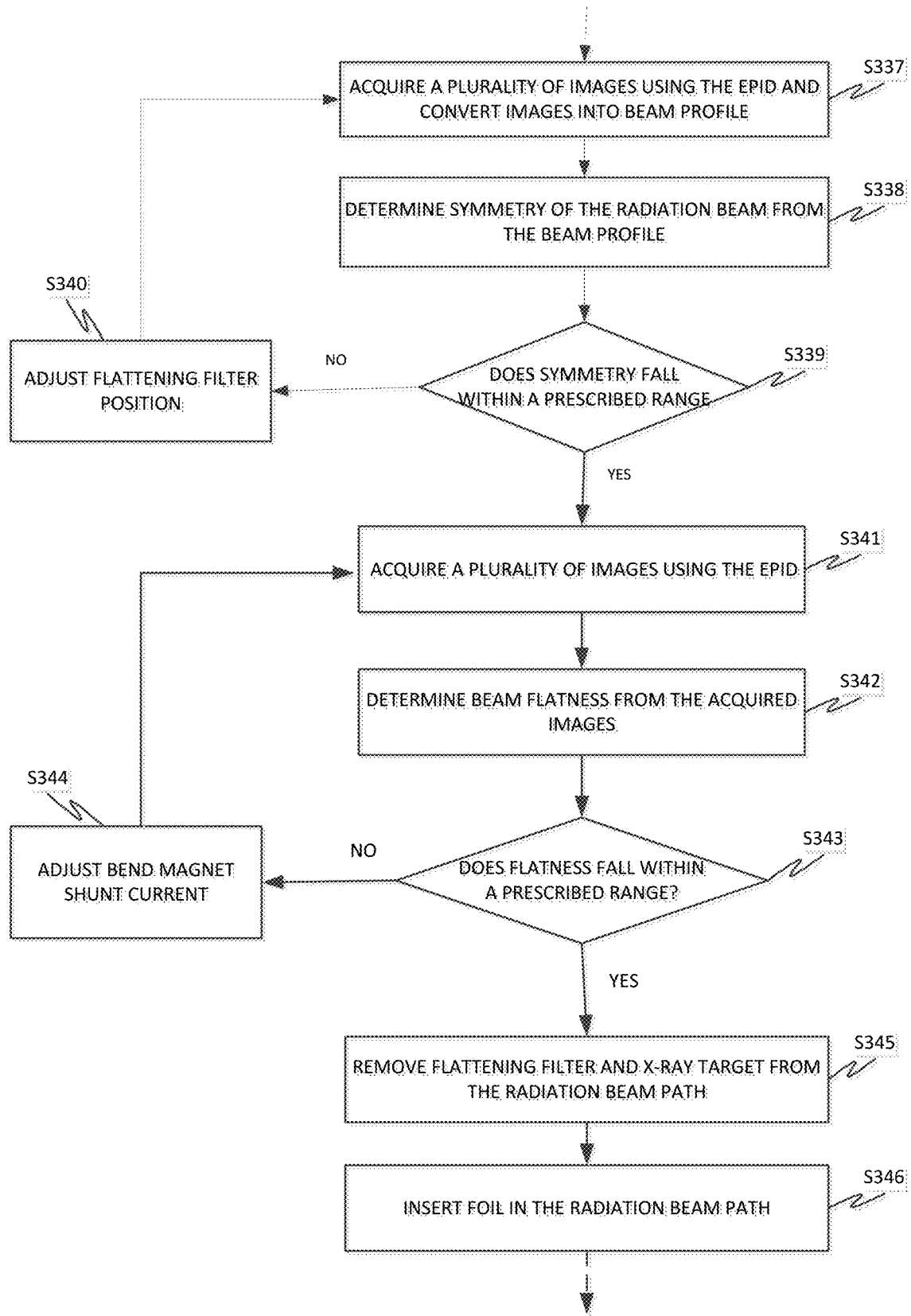
Figure 44F:
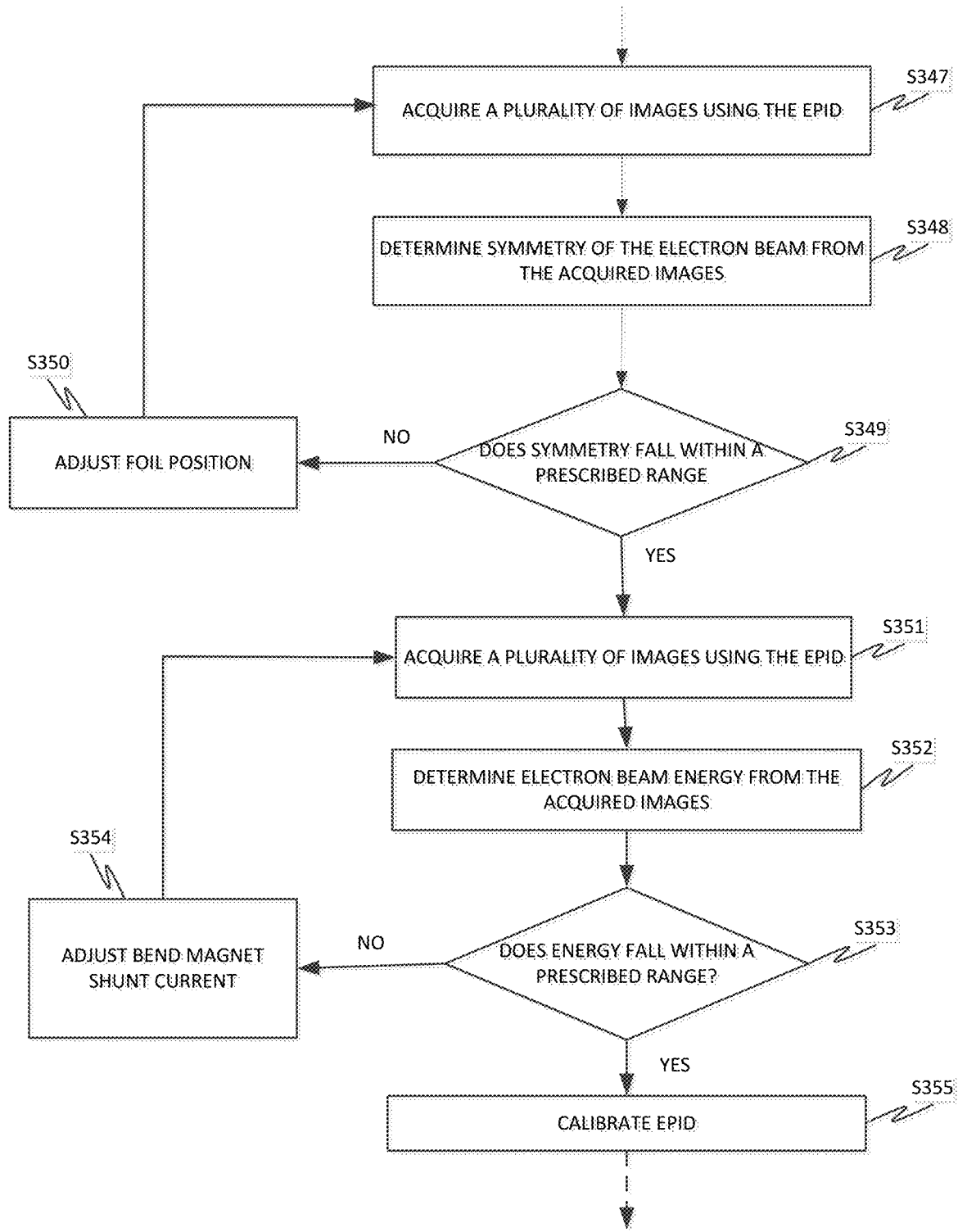
Figure 44G:
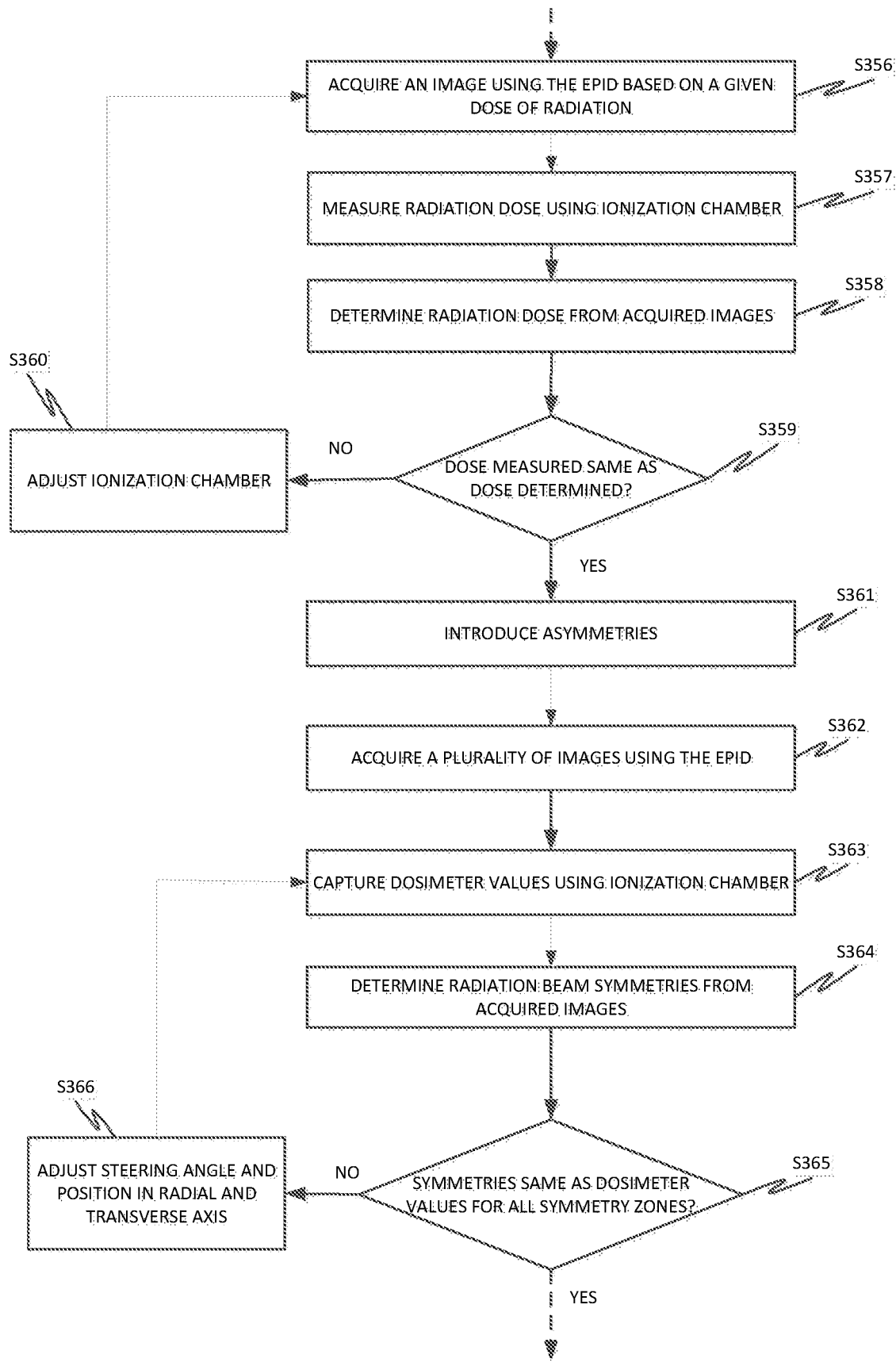

The general process S200 by which the entire radiation treatment device 103 is automatically self-tuned using an electronic portal imaging device (EPID) on the production floor is illustrated in FIG. 43. During this tuning process S200, if done in the production environment, there is neither a treatment couch 102, nor a patient 101 present.

As shown in FIG. 43, the process S200 includes steps for evaluating various parameters of the radiation treatment device 103, followed by the automatic tuning of various elements of the radiation treatment device in response to the result of the evaluation. In step S201 one or more images are taken using the EPID 112 by irradiating the EPID 112 with radiation beams (X-rays, electron-beams, or light) from the LINAC treatment head 110. From the one or more images, a parameter of the radiation treatment device 103 is determined. This parameter can be any one of: the distance of the jaws to the isoplane, beam symmetry, beam flatness, beam energy, beam linearity, beam dose, beam alignment, light field alignment, etc.

In Step S204 the parameter is evaluated to determine whether it falls within a prescribed range. If the parameter falls within a prescribed range, process steps S201-S204 are repeated to determine and evaluate another parameter of the radiation treatment device 103. If the parameter does not fall within a prescribed range, the output of a control element of the radiation treatment device 103 affecting the respective parameter is adjusted in S205 until the parameter falls within the prescribed range. The adjustment in S205 can include an adjustment in the radiation limiting (collimating) devices, the angle and position of the steering coils, the location of the flattening filters 117, the size of the bend magnet shunt current, the position of the scattering foils 127, the movement of the EPID arm support 113, the position and symmetry of the ionization chamber 119, and the position of the light source 130, for example.

Process S200 can be automatically repeated until all parameters of the device are evaluated and the corresponding control element outputs adjusted. Any number of automatic routines using any different type of feedback device can be inserted in process S200 with the same iterative tuning. When all the outputs are tuned and the parameters fall within prescribed ranges, the radiation treatment device 103 is properly tuned, and the process S200 stops.

Exemplary Automatic Self-Tuning System and Process

An exemplary automated self-tuning process S300 with specific parameter evaluation and corresponding control element output adjustment is illustrated in FIG. 44(A-H). Tuning process S300 starts by moving the EPID 112 to a location that is at or near the isoplane in S301, followed by the adjusting of the collimator jaws in S302 to a desired field size, and taking an image using the EPID in S303. The EPID is next moved to a second location along the Z axis (S304) and a second image is taken (S305). Based on the first and second images, the distance between the radiation beam spot and the EPID is calculated in S306 and this distance evaluated in S307. If the distance is not the prescribed distance, the EPID arm position is adjusted in S308 along the Z axis based on the calculated difference until the distance is acceptable. The acceptable distance indicates that the EPID arm structure is calibrated along the Z axis.

Once the imager arm is calibrated, the process S300 automatically moves on to S309 where the EPID is removed from the radiation treatment device and a modified EPID 112' or 112" is inserted. A desired field size is also set using the collimator jaws in S310. Using the modified EPID 112' or 112", one or more images are acquired in S311 using the light field from the light source 130, while the collimator is rotated 360 degrees. From the images so acquired, the offset between the light spot and the collimator axis of rotation is determined in S312. If the offset is not within a prescribed range (S313), the light source location is adjusted in S314 until the offset is within an accepted range. If the offset is within an accepted offset range, the light spot coincides with the collimator axis of rotation and the process S300 moves on to adjust the light source 130 to be at the same distance from the isoplane as the X-ray target 118.

In S315, the modified EPID is moved at or near the isoplane, and an X-ray image (S316) as well as a light field image (S317) is acquired using the modified EPID. The two images are then compared in S318 to determine the image size difference between the two. If the difference between the image sizes is not acceptable (S319), the light source 130 is adjusted in S320 until the image sizes coincide. If the image sizes coincide within a prescribed threshold level, the tuning process proceeds to step S321 where the collimator jaws are set at expected distances from the isoplane. A plurality of images is next taken in S322. From the images, the projected distances of the collimator jaws on the isoplane are determined in S323 and evaluated in S324. If the projected distances do not fall within the prescribed values, the collimator jaw positions are automatically adjusted in S325 until they do. If the projected distances are within specification, the EPID is moved at or near the isoplane S326, the flattening filters 117 are removed from the radiation beam and the collimator jaws are set to a desired field opening (S327).

With this setup, one or more images are acquired in S328 from which the radiation beam symmetry is determined in S329. The symmetry is evaluated in S330 and if it does not falls within an accepted range, the steering coil radial and transverse angles are adjusted (S331) until the symmetry is acceptable.

If symmetry acceptable, the collimator jaws are positioned to generate a specific field and alternating image pairs are acquired in S332 while the collimator is rotated through 360 degrees. This process is repeated with a second collimator jaw setting to acquire a second set of image pairs. From the two image pairs, the difference between the centers of the images is determined and from that the offset between the radiation beam spot and the collimator axis of rotation is determined in S333. If the offset does not fall within a prescribed range (S334), the position steering coils are adjusted in S335 until the circle centers coincide. When the circle centers coincide, the radiation beam spot and the collimator axis of rotation coincide.

The process S300 moves on to S336 to insert a flattening filter into the radiation beam at a default position. Using the EPID, one or more images are acquired in S337 and the images are converted into beam profiles. From the acquired images, the radiation beam profile is generated and the symmetry of the radiation beam is calculated (S338). If the symmetry does not fall within a prescribed range (S339), the flattening filter position is adjusted in S340 until it does.

If the symmetry is acceptable, process S300 moves on to acquire one or more images in S341, from which the beam flatness is determined in S342. The beam flatness is evaluated in S343, and if the flatness is not acceptable, the bend magnet shunt current is adjusted in S344 until the flatness is acceptable.

If the flatness is acceptable, the radiation beam energy is acceptable and the process S300 continues by removing the flattening filter and the X-ray target from the radiation beam in S345 and inserting scattering foils into the electron beam path in S346. With this setup, one or more images are acquired in S347 using the EPID, from which the symmetry of the electron-beam profile is determined in S348. If the symmetry does not fall within a prescribed range the scattering foil position is adjusted in S350 until the correct symmetry is achieved.

If the symmetry is within the accepted range, the process S300 continues by moving the EPID to an imaging position and acquiring one or more images in S351, from which the flatness and ultimately the energy of the electron-beam is calculated in S352. If the beam flatness is not acceptable (S353), the bend magnet shunt current is adjusted in S354 until the appropriate beam flatness is achieved. The correct flatness indicates the correct electron-beam energy.

Then, the radiation treatment device 103 is switched into the photon-mode and the EPID is calibrated against a calibrated dosimeter in S355. An image is taken in S356 using the EPID based on a radiation beam having a specific radiation dose. The radiation dose is also measured using the ionization chamber in S357. The radiation dose is next determined from the EPID images in S358 and the determined radiation dose is compared to the radiation dose measured by the ionization chamber in S359. If the determined radiation dose is not the same as the measured radiation dose, the ionization chamber is calibrated in S360 until the radiation doses coincide. When the measured and the determined radiation doses coincide, the ionization chamber is calibrated.

Next, known asymmetries are introduced into the radiation in S361, and for each asymmetry an image is acquired using the EPID in S362. Using the images, the radiation beam asymmetries are calculated in S364. The dosimeter values are also captured using the ionization chamber in S363. Then, for each symmetry zone, the symmetry determined from the image is compared to the dosimeter value measured using the ionization chamber in S365. If the symmetries are the same as the corresponding dosimeter values, the ionization chamber is calibrated to correctly read the symmetries in all four zones. If the symmetries are not the same as the corresponding dosimeter values, the steering angle and/or position in the radial and/or transverse directions are adjusted in S366 until the symmetries and dosimeter values coincide.

The process S300 moves on by positioning the EPID at an imaging location and acquiring images at different gantry angles in S367. For each image acquired, the radiation beam symmetry is determined in S368. If the symmetries are not the same for all gantry angles (S369), the gantry in adjusted in S370. If the symmetries are maintained during the gantry rotation, the tuning process ends at S371.

It will be appreciated that the above described calibration systems and methods can be used either on the production floor during the original tuning of the radiation treatment device, during the initial installation of the radiation treatment system, for verification to retune the machine during preventative maintenance inspection, or as a periodic check or verification during the routine usage of the radiation treatment device.

It will also be appreciated that the above described calibration process could be performed as a fully automated closed-loop process or a partially automated process. Moreover, any of the calibration/verification steps of the self-tuning process could be omitted and the steps could be performed in any desired order.

It will also be appreciated that any of the above described calibration process steps could be performed using either an EPID 112 or a modified EPID 112' or EPID 112".

It will be appreciated that the processes, systems, and sections described above can be implemented in hardware, hardware programmed by software, software instruction stored on a non-transitory computer readable medium or a combination of the above. For example, a method for can be implemented using a processor configured to execute a sequence of programmed instructions stored on a non-transitory computer readable medium. The processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C #.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms.

Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, an imaging-based self-tuning system and method for a radiation treatment system. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method for calibrating a radiation treatment device, the radiation treatment device including control elements configured to control parameters of the radiation treatment device, the method comprising:
    (i) acquiring, using an imaging device, one or more images representing beam fields produced by a beam source;
    (ii) determining a parameter of the radiation treatment device from the one or more images, the parameter relating to an output of a control element;
    (iii) evaluating the parameter against a predefined standard;
    (iv) adjusting the output of the control element based on the result of the evaluating until the parameter meets the predefined standard; and
    (v) repeating steps (i) through (iv) for one or more additional parameters,
    wherein one of the parameters is the imaging device position with respect to a coordinate frame of the radiation treatment device, and
    wherein the control elements include beam collimator devices, beam angle steering coils, beam position steering coils, shunt current sources, imaging device moving arms, beam flattening filters, beam scattering filters, dosimeters, gantry positioning devices, light sources, X-ray sources, and gun-cathode heating controls.

2. The method of claim 1, wherein the determining the imaging device position includes determining a location of the projection of the beam center on the imaging device, and determining a distance of the imaging device from the beam source.

3. The method of claim 2, wherein the determining the distance from the beam source includes acquiring a first and a second image in (i) with the imaging device positioned at two different locations from the beam source, and calculating the distance between the imaging device and the beam source based on an amount by which the imaging device moved between the two locations and the beam field sizes at the first and second locations of the imaging device.

4. The method of claim 3, wherein the calculating includes calculating the distance (Z) of the imager from the beam source using $$Z = \frac{\partial Z}{\frac{D_B}{D_A} - 1},$$

where, $\partial Z$ is the amount by which the imaging device was moved between the two locations, $D_A$ is the size of the beam field at the first location of the imaging device, and $D_B$ is the size of the beam field at the second location of the imaging device.

5. The method of claim 1, wherein the adjusting is one of automatic and a combination of automatic and manual.

6. The method of claim 1, wherein the adjusting is iterative.

7. The method of claim 1, wherein the adjusting includes repeating steps (i) through (iii) after an initial adjustment.

8. The method of claim 1, wherein the one or more images are acquired using one of an electronic portal imaging device (EPID) and a modified electronic portal imaging device (modified EPID).

9. The method of claim 8, wherein in the modified EPID a scintillator layer is directly exposed to the beam from the beam source.

10. The method of claim 8, wherein in the modified EPID a scintillator layer is exposed to the beam through an optical grade plastic cover.

11. The method of claim 1, wherein the beam source is one of a radiation beam source, an electron-beam source, and a light field source.

12. The method of claim 11, wherein the beam fields include an X-ray field, an electron-beam field, or a light field.

13. The method of claim 1, wherein the other parameters include beam symmetry, beam flatness, beam energy, beam asymmetry, beam alignment, beam dose linearity, beam field size, beam position, beam shape, and collimator position from isoplane.

14. The method of claim 13, wherein determining collimator position from isoplane includes:
calculating collimator position from a first image acquired at a first location of a collimator of the radiation treatment device and from a second image acquired at a second location of the collimator; and
determining projected distances of the collimator on the isoplane from the calculated collimator positions.

15. The method of claim 13, wherein determining beam symmetry includes:
acquiring a series of alternating dark field/flood field image pairs in (i);
generating a beam profile from the series of alternating dark field/flood field image pairs; and
calculating beam symmetry from the beam profile using a symmetry calculation algorithm.

16. The method of claim 13, wherein determining beam position includes determining beam coincidence with an axis of rotation of a collimator of the radiation treatment device and includes:
acquiring a first integrated image at a first collimator aperture while the collimator is rotated through a first rotation angle, and acquiring a second integrated image at a second collimator aperture while the collimator is rotated through a second rotation angle in step (i);
determining a center of the first integrated image and a center of the second integrated image; and
calculating difference between the first and second image centers.

17. The method of claim 13, wherein determining beam position includes determining beam coincidence with an axis of rotation of a collimator of the radiation treatment device and includes:
inserting a collimating device into the beam path, the collimating device including a first and a second coaxial cone allowing the beam to pass therethrough;
acquiring a plurality of images at a plurality of collimator positions;
measuring a position of a center of the first cone and a position of a center of the second cone for an acquired image;
calculate a best fit circle for center positions of the first cone and for center positions of the second cone;
calculate a difference between a center of the best fit circle for the first cone and a center of the best fit circle for the second cone; and
determine a shift in the position of the beam source from the axis of rotation of the collimator based on the calculated difference.

18. The method of claim 13, wherein determining beam flatness includes:
converting an image acquired in (i) to a beam profile; and
calculating flatness from the beam profile.

19. The method of claim 13, wherein determining beam energy includes:
positioning a first scattering foil having a first thickness into the beam and acquiring a first image;
positioning a second scattering foil having a second thickness into the beam and acquiring a second image; and
calculating the beam energy based on the intensities of the first and second images and the half value layer of the scattering foil material.

20. The method of claim 13, wherein determining beam dose linearity includes:
determining a beam dose from an image acquired in (i);
measuring beam dose using a dosimeter internal to the radiation treatment device; and
comparing the determined and measured doses.

21. The method of claim 13, wherein determining beam symmetry includes determining beam symmetry at different detecting zones of an internal dosimeter of the radiation treatment device and includes:
introducing known asymmetries into the beam;
acquiring images for the asymmetries;
converting the images to beam profiles;
calculating symmetries for the beam profiles;
measuring dosimeter values using the internal dosimeter for the asymmetries introduced; and comparing the calculated symmetry with a corresponding measured dosimeter value.

22. The method of claim 13, wherein determining beam alignment includes determining alignment of radiation beam source position with a position of a light field source included in the radiation treatment device.

23. The method of claim 22, wherein the determining includes:
acquiring an X-ray image and a light field image in step (i);
determining a center of the X-ray image and a center of the light field image acquired in step (i); and
determining a difference between the two centers.

24. The method of claim 22, wherein the determining includes:
generating an integrated image of an X-ray image and a light field image by acquiring the X-ray image and the light field image in step (i) while a collimator of the radiation treatment device is rotated through a rotation angle of the collimator, the integrated image having a shape of a circle;
calculating a diameter of the circle obtained from the integrated image; and
determining whether the calculated diameter is a minimum diameter.

25. A method for calibrating a radiation treatment device including an electronic portal imaging device (EPID) positioned on an imager arm for generating images during patient treatment, comprising:
prior to patient treatment, generating, using the EPID, a set of images of beam fields produced by a beam source;
determining a parameter of the radiation treatment device from beam field information contained in the set of images;
evaluating whether the parameter falls within a corresponding prescribed range;
adjusting one or more elements of the radiation treatment device affecting the parameter if the parameter does not fall within the prescribed range;
generating, using the EPID, another set of images of beam fields, and determining another parameter from the another set of images; and
repeating the evaluating and adjusting steps for the another parameter,
wherein the elements include the beam source, collimator devices, beam angle steering coils, beam position steering coils, shunt current sources, imaging device moving arms, beam flattening filters, beam scattering filters, dosimeters, gantry positioning devices, light sources, X-ray sources, and gun-cathode heating controls.

26. The method of claim 25, wherein the parameters include: beam alignment, beam symmetry, beam asymmetry, beam shape, beam energy, beam flatness, beam dose linearity, beam field size, beam position, EPID's position relative to a coordinate frame of the radiation treatment device, and collimator position from an isoplane of the radiation treatment device.

27. The method of claim 26, wherein the beam field information contained in the generated images include location of center of beam as projected onto the EPID panel, beam field size, beam field shape, beam field profile, beam field profile symmetry, beam field intensity, beam dose, beam field size difference between images, difference between centers of field beams in image pairs, and projected distance from an element to isoplane of radiation treatment device.

28. The method of claim 27, wherein the EPID's position relative to a coordinate frame of the radiation treatment device is determined from the information regarding location of the center of the beam field as projected onto the EPID panel contained in the set of images and information regarding the beam field sizes.

29. The method of claim 27, wherein the beam symmetry is determined from the beam field profile information contained in the set of images or from beam field profile symmetry information contained in the set of images.

30. The method of claim 27, wherein the beam position is determined from the difference between centers of field beams in image pairs contained in the set of images.

31. The method of claim 27, wherein the beam flatness is determined from the beam field profile information contained in the set of images.

32. The method of claim 27, wherein the beam energy is determined from the beam field intensity information contained in the set of images.

33. The method of claim 27, wherein the beam dose linearity is determined from the beam dose information contained in the set of images.

34. The method of claim 27, wherein the beam alignment is determined from information regarding beam field size differences contained in the set of images.

35. The method of claim 25, wherein the adjusting is one of automatic and a combination of automatic and manual.

36. The method of claim 25, wherein the beam source is one of a radiation beam source, an electron-beam source, and a light field source, and the beam fields include X-ray fields, electron-beam fields, or light fields.

37. A method for calibrating a radiation treatment device, comprising:
generating images representing beam fields produced by a beam source of the radiation treatment device using an imaging device; and
using information obtained from the generated images to:
calibrate the imaging device's axis of motion with respect to the radiation treatment device; and
calibrate one or more elements of the radiation treatment device that affect one or more parameters of the radiation treatment device, the parameters including beam alignment, beam symmetry, beam asymmetry, beam shape, beam energy, beam flatness, beam dose linearity, beam field size, beam position, imaging device position relative to the beam source, and collimator position from an isoplane of the radiation treatment device,
wherein the elements include the beam source, collimator devices, beam angle steering coils, beam position steering coils, shunt current sources, imaging device moving arms, beam flattening filters, beam scattering filters, dosimeters, gantry positioning devices, light sources, X-ray sources, and gun-cathode heating controls.

38. The method of claim 37, wherein the information obtained from the images includes location of center of beam as projected onto the imaging device panel, beam field size, beam field shape, beam field profile, beam field profile symmetry, beam field intensity, beam dose, beam field size difference between images, difference between centers of field beams in image pairs, and projected distance from an element to isoplane of radiation treatment device.

39. The method of claim 37, wherein the calibrating of the imaging device's axis of motion includes:
calibrating a center location of the imaging device with respect to a coordinate frame of the radiation treatment device;

setting the origins of the X and Y axis of the imaging device based on the calibrated center location; and adjusting the Z axis of the imaging device based on a distance between the imaging device and the beam source determined from information contained in the generated images.

40. The method of claim 38, wherein the calibrating of one or more elements includes one or more of:

calibrating the beam source to align the beam to the beam collimating device's axis of rotation;

calibrating the steering coils to achieve symmetric beams and beam coincidence with the collimating device's axis of rotation;

calibrating the X-ray filter to generate flattened X-ray beams;

adjusting the bend magnet shunt current to generate a desired X-ray energy or electron-beam energy output;

calibrating foil alignment to achieve symmetric X-ray beams; and calibrating the ionization chamber for beam dose linearity and symmetry.

* * * * *